(12) United States Patent
    Squires

(10) Patent No.: US 9,969,776 B2
(45) Date of Patent: May 15, 2018

(54) DRUG CONJUGATES FOR DELIVERING COMPOUNDS TO SENESCENT CELLS

(71) Applicant: Unity Biotechnology, Inc., San Francisco, CA (US)

(72) Inventor: Shayne Squires, Cedarburg, WI (US)

(73) Assignee: UNITY BIOTECHNOLOGY, INC., Brisbane, CA (US)

( * ) Notice: Subject to any disclaimer, the term of this patent is extended or adjusted under 35 U.S.C. 154(b) by 0 days. days.

(21) Appl. No.: 15/365,297

(22) Filed: Nov. 30, 2016

(65) Prior Publication Data

US 2017/0087252 A1     Mar. 30, 2017

Related U.S. Application Data

(60) Continuation of application No. 14/750,941, filed on Jun. 25, 2015, now abandoned, which is a division of application No. 14/557,316, filed on Dec. 1, 2014, now abandoned, which is a continuation of application No. 12/809,952, filed as application No. PCT/US2008/013913 on Dec. 19, 2008, now abandoned.

(60) Provisional application No. 61/015,416, filed on Dec. 20, 2007.

(51) Int. Cl.

| | |
|---|---|
| *A61K 38/10* | (2006.01) |
| *A61K 47/64* | (2017.01) |
| *A61K 49/00* | (2006.01) |
| *C07K 14/00* | (2006.01) |
| *A61K 51/08* | (2006.01) |
| *A61K 51/10* | (2006.01) |
| *G01N 33/574* | (2006.01) |
| *A61K 35/12* | (2015.01) |
| *C07K 16/28* | (2006.01) |
| *A61K 38/16* | (2006.01) |
| *C12N 15/10* | (2006.01) |
| *C12N 15/86* | (2006.01) |
| *G01N 33/50* | (2006.01) |
| *A61K 47/68* | (2017.01) |
| *A61K 39/00* | (2006.01) |

(52) U.S. Cl.
    CPC ............ *C07K 14/00* (2013.01); *A61K 35/12* (2013.01); *A61K 38/10* (2013.01); *A61K 38/16* (2013.01); *A61K 38/168* (2013.01); *A61K 47/64* (2017.08); *A61K 47/6803* (2017.08); *A61K 47/6849* (2017.08); *A61K 47/6851* (2017.08); *A61K 49/0004* (2013.01); *A61K 49/0056* (2013.01); *A61K 51/08* (2013.01); *A61K 51/088* (2013.01); *A61K 51/1027* (2013.01); *C07K 16/28* (2013.01); *C12N 15/1037* (2013.01); *C12N 15/86* (2013.01); *G01N 33/5032* (2013.01); *G01N 33/57492* (2013.01); *A61K 2039/505* (2013.01); *C07K 2317/24* (2013.01); *C07K 2317/73* (2013.01); *C07K 2317/76* (2013.01); *C07K 2317/92* (2013.01); *C12N 2710/10043* (2013.01); *G01N 2800/50* (2013.01)

(58) Field of Classification Search
    None
    See application file for complete search history.

(56) References Cited

U.S. PATENT DOCUMENTS

| | | |
|---|---|---|
| 6,201,020 B1 | 3/2001 | Zhang et al. |
| 7,390,799 B2 | 6/2008 | Bruncko et al. |
| 7,642,260 B2 | 1/2010 | Bruncko et al. |
| 7,767,684 B2 | 8/2010 | Bruncko et al. |
| 7,829,556 B2 | 11/2010 | Bemis et al. |
| 7,842,681 B2 | 11/2010 | Elmore et al. |
| 7,851,626 B2 | 12/2010 | Ding et al. |
| 7,879,857 B2 | 2/2011 | Mabire et al. |
| 7,928,104 B2 | 4/2011 | Mabire et al. |
| 7,973,161 B2 | 7/2011 | Bruncko et al. |
| 8,071,623 B2 | 12/2011 | Jones et al. |
| 8,168,645 B2 | 5/2012 | Baell et al. |
| 8,343,967 B2 | 1/2013 | Ding et al. |
| 8,426,422 B2 | 4/2013 | Hexamer et al. |
| 8,518,970 B2 | 8/2013 | Baell et al. |
| 8,541,417 B2 | 9/2013 | Brown et al. |
| 8,557,983 B2 | 10/2013 | Bruncko et al. |
| 8,563,735 B2 | 10/2013 | Bruncko et al. |
| 8,586,754 B2 | 11/2013 | Bruncko et al. |
| 8,614,318 B2 | 12/2013 | Bruncko et al. |
| 8,624,027 B2 | 1/2014 | Shah et al. |
| 9,089,561 B2 | 7/2015 | Yamaguchi et al. |
| 2002/0164794 A1 | 11/2002 | Wernet |
| 2005/0019865 A1 | 1/2005 | Kihm et al. |
| 2005/0158288 A1 | 7/2005 | Faustman |
| 2007/0054399 A1 | 3/2007 | Kim et al. |
| 2007/0178071 A1 | 8/2007 | Westenfelder |

(Continued)

FOREIGN PATENT DOCUMENTS

| | | |
|---|---|---|
| WO | WO-03028443 A1 | 4/2003 |
| WO | WO-2006018632 A2 | 2/2006 |

(Continued)

OTHER PUBLICATIONS

Adams. Healing and hurting: molecular mechanisms, functions, and pathologies of cellular senescence. Mol Cell. Oct. 9, 2009;36(1):2-14. doi: 10.1016/j.molcel.2009.09.021.

(Continued)

*Primary Examiner* — Daniel C Gamett
(74) *Attorney, Agent, or Firm* — Michael Schiff; Wilson Sonsini Goodrich & Rosati

(57) ABSTRACT

Disclosed are agents (e.g., peptides, polypeptides, proteins, small molecules, antibodies, and antibody fragments that target senescent cells) and methods of their use for imaging senescent cells in vivo and for treating or preventing cancer, age-related disease, tobacco-related disease, or other diseases and disorders related to or caused by cellular senescence in a mammal. The methods include administering one or more of the agents of the invention to a mammal, e.g., a human. The agents, which specifically bind to senescent cells, can be labeled with a radioactive label or a therapeutic label, e.g., a cytotoxic agent.

18 Claims, 5 Drawing Sheets

(56) References Cited

U.S. PATENT DOCUMENTS

| | | |
|---|---|---|
| 2007/0212732 A1 | 9/2007 | Uchida et al. |
| 2007/0259425 A1 | 11/2007 | Dzau et al. |
| 2007/0264238 A1 | 11/2007 | Shaw et al. |
| 2008/0221132 A1 | 9/2008 | Cai et al. |
| 2009/0202654 A1 | 8/2009 | Nixon |
| 2009/0208935 A1 | 8/2009 | Roninson et al. |
| 2009/0281129 A1 | 11/2009 | Chang et al. |
| 2010/0190807 A1 | 7/2010 | Porter et al. |
| 2010/0221183 A1 | 9/2010 | Squires |
| 2010/0310504 A1 | 12/2010 | Lowe et al. |
| 2011/0027806 A1 | 2/2011 | Gordon et al. |
| 2011/0124607 A1 | 5/2011 | Park et al. |
| 2011/0212909 A1 | 9/2011 | Wen et al. |
| 2011/0300112 A1 | 12/2011 | Marban et al. |
| 2012/0156134 A1 | 6/2012 | Squires |
| 2013/0267534 A1 | 10/2013 | Bruncko et al. |
| 2013/0287763 A1 | 10/2013 | Sathyanarayanan et al. |
| 2013/0288980 A1 | 10/2013 | De et al. |
| 2013/0302283 A1 | 11/2013 | Kihm |
| 2014/0017341 A1 | 1/2014 | Gourlaouen |
| 2014/0073640 A1 | 3/2014 | Judd et al. |
| 2014/0275082 A1 | 9/2014 | Tao et al. |
| 2014/0328893 A1 | 11/2014 | Adnot |
| 2014/0329854 A1 | 11/2014 | Larsen et al. |
| 2014/0378683 A1 | 12/2014 | Porter et al. |
| 2015/0044184 A1 | 2/2015 | Chen et al. |
| 2015/0056195 A1 | 2/2015 | Bertolotto-Ballotti |
| 2015/0072950 A1 | 3/2015 | Sauve et al. |
| 2015/0072972 A1 | 3/2015 | Mevellec et al. |
| 2015/0140036 A1 | 5/2015 | Mannick et al. |
| 2015/0151001 A1 | 6/2015 | Squires |
| 2015/0210717 A1 | 7/2015 | Günes et al. |
| 2016/0017033 A1 | 1/2016 | Squires |
| 2016/0166718 A1 | 6/2016 | Squires |

FOREIGN PATENT DOCUMENTS

| | | |
|---|---|---|
| WO | WO-2008113131 A1 | 9/2008 |
| WO | WO-2009039553 A1 | 4/2009 |
| WO | WO-2009085216 A2 | 7/2009 |
| WO | WO-2010000491 A1 | 1/2010 |
| WO | WO-2010148447 A1 | 12/2010 |
| WO | WO-2011068561 A1 | 6/2011 |
| WO | WO-2011150016 A1 | 12/2011 |
| WO | WO-2013054153 A1 | 4/2013 |
| WO | WO-2013152038 A1 | 10/2013 |
| WO | WO-2013170174 A1 | 11/2013 |
| WO | WO-2014041125 A1 | 3/2014 |
| WO | WO-2014174511 A1 | 10/2014 |
| WO | WO-2014186878 A1 | 11/2014 |
| WO | WO-2015044649 A1 | 4/2015 |
| WO | WO-2015051766 A1 | 4/2015 |
| WO | WO-2015066442 A1 | 5/2015 |
| WO | WO-2015070280 A1 | 5/2015 |
| WO | WO-2015073644 A1 | 5/2015 |

OTHER PUBLICATIONS

Altschul, et al. Gapped BLAST and PSI-BLAST: a new generation of protein database search programs. Nucleic Acids Research 25(17):3389-3402, 1997.

Baker, et al. BubR1 Insufficiency Causes Early Onset of Aging-Associated Phenotypes and Infertility in Mice. Genetics, vol. 36, No. 7, Jul. 2004, pp. 744-749.

Baker et al. Clearance of p16Ink4a-positive senescent cells delays ageing-associated disorders. Nature 479(7372):232-236 (2011).

Baker, et al. Early aging-associated phenotypes in Bub3/Rael haploinsufficient mice. The Journal of Cell Biology 172(4):529-540, 2006.

Bennett, et al. SP600125, An Anthrapyrazolone Inhibitor of Jun N-Terminal Kinase. PNAS, vol. 98, No. 24, 20, 2001, pp. 13681-13686.

Braun, et al. Cellular senescence limits regenerative capacity and allograft survival.J Am Soc Nephrol. Sep. 2012;23(9):1467-73. doi: 10.1681/ASN.2011100967. Epub Jul. 12, 2012.

Brouilette, et al. White Cell Telomere Length and Risk of Premature Myocardial Infarction. Arteriosclerosis, Thrombosis, and Vascular Biology: Journal of the American Heart Association 23:842-846, 2003.

Burrig, et al. The endothelium of advanced arteriosclerotic plaques in humans. Arteriosclerosis, Thrombosis, and Vascular Biology: Journal of the American Heart Association 11:1678-1689, 1991.

Campisi, et al. Cellular senescence: a link between cancer and age-related degenerative disease? Semin Cancer Biol. Dec. 2011;21(6):354-9. doi: 10.1016/j.semcancer.2011.09.001. Epub Sep. 10, 2011.

Campisi, et al. Cellular senescence: when bad things happen to good cells. Nature Reviews Molecular Cell Biology 8:729-740, 2007.

Campisi, J. Cellular senescence: putting the paradoxes in perspective. Curr Opin Genet Dev. Feb. 2011;21(1):107-12. doi: 10.1016/j.gde.2010.10.005. Epub Nov. 17, 2010.

Campisi, J. Senescent cells, tumor suppression, and organismal aging: good citizens, bad neighbors. Cell. Feb. 25, 2005;120(4):513-22.

Chang, et al. Effects of p21 Wafl/Cipl/Sdilon cellular gene expression: Implications for carcinogenesis, senescence, and age-related diseases. PNAS 97(8):4291-4296, 2000.

Chang, et al. Telomere length and replicative aging in human vascular tissues. PNAS 92(24):11190-11194, 1995.

Cheng, et al. The Nucleotide Sequence of a Human Cellular Thyroid Hormone Binding Protein Present in Endoplasmic Reticulum. The Journal of Biological Chemistry 262(23):11221-11227, 1987.

Chistiakov. How to fight with senescent cells? Geriatr Gerontol Int. Apr. 2011;11(2):233-5. doi: 10.1111/j.1447-0594.2010.00654.x.

Chung, et al. Molecular inflammation: underpinnings of aging and age-related diseases. Ageing Res Rev. Jan. 2009;8(1):18-30. doi: 10.1016/j.arr.2008.07.002. Epub Jul. 18, 2008.

Coppe, et al. Senescence-associated secretory phenotypes reveal cell-nonautonomous functions of oncogenic RAS and the p53 tumor suppressor. PLoS Biol. Dec. 2, 2008;6(12):2853-68. doi: 10.1371/journal.pbio.0060301.

Davalos, et al. p53-dependent release of Alarmin HMGB1 is a central mediator of senescent phenotypes. J Cell Biol. May 13, 2013;201(4):613-29. doi: 10.1083/jcb.201206006. Epub May 6, 2013.

Davalos, et al. Senescent cells as a source of inflammatory factors for tumor progression. Cancer Metastasis Rev. Jun. 2010;29(2):273-83. doi: 10.1007/s10555-010-9220-9.

Davies, et al. Morphology of the endothelium over atherosclerotic plaques in human coronary arteries. British Heart Journal 60:459-464, 1988.

Deursen. Clearance of senescent cells and adult aging phenotypes. Pitts. Jun. 2014. 15 pages.

Deursen, et al. Senescent cells have some nerve! Mayo Clinic. NCI. Mar. 2015. Rochester, MN. 15 pages.

Deursen, et al. Senescent cells shorten health and life span. Mayo Clinic. Berlin. Febs 2015. 30 pages.

Deursen, et al. Senescent in aging and age-related disease: from mechanism to therapy. Mayo Clinic. ICSA Conference. Jul. 2015. Santiago de Compostela. 40 pages.

Deursen. Senescent Cells as Drivers of Cancer & Aging. Mayo Clinic. NYU Dec. 2014. 55 pages.

Deursen. The role of p16+ (senescent) cells in aging. Erice. Jun. 2015. 17 pages.

Deursen. Understanding Senescence and Chromosomal Instability in Cancer and Aging. Mayo Clinic. Ohio State. Jan. 2015. 49 pages.

Di Leonardo, et al. DNA damage triggers a prolonged p53-dependent G1 arrest and long-term induction of Cipl in normal human fibroblasts. Genes Development 8:2540-2551, 1994.

Dimri, et al. A biomarker that identifies senescent human cells in culture and in aging skin in vivo. Proc Natl Acad Sci U S A. Sep. 26, 1995;92(20):9363-7.

Efeyan, et al. Induction of p53-dependent senescence by the MDM2 antagonist nutlin-3a in mouse cells of fibroblast origin. Cancer Res. Aug. 1, 2007;67(15):7350-7.

(56) References Cited

OTHER PUBLICATIONS

Eisen, et al. Macronuclear Genome Sequence of the Ciliate Tetrahymena Thermophila, a Model Eukaryote. PLoS Biol. 4(9):1620-1642, 2006.
Freund, et al. Inflammatory networks during cellular senescence: causes and consequences. Trends Mol Med. May 2010;16(5):238-46. doi: 10.1016/j.molmed.2010.03.003. Epub May 3, 2010.
Freund, et al. Lamin B1 loss is a senescence-associated biomarker. Mol Biol Cell. Jun. 2012;23(11):2066-75. doi: 10.1091/mbc.E11-10-0884. Epub Apr. 11, 2012.
Gorenne, et al. Vascular smooth muscle cell senescence in atherosclerosis. Cardiovasc Res. Oct. 1, 2006;72(1):9-17. Epub Jun. 6, 2006.
Heidebrecht, et al. Repp86: A Human Protein Associated in the Progression of Mitosis. Molecular Cancer Research 1:271-279, 2003.
Homsy, et al. Characterization of Human Skin Fibroblasts Elastase Activity. Journal of Investigative Dermatology 91:472-477, 1988.
International Preliminary Report in International Application No. PCT/US2012/043613, dated Jan. 9, 2014, 5 pages.
International search report and written opinion dated Apr. 22, 2014 for International PCT Patent Application No. PCT/US2013/072938.
International search report and written opinion dated May 6, 2015 for PCT/US2015/013376.
International search report and written opinion dated Jun. 29, 2015 for PCT/US2015/013387.
International search report and written opinion dated Aug. 13, 2013 for PCT/US2013/035023.
International Search Report and Written Opinion in International Application No. PCT/US2012/043613, dated Nov. 29, 2012, 9 pages.
International Search Report and Written Opinion received for PCT Patent Application No. PCT/US2013/035020, dated Jul. 22, 2013, 11 pages.
Invitation to pay additional fees dated Apr. 20, 2015 for PCT/US2015/013387.
Kassem, et al. Senescence-associated intrinsic mechanisms of osteoblast dysfunctions. Aging Cell. Apr. 2011;10(2):191-7. doi: 10.1111/j.1474-9726.2011.00669.x. Epub Feb. 18, 2011.
Kim, et al. SP600125, an inhibitor of Jnk pathway, reduces viability of relatively resistant cancer cells to doxorubicin. Biochem Biophys Res Commun. Sep. 25, 2009;387(3):450-5. doi: 10.1016/j.bbrc.2009.07.036. Epub Jul. 14, 2009.
Kitazono, et al. Multidrug Resistance and the Lung Resistance-Related Protein in Human Colon Carcinoma SW-620 Cells. Journal of the National Cancer Institute 91(19):1647-1653, 1999.
Kren, et al. Increased tumor cell dissemination and cellular senescence in the absence of13i-integrin function. The EMBO Journal 26:2832-2842, 2007.
Krtolica, et al. Senescent fibroblasts promote epithelial cell growth and tumorigenesis: a link between cancer and aging. Proc Natl Acad Sci U S A. Oct. 9, 2001;98(21):12072-7. Epub Oct. 2, 2001.
Kuilman, et al. The essence of senescence. Genes Develop., 2010, 24:2463-2479.
Laberge, et al. Glucocorticoids suppress selected components of the senescence-associated secretory phenotype. Aging Cell 11(4):569-578, 2012.
Le, et al. Ionizing radiation-induced long-term expression of senescence markers in mice is independent of p53 and immune status. Aging Cell. Jun. 2010;9(3):398-409. doi: 10.1111/j.1474-9726.2010.00567.x. Epub Mar. 13, 2010.
Leavitt, et al. Expression of Transfected Mutant 13-Actin Genes: Transitions toward the Stable Tumorigenic State. Molecular and Cell Biology 7(7):2467-2476, 1987.
Lessene; et al., "Structure-guided design of a selective BCL-X(L) inhibitor.", Jun. 9, 2013(6), 390-7.
Lin, et al. Identification and order of sequential mutations in 13-actin genes isolated from increasingly tumorigenic human fibroblast strains. Genetics 82(20):6995-6999, 1985.
Ludwig, et al. Monoclonal antibody therapeutics and apoptosis. Oncogene. Dec. 8, 2003;22(56):9097-106.
Martin, et al. The Role of Chondrocyte Senescence in the Pathogenesis of Osteoarthritis and in Limiting Cartilage Repair. J Bone Joint Surg Am, vol. 85, Suppl 2, Apr. 2003, pp. 106-110.
Martin-Ruiz, et al. Stochastic Variation in Telomere Shortening Rate Causes Heterogeneity of Human Fibroblast Replicative Life Span. Journal of Biological Chemistry 279(17):17826-17833, 2004.
Matsumoto, et al. Aging-associated vascular phenotype in mutant mice with low levels of BubR1. Stroke, 2007, 38:1050-1056.
Michishita, et al. 5-Bromodeoxyuridine Induces Senescence-Like Phenomena in Mammalian Cells Regardless of Cell Type or Species. Journal of Biochemistry 126(6):1052-1059, 1999.
Minamino et al., Vascular Cell Senescence: Contribution to Atherosclerosis. Journal of the American Heart Association, Circ Res. Jan. 5, 2007;100(1):15-26.
Muller, et al. Lung fibroblasts from patients with emphysema show markers of senescence in vitro. Respir Res. Feb. 21, 2006;7:32.
Office action dated Jan. 9, 2015 for U.S. Appl. No. 12/809,952.
Office action dated Apr. 7, 2015 for U.S. Appl. No. 14/125,841.
Office action dated May 30, 2014 for U.S. Appl. No. 12/809,952.
Office Action dated Aug. 31, 2016 for U.S. Appl. No. 14/750,941.
Office action dated Nov. 5, 2015 for U.S. Appl. No. 14/557,316.
Office action dated Nov. 25, 2014 for U.S. Appl. No. 13/830,790.
Patel, et al. Apigenin and cancer chemoprevention: Progress, potential and promise (Review). Int J Oncol. Jan. 2007;30(1):233-45.
Pihlajaniemi, et al. Molecular cloning of the 13-subunit of human prolyl 4-hydroxylase. This subunit and protein disulphide isomerase are products of the same gene. The EMBO Journal 6(3):643-649, 1987.
Prieur, et al. Cellular senescence in vivo: a barrier to tumorigenesis. Curr Opin Cell Biol. Apr. 2008;20(2):150-5. doi: 10.1016/j.ceb.2008.01.007. Epub Mar. 18, 2008.
Roberts, et al. Senescence in human intervertebral discs. Eur Spine J. Aug. 2006;15 Suppl 3:S312-6. Epub Jun. 14, 2006.
Rodier, et al. Persistent DNA damage signalling triggers senescence-associated inflammatory cytokine secretion. Nat Cell Biol. Aug. 2009;11(8):973-9. doi: 10.1038/ncb1909. Epub Jul. 13, 2009.
Roninson. Tumor Cell Senescence in Cancer Treatment. Cancer Research 63(11):2705-2715, 2003.
Ruela De Sousa, et al. Cytotoxicity of apigenin on leukemia cell lines: implications for prevention and therapy. Cell Death Dis. 2010;1:e19. doi: 10.1038/cddis.2009.18.
Saretzki, et al. MitoQ counteracts telomere shortening and elongates lifespan of fibroblasts under mild oxidative stress. Aging Cell 2(2):141-143, 2003.
Shangary, et al. Temporal activation of p53 by a specific MDM2 inhibitor is selectively toxic to tumors and leads to complete tumor growth inhibition. Proc Natl Acad Sci U S A. Mar. 11, 2008;105(10):3933-8. doi: 10.1073/pnas.0708917105. Epub Mar. 3, 2008.
Sharpless, et al. Telomeres, stem cells, senescence, and cancer. Journal of Clinical Investigation 113(2):160-168, 2004.
Shay, et al. Defining the molecular mechanisms of human cell immortalization. Biochimica et Biophysica Acta 1072(1):1-7, 1991.
Sis, et al. Accelerated expression of senescence associated cell cycle inhibitor p16INK4A in kidneys with glomerular disease. Kidney Int. Feb. 2007;71(3):218-26. Epub Dec. 20, 2006.
Stanley et al. Senescence and the Healing Rates of Venous Ulcers. J Vasc Surg. Jun. 2001;33(6):1206-11.
Stein, et al. Differential Roles for Cyclin-Dependent Kinase Inhibitors p21 and p16 in the Mechanisms of Senescence and Differentiation in Human Fibroblasts. Molecular and Cellular Biology /9(3):2109-2117, 1999..
Tchkonia, et al. Fat tissue, aging, and cellular senescence. Aging Cell. Oct. 2010;9(5):667-84.
Tominaga, et al. Genetics of cellular senescence. Mechanisms of Ageing and Development 123(8):927-936, 2002.
Tsuji, et al. Alveolar cell senescence exacerbates pulmonary inflammation in patients with chronic obstructive pulmonary disease. Respiration. 2010;80(1):59-70. doi: 10.1159/000268287. Epub Dec. 17, 2009.

(56) References Cited

OTHER PUBLICATIONS

Zhao; et al. Small molecule inhibitors of MDM2-p53 and MDMX-p53 interactions as new cancer therapeutics. BioDiscovery, 8. 2013, 8(4), 15 pages.
International Application No. PCT/US2008/013913 International Search Report and Written Opinion dated Jun. 18, 2009.

```
                          SEQUENCE LISTING

<160> NUMBER OF SEQ ID NOS: 35

<210> SEQ ID NO 1
    <211> LENGTH: 12
    <212> TYPE: PRT
    <213> ORGANISM: Artificial Sequence
    <220> FEATURE:
    <223> OTHER INFORMATION: Synthetic Construct

<400> SEQUENCE: 1

Gly Val Tyr His Phe Ala Pro Leu Thr Pro Thr Pro
    1               5                   10

<210> SEQ ID NO 2
    <211> LENGTH: 12
    <212> TYPE: PRT
    <213> ORGANISM: Artificial Sequence
    <220> FEATURE:
    <223> OTHER INFORMATION: Synthetic Construct

<400> SEQUENCE: 2

Ser Phe Gln Ser His Leu Ile Glu Phe Ser Phe Glu
    1               5                   10

<210> SEQ ID NO 3
    <211> LENGTH: 12
    <212> TYPE: PRT
    <213> ORGANISM: Artificial Sequence
    <220> FEATURE:
    <223> OTHER INFORMATION: Synthetic Construct

<400> SEQUENCE: 3

Ala Pro Ile Leu Lys Leu Ala Pro Leu Ile His Pro
    1               5                   10

<210> SEQ ID NO 4
    <211> LENGTH: 14
    <212> TYPE: PRT
    <213> ORGANISM: Artificial Sequence
    <220> FEATURE:
    <223> OTHER INFORMATION: Syntheitc Construct

<400> SEQUENCE: 4

Lys Phe Ala Lys Phe Ala Lys Lys Phe Ala Lys Phe Ala Lys
    1               5                   10

<210> SEQ ID NO 5
    <211> LENGTH: 16
    <212> TYPE: PRT
    <213> ORGANISM: Artificial Sequence
    <220> FEATURE:
    <223> OTHER INFORMATION: Synthetic Construct

<400> SEQUENCE: 5

Gly Val Tyr His Phe Ala Pro Leu Thr Pro Thr Pro Gly Gly Gly Cys
    1               5                   10                  15

<210> SEQ ID NO 6
    <211> LENGTH: 29
    <212> TYPE: PRT
```

```
<213> ORGANISM: Artificial Sequence
<220> FEATURE:
<223> OTHER INFORMATION: Synthetic Construct

<400> SEQUENCE: 6

Gly Val Tyr His Phe Ala Pro Leu Thr Pro Thr Pro Gly Gly Ser Lys
1               5                   10                  15

Phe Ala Lys Phe Ala Lys Lys Phe Ala Lys Phe Ala Lys
            20                  25

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Gly Val Tyr His Phe Ala Pro Leu Thr Pro Thr Pro Gly Gly Gly Cys
1               5                   10                  15

<210> SEQ ID NO 8
<211> LENGTH: 28
<212> TYPE: PRT
<213> ORGANISM: Artificial Sequence
<220> FEATURE:
<223> OTHER INFORMATION: Synthetic Construct

<400> SEQUENCE: 8

Gly Val Tyr His Phe Ala Pro Leu Thr Pro Thr Pro Gly Gly Lys Phe
1               5                   10                  15

Ala Lys Phe Ala Lys Lys Phe Ala Lys Phe Ala Lys
            20                  25

<210> SEQ ID NO 9
<211> LENGTH: 4
<212> TYPE: PRT
<213> ORGANISM: Artificial Sequence
<220> FEATURE:
<223> OTHER INFORMATION: Synthetic Construct

<400> SEQUENCE: 9

Gly Gly Gly Cys
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Construct

<400> SEQUENCE: 10

Gly Gly Gly Ser
1

<210> SEQ ID NO 11
<211> LENGTH: 375
<212> TYPE: PRT
<213> ORGANISM: Homo sapiens

<400> SEQUENCE: 11

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
```

```
            20                  25                  30
Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
 50                  55                  60

Leu Thr Leu Lys Tyr Pro Ile Glu His Gly Ile Val Thr Asn Trp Asp
 65                  70                  75                  80

Asp Met Glu Lys Ile Trp His His Thr Phe Tyr Asn Glu Leu Arg Val
                 85                  90                  95

Ala Pro Glu Glu His Pro Val Leu Leu Thr Glu Ala Pro Leu Asn Pro
                100                 105                 110

Lys Ala Asn Arg Glu Lys Met Thr Gln Ile Met Phe Glu Thr Phe Asn
            115                 120                 125

Thr Pro Ala Met Tyr Val Ala Ile Gln Ala Met Leu Ser Leu Tyr Ala
        130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
                180                 185                 190

Leu Thr Glu Arg Gly Tyr Ser Phe Thr Thr Thr Ala Glu Arg Glu Ile
            195                 200                 205

Val Arg Asp Ile Lys Glu Lys Leu Cys Tyr Val Ala Leu Asp Phe Glu
        210                 215                 220

Gln Glu Met Ala Thr Ala Ala Ser Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
                260                 265                 270

Gly Ile His Glu Thr Thr Phe Asn Ser Ile Met Lys Cys Asp Val Asp
            275                 280                 285

Ile Arg Lys Asp Leu Tyr Asp Asn Thr Val Leu Ser Gly Gly Thr Thr
        290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
                340                 345                 350

Gln Gln Met Trp Ile Ser Lys Gln Glu Tyr Asp Glu Ser Gly Pro Ser
            355                 360                 365

Ile Val His Arg Lys Cys Phe
        370                 375

<210> SEQ ID NO 12
<211> LENGTH: 360
<212> TYPE: PRT
<213> ORGANISM: Homo Sapiens

<400> SEQUENCE: 12

Met Cys Lys Ala Gly Phe Ala Gly Asp Asp Ala Pro Arg Ala Val Phe
 1               5                  10                  15
```

-continued

```
Pro Ser Ile Val Gly Arg Pro Arg His Gln Val Met Val Gly Met
             20                  25                  30

Gly Gln Lys Asp Ser Tyr Val Gly Asp Glu Ala Gln Ser Lys Arg Gly
         35                  40                  45

Ile Leu Thr Leu Lys Tyr Pro Ile Glu His Gly Ile Val Thr Asn Trp
 50                  55                  60

Asp Asp Met Glu Lys Ile Trp His His Thr Phe Tyr Asn Glu Leu Arg
 65                  70                  75                  80

Val Ala Pro Glu Glu His Pro Val Leu Leu Thr Glu Ala Pro Leu Asn
                 85                  90                  95

Pro Lys Ala Asn Leu Glu Lys Met Thr Gln Ile Met Phe Glu Thr Phe
            100                 105                 110

Asn Thr Pro Ala Met Tyr Val Ala Ile Gln Ala Val Leu Ser Leu Tyr
        115                 120                 125

Ala Ser Gly Arg Thr Thr Gly Ile Val Met Asp Ser Gly Asp Gly Val
    130                 135                 140

Thr His Thr Val Pro Ile Tyr Glu Gly Tyr Ala Leu Pro His Ala Ile
145                 150                 155                 160

Leu Arg Leu Asp Leu Ala Gly Arg Asp Leu Thr Asp Tyr Leu Met Lys
                165                 170                 175

Ile Leu Thr Glu Arg Gly Tyr Ser Phe Thr Thr Thr Ala Glu Arg Glu
            180                 185                 190

Ile Val Arg Asp Ile Lys Glu Lys Leu Cys Tyr Val Ala Leu Asp Phe
        195                 200                 205

Glu Gln Glu Met Ala Thr Ala Ala Ser Ser Ser Leu Glu Lys Ser
    210                 215                 220

Tyr Glu Leu Pro Asp Gly Gln Val Ile Thr Ile Gly Asn Glu Arg Phe
225                 230                 235                 240

Arg Cys Pro Glu Ala Leu Phe Gln Pro Ser Phe Leu Gly Met Glu Ser
                245                 250                 255

Cys Gly Ile His Glu Thr Thr Phe Asn Ser Ile Met Lys Cys Asp Val
            260                 265                 270

Asp Ile Arg Lys Asp Leu Tyr Ala Asn Thr Val Leu Ser Gly Gly Thr
        275                 280                 285

Thr Met Tyr Pro Gly Ile Ala Asp Arg Met Gln Lys Glu Ile Thr Ala
    290                 295                 300

Leu Ala Pro Ser Thr Met Lys Ile Lys Ile Ile Ala Pro Pro Glu Arg
305                 310                 315                 320

Lys Tyr Ser Val Trp Ile Gly Gly Ser Ile Leu Ala Ser Leu Ser Thr
                325                 330                 335

Phe Gln Gln Met Trp Ile Ser Lys Gln Glu Tyr Asp Glu Ser Gly Pro
            340                 345                 350

Ser Ile Val His Arg Lys Cys Phe
        355                 360

<210> SEQ ID NO 13
<211> LENGTH: 896
<212> TYPE: PRT
<213> ORGANISM: Homo Sapiens

<400> SEQUENCE: 13

Met Ala Thr Glu Glu Phe Ile Ile Arg Ile Pro Pro Tyr His Tyr Ile
1               5                   10                  15

His Val Leu Asp Gln Asn Ser Asn Val Ser Arg Val Glu Val Gly Pro
             20                  25                  30
```

```
Lys Thr Tyr Ile Arg Gln Asp Asn Glu Arg Val Leu Phe Ala Pro Met
         35                  40                  45
Arg Met Val Thr Val Pro Pro Arg His Tyr Cys Thr Val Ala Asn Pro
     50                  55                  60
Val Ser Arg Asp Ala Gln Gly Leu Val Leu Phe Asp Val Thr Gly Gln
 65                  70                  75                  80
Val Arg Leu Arg His Ala Asp Leu Glu Ile Arg Leu Ala Gln Asp Pro
                 85                  90                  95
Phe Pro Leu Tyr Pro Gly Glu Val Leu Glu Lys Asp Ile Thr Pro Leu
                100                 105                 110
Gln Val Val Leu Pro Asn Thr Ala Leu His Leu Lys Ala Leu Leu Asp
             115                 120                 125
Phe Glu Asp Lys Asp Gly Asp Lys Val Val Ala Gly Asp Glu Trp Leu
         130                 135                 140
Phe Glu Gly Pro Gly Thr Tyr Ile Pro Arg Lys Glu Val Glu Val Val
145                 150                 155                 160
Glu Ile Ile Gln Ala Thr Ile Ile Arg Gln Asn Gln Ala Leu Arg Leu
                165                 170                 175
Arg Ala Arg Lys Glu Cys Trp Asp Arg Asp Gly Lys Glu Arg Val Thr
            180                 185                 190
Gly Glu Glu Trp Leu Val Thr Thr Val Gly Ala Tyr Leu Pro Ala Val
        195                 200                 205
Phe Glu Glu Val Leu Asp Leu Val Asp Ala Val Ile Leu Thr Glu Lys
210                 215                 220
Thr Ala Leu His Leu Arg Ala Arg Arg Asn Phe Arg Asp Phe Arg Gly
225                 230                 235                 240
Val Ser Arg Arg Thr Gly Glu Glu Trp Leu Val Thr Val Gln Asp Thr
                245                 250                 255
Glu Ala His Val Pro Asp Val His Glu Glu Val Leu Gly Val Val Pro
            260                 265                 270
Ile Thr Thr Leu Gly Pro His Asn Tyr Cys Val Ile Leu Asp Pro Val
        275                 280                 285
Gly Pro Asp Gly Lys Asn Gln Leu Gly Gln Lys Arg Val Val Lys Gly
    290                 295                 300
Glu Lys Ser Phe Phe Leu Gln Pro Gly Glu Gln Leu Glu Gln Gly Ile
305                 310                 315                 320
Gln Asp Val Tyr Val Leu Ser Glu Gln Gly Leu Leu Arg Ala
                325                 330                 335
Leu Gln Pro Leu Glu Glu Gly Glu Asp Glu Glu Lys Val Ser His Gln
            340                 345                 350
Ala Gly Asp His Trp Leu Ile Arg Gly Pro Leu Glu Tyr Val Pro Ser
        355                 360                 365
Ala Lys Val Glu Val Val Glu Glu Arg Gln Ala Ile Pro Leu Asp Glu
    370                 375                 380
Asn Glu Gly Ile Tyr Val Gln Asp Val Lys Thr Gly Lys Val Arg Ala
385                 390                 395                 400
Val Ile Gly Ser Thr Tyr Met Leu Thr Gln Asp Glu Val Leu Trp Glu
                405                 410                 415
Lys Glu Leu Pro Pro Gly Val Glu Glu Leu Leu Asn Lys Gly Gln Asp
            420                 425                 430
Pro Leu Ala Asp Arg Gly Glu Lys Asp Thr Ala Lys Ser Leu Gln Pro
        435                 440                 445
```

```
Leu Ala Pro Arg Asn Lys Thr Arg Val Val Ser Tyr Arg Val Pro His
450                 455                 460
Asn Ala Ala Val Gln Val Tyr Asp Tyr Arg Glu Lys Arg Ala Arg Val
465                 470                 475                 480
Val Phe Gly Pro Glu Leu Val Ser Leu Gly Pro Glu Glu Phe Thr
                485                 490                 495
Val Leu Ser Leu Ser Ala Gly Arg Pro Lys Arg Pro His Ala Arg Arg
            500                 505                 510
Ala Leu Cys Leu Leu Leu Gly Pro Asp Phe Phe Thr Asp Val Ile Thr
            515                 520                 525
Ile Glu Thr Ala Asp His Ala Arg Leu Gln Leu Gln Leu Ala Tyr Asn
530                 535                 540
Trp His Phe Glu Val Asn Asp Arg Lys Asp Pro Gln Glu Thr Ala Lys
545                 550                 555                 560
Leu Phe Ser Val Pro Asp Phe Val Gly Asp Ala Cys Lys Ala Ile Ala
                565                 570                 575
Ser Arg Val Arg Gly Ala Val Ala Ser Val Thr Phe Asp Asp Phe His
            580                 585                 590
Lys Asn Ser Ala Arg Ile Ile Arg Thr Ala Val Phe Gly Phe Glu Thr
            595                 600                 605
Ser Glu Ala Lys Gly Pro Asp Gly Met Ala Leu Pro Arg Pro Arg Asp
610                 615                 620
Gln Ala Val Phe Pro Gln Asn Gly Leu Val Val Ser Ser Val Asp Val
625                 630                 635                 640
Gln Ser Val Glu Pro Val Asp Gln Arg Thr Arg Asp Ala Leu Gln Arg
                645                 650                 655
Ser Val Gln Leu Ala Ile Glu Ile Thr Thr Asn Ser Gln Glu Ala Ala
            660                 665                 670
Ala Lys His Glu Ala Gln Arg Leu Glu Gln Glu Ala Arg Gly Arg Leu
            675                 680                 685
Glu Arg Gln Lys Ile Leu Asp Gln Ser Glu Ala Glu Lys Ala Arg Lys
690                 695                 700
Glu Leu Leu Glu Leu Glu Ala Leu Ser Met Ala Val Glu Ser Thr Gly
705                 710                 715                 720
Thr Ala Lys Ala Glu Ala Glu Ser Arg Ala Glu Ala Ala Arg Ile Glu
                725                 730                 735
Gly Glu Gly Ser Val Leu Gln Ala Lys Leu Lys Ala Gln Ala Leu Ala
            740                 745                 750
Ile Glu Thr Glu Ala Glu Leu Gln Arg Val Gln Lys Val Arg Glu Leu
            755                 760                 765
Glu Leu Val Tyr Ala Arg Ala Gln Leu Glu Leu Glu Val Ser Lys Ala
770                 775                 780
Gln Gln Leu Ala Glu Val Glu Val Lys Lys Phe Lys Gln Met Thr Glu
785                 790                 795                 800
Ala Ile Gly Pro Ser Thr Ile Arg Asp Leu Ala Val Ala Gly Pro Glu
                805                 810                 815
Met Gln Val Lys Leu Leu Gln Ser Leu Gly Leu Lys Ser Thr Leu Ile
            820                 825                 830
Thr Asp Gly Ser Thr Pro Ile Asn Leu Phe Asn Thr Ala Phe Gly Leu
            835                 840                 845
Leu Gly Met Gly Pro Glu Gly Gln Pro Leu Gly Arg Arg Val Pro Val
850                 855                 860
Ala Gln Pro Trp Gly Gly Asp Ile Pro Pro Val Cys Ser Gly Pro Ser
```

```
            865                 870                 875                 880
Ser Ser Trp Arg Gln Pro Arg Gly Ala Cys Thr Ala Leu Thr Pro Asp
                885                 890                 895

<210> SEQ ID NO 14
<211> LENGTH: 893
<212> TYPE: PRT
<213> ORGANISM: Homo Sapiens

<400> SEQUENCE: 14

Met Ala Thr Glu Glu Phe Ile Ile Arg Ile Pro Tyr His Tyr Ile
1               5                   10                  15

His Val Leu Asp Gln Asn Ser Asn Val Ser Arg Val Glu Val Gly Pro
                20                  25                  30

Lys Thr Tyr Ile Arg Gln Asp Asn Glu Arg Val Leu Phe Ala Pro Met
                35                  40                  45

Arg Met Val Thr Val Pro Pro Arg His Tyr Cys Thr Val Ala Asn Pro
        50                  55                  60

Val Ser Arg Asp Ala Gln Gly Leu Val Leu Phe Asp Val Thr Gly Gln
65              70                  75                  80

Val Arg Leu Arg His Ala Asp Leu Glu Ile Arg Leu Ala Gln Asp Pro
                85                  90                  95

Phe Pro Leu Tyr Pro Gly Glu Val Leu Glu Lys Asp Ile Thr Pro Leu
            100                 105                 110

Gln Val Val Leu Pro Asn Thr Ala Leu His Leu Lys Ala Leu Leu Asp
            115                 120                 125

Phe Glu Asp Lys Asp Gly Asp Lys Val Val Ala Gly Asp Glu Trp Leu
130                 135                 140

Phe Glu Gly Pro Gly Thr Tyr Ile Pro Arg Lys Glu Val Glu Val Val
145                 150                 155                 160

Glu Ile Ile Gln Ala Thr Ile Ile Arg Gln Asn Gln Ala Leu Arg Leu
                165                 170                 175

Arg Ala Arg Lys Glu Cys Trp Asp Arg Asp Gly Lys Glu Arg Val Thr
            180                 185                 190

Gly Glu Glu Trp Leu Val Thr Thr Val Gly Ala Tyr Leu Pro Ala Val
            195                 200                 205

Phe Glu Glu Val Leu Asp Leu Val Asp Ala Val Ile Leu Thr Glu Lys
        210                 215                 220

Thr Ala Leu His Leu Arg Ala Arg Arg Asn Phe Arg Asp Phe Arg Gly
225             230                 235                 240

Val Ser Arg Arg Thr Gly Glu Glu Trp Leu Val Thr Val Gln Asp Thr
                245                 250                 255

Glu Ala His Val Pro Asp Val His Glu Glu Val Leu Gly Val Val Pro
            260                 265                 270

Ile Thr Thr Leu Gly Pro His Asn Tyr Cys Val Ile Leu Asp Pro Val
        275                 280                 285

Gly Pro Asp Gly Lys Asn Gln Leu Gly Gln Lys Arg Val Val Lys Gly
290                 295                 300

Glu Lys Ser Phe Phe Leu Gln Pro Gly Glu Gln Leu Glu Gln Gly Ile
305                 310                 315                 320

Gln Asp Val Tyr Val Leu Ser Glu Gln Gly Leu Leu Arg Ala
                325                 330                 335

Leu Gln Pro Leu Glu Glu Gly Glu Asp Glu Glu Lys Val Ser His Gln
            340                 345                 350
```

-continued

```
Ala Gly Asp His Trp Leu Ile Arg Gly Pro Leu Glu Tyr Val Pro Ser
            355                 360                 365

Ala Lys Val Glu Val Val Glu Glu Arg Gln Ala Ile Pro Leu Asp Glu
    370                 375                 380

Asn Glu Gly Ile Tyr Val Gln Asp Val Lys Thr Gly Lys Val Arg Ala
385                 390                 395                 400

Val Ile Gly Ser Thr Tyr Met Leu Thr Gln Asp Glu Val Leu Trp Glu
                405                 410                 415

Lys Glu Leu Pro Pro Gly Val Glu Leu Leu Asn Lys Gly Gln Asp
                420                 425                 430

Pro Leu Ala Asp Arg Gly Glu Lys Asp Thr Ala Lys Ser Leu Gln Pro
            435                 440                 445

Leu Ala Pro Arg Asn Lys Thr Arg Val Val Ser Tyr Arg Val Pro His
    450                 455                 460

Asn Ala Ala Val Gln Val Tyr Asp Tyr Arg Glu Lys Arg Ala Arg Val
465                 470                 475                 480

Val Phe Gly Pro Glu Leu Val Ser Leu Gly Pro Glu Glu Gln Phe Thr
                485                 490                 495

Val Leu Ser Leu Ser Ala Gly Arg Pro Lys Arg Pro His Ala Arg Arg
            500                 505                 510

Ala Leu Cys Leu Leu Leu Gly Pro Asp Phe Phe Thr Asp Val Ile Thr
    515                 520                 525

Ile Glu Thr Ala Asp His Ala Arg Leu Gln Leu Gln Leu Ala Tyr Asn
530                 535                 540

Trp His Phe Glu Val Asn Asp Arg Lys Asp Pro Gln Glu Thr Ala Lys
545                 550                 555                 560

Leu Phe Ser Val Pro Asp Phe Val Gly Asp Ala Cys Lys Ala Ile Ala
                565                 570                 575

Ser Arg Val Arg Gly Ala Val Ala Ser Val Thr Phe Asp Asp Phe His
            580                 585                 590

Lys Asn Ser Ala Arg Ile Ile Arg Thr Ala Val Phe Gly Phe Glu Thr
    595                 600                 605

Ser Glu Ala Lys Gly Pro Asp Gly Met Ala Leu Pro Arg Pro Arg Asp
610                 615                 620

Gln Ala Val Phe Pro Gln Asn Gly Leu Val Val Ser Ser Val Asp Val
625                 630                 635                 640

Gln Ser Val Glu Pro Val Asp Gln Arg Thr Arg Asp Ala Leu Gln Arg
                645                 650                 655

Ser Val Gln Leu Ala Ile Glu Ile Thr Thr Asn Ser Gln Glu Ala Ala
            660                 665                 670

Ala Lys His Glu Ala Gln Arg Leu Glu Gln Glu Ala Arg Gly Arg Leu
    675                 680                 685

Glu Arg Gln Lys Ile Leu Asp Gln Ser Glu Ala Glu Lys Ala Arg Lys
690                 695                 700

Glu Leu Leu Glu Leu Glu Ala Leu Ser Met Ala Val Glu Ser Thr Gly
705                 710                 715                 720

Thr Ala Lys Ala Glu Ala Glu Ser Arg Ala Glu Ala Ala Arg Ile Glu
                725                 730                 735

Gly Glu Gly Ser Val Leu Gln Ala Lys Leu Lys Ala Gln Ala Leu Ala
            740                 745                 750

Ile Glu Thr Glu Ala Glu Leu Gln Arg Val Gln Lys Val Arg Glu Leu
    755                 760                 765

Glu Leu Val Tyr Ala Arg Ala Gln Leu Glu Leu Glu Val Ser Lys Ala
```

```
              770                 775                 780
Gln Gln Leu Ala Glu Val Glu Val Lys Lys Phe Lys Gln Met Thr Glu
785                 790                 795                 800

Ala Ile Gly Pro Ser Thr Ile Arg Asp Leu Ala Val Ala Gly Pro Glu
                805                 810                 815

Met Gln Val Lys Leu Leu Gln Ser Leu Gly Leu Lys Ser Thr Leu Ile
                820                 825                 830

Thr Asp Gly Ser Thr Pro Ile Asn Leu Phe Asn Thr Ala Phe Gly Leu
                835                 840                 845

Leu Gly Met Gly Pro Glu Gly Gln Pro Leu Gly Arg Arg Val Ala Ser
850                 855                 860

Gly Pro Ser Pro Gly Glu Gly Ile Ser Pro Gln Ser Ala Gln Ala Pro
865                 870                 875                 880

Gln Ala Pro Gly Asp Asn His Val Val Pro Val Leu Arg
                885                 890

<210> SEQ ID NO 15
<211> LENGTH: 508
<212> TYPE: PRT
<213> ORGANISM: Homo Sapiens

<400> SEQUENCE: 15

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
                20                  25                  30

Asn Phe Ala Glu Ala Leu Ala Ala His Lys Tyr Leu Leu Val Glu Phe
            35                  40                  45

Tyr Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65              70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Arg Asp Gly Ala
    130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
    210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255
```

Ile Leu Leu Phe Leu Pro Lys Ser Val Ser Asp Tyr Asp Gly Lys Leu
                260                 265                 270

Ser Asn Phe Lys Thr Ala Ala Glu Ser Phe Lys Gly Lys Ile Leu Phe
            275                 280                 285

Ile Phe Ile Asp Ser Asp His Thr Asp Asn Gln Arg Ile Leu Glu Phe
290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Leu Thr Ala
                325                 330                 335

Glu Arg Ile Thr Glu Phe Cys His Arg Phe Leu Glu Gly Lys Ile Lys
            340                 345                 350

Pro His Leu Met Ser Gln Glu Arg Ala Gly Asp Trp Asp Lys Gln Pro
                355                 360                 365

Val Lys Val Pro Val Gly Lys Asn Phe Glu Asp Val Ala Phe Asp Glu
    370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
                435                 440                 445

Ser Ala Asp Arg Thr Val Ile Asp Tyr Asn Gly Glu Arg Thr Leu Asp
450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Pro Asp Met Glu
                485                 490                 495

Glu Asp Asp Asp Gln Lys Ala Val Lys Asp Glu Leu
                500                 505

<210> SEQ ID NO 16
<211> LENGTH: 508
<212> TYPE: PRT
<213> ORGANISM: Homo sapiens

<400> SEQUENCE: 16

Met Leu Arg Arg Ala Leu Leu Cys Leu Ala Val Ala Ala Leu Val Arg
1               5                   10                  15

Ala Asp Ala Pro Glu Glu Glu Asp His Val Leu Val Leu Arg Lys Ser
                20                  25                  30

Asn Phe Ala Glu Ala Leu Ala Ala His Lys Tyr Leu Leu Val Glu Phe
            35                  40                  45

Tyr Ala Pro Trp Cys Gly His Cys Lys Ala Leu Ala Pro Glu Tyr Ala
        50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
                100                 105                 110

Pro Lys Glu Tyr Thr Ala Gly Arg Glu Ala Asp Asp Ile Val Asn Trp
            115                 120                 125

Leu Lys Lys Arg Thr Gly Pro Ala Ala Thr Thr Leu Pro Asp Gly Ala
130                 135                 140

Ala Ala Glu Ser Leu Val Glu Ser Ser Glu Val Ala Val Ile Gly Phe
145                 150                 155                 160

Phe Lys Asp Val Glu Ser Asp Ser Ala Lys Gln Phe Leu Gln Ala Ala
            165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Val Thr Lys Glu Asn
210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335

Glu Arg Ile Thr Glu Phe Cys His Arg Phe Leu Glu Gly Lys Ile Lys
            340                 345                 350

Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Ser Phe Pro Thr Leu Lys Phe Phe Pro Ala
        435                 440                 445

Ser Ala Asp Arg Thr Val Ile Asp Tyr Asn Gly Glu Arg Thr Leu Asp
450                 455                 460

Gly Phe Lys Lys Phe Leu Glu Ser Gly Gly Gln Asp Gly Ala Gly Asp
465                 470                 475                 480

Asp Asp Asp Leu Glu Asp Leu Glu Glu Ala Glu Pro Asp Met Glu
                485                 490                 495

Glu Asp Asp Asp Gln Lys Ala Val Lys Asp Glu Leu
            500                 505

<210> SEQ ID NO 17
<211> LENGTH: 120
<212> TYPE: PRT
<213> ORGANISM: Homo Sapiens

<400> SEQUENCE: 17

```
Asp Ala Pro Glu Glu Asp His Val Leu Val Leu Arg Lys Ser Asn
1               5                   10                  15

Phe Ala Glu Ala Leu Ala His Lys Tyr Leu Leu Val Glu Phe Tyr
            20                  25                  30

Ala Pro Trp Cys Gly His Cys Lys Ala Leu Ala Pro Glu Tyr Ala Lys
        35                  40                  45

Ala Ala Gly Lys Leu Lys Ala Glu Gly Ser Glu Ile Arg Leu Ala Lys
    50                  55                  60

Val Asp Ala Thr Glu Glu Ser Asp Leu Ala Gln Gln Tyr Gly Val Arg
65                  70                  75                  80

Gly Tyr Pro Thr Ile Lys Phe Phe Arg Asn Gly Asp Thr Ala Ser Pro
                85                  90                  95

Lys Glu Tyr Thr Ala Gly Arg Glu Ala Asp Asp Ile Val Asn Trp Leu
            100                 105                 110

Lys Lys Arg Thr Gly Pro Ala Ala
        115                 120
```

<210> SEQ ID NO 18
<211> LENGTH: 255
<212> TYPE: PRT
<213> ORGANISM: Homo Sapiens

<400> SEQUENCE: 18

```
Met Ala Glu Leu Arg Val Leu Val Ala Val Lys Arg Val Ile Asp Tyr
1               5                   10                  15

Ala Val Lys Ile Arg Val Lys Pro Asp Arg Thr Gly Val Val Thr Asp
            20                  25                  30

Gly Val Lys His Ser Met Asn Pro Phe Cys Glu Ile Ala Val Glu Glu
        35                  40                  45

Ala Val Arg Leu Lys Glu Lys Lys Leu Val Lys Glu Val Ile Ala Val
    50                  55                  60

Ser Cys Gly Pro Ala Gln Cys Gln Glu Thr Ile Arg Thr Ala Leu Ala
65                  70                  75                  80

Met Gly Ala Asp Arg Gly Ile His Val Glu Val Pro Pro Ala Glu Ala
                85                  90                  95

Glu Arg Leu Gly Pro Leu Gln Val Ala Arg Val Leu Ala Lys Leu Ala
            100                 105                 110

Glu Lys Glu Lys Val Asp Leu Val Leu Leu Gly Lys Gln Ala Ile Asp
        115                 120                 125

Asp Asp Cys Asn Gln Thr Gly Gln Met Thr Ala Gly Phe Leu Asp Trp
    130                 135                 140

Pro Gln Gly Thr Phe Ala Ser Gln Val Thr Leu Glu Gly Asp Lys Leu
145                 150                 155                 160

Lys Val Glu Arg Glu Ile Asp Gly Gly Leu Glu Thr Leu Arg Leu Lys
                165                 170                 175

Leu Pro Ala Val Val Thr Ala Asp Leu Arg Leu Asn Glu Pro Arg Tyr
            180                 185                 190

Ala Thr Leu Pro Asn Ile Met Lys Ala Lys Lys Lys Ile Glu Val
        195                 200                 205

Ile Lys Pro Gly Asp Leu Gly Val Asp Leu Thr Ser Lys Leu Ser Val
    210                 215                 220

Ile Ser Val Glu Asp Pro Pro Gln Arg Thr Ala Gly Val Lys Val Glu
225                 230                 235                 240
```

```
Thr Thr Glu Asp Leu Val Ala Lys Leu Lys Glu Ile Gly Arg Ile
            245                 250                 255
```

<210> SEQ ID NO 19
<211> LENGTH: 553
<212> TYPE: PRT
<213> ORGANISM: Homo sapiens

<400> SEQUENCE: 19

```
Met Leu Ser Val Arg Val Ala Ala Val Val Arg Ala Leu Pro Arg
1               5                   10                  15

Arg Ala Gly Leu Val Ser Arg Asn Ala Leu Gly Ser Ser Phe Ile Ala
                20                  25                  30

Ala Arg Asn Phe His Ala Ser Asn Thr His Leu Gln Lys Thr Gly Thr
                35                  40                  45

Ala Glu Met Ser Ser Ile Leu Glu Glu Arg Ile Leu Gly Ala Asp Thr
            50                  55                  60

Ser Val Asp Leu Glu Glu Thr Gly Arg Val Leu Ser Ile Gly Asp Gly
65                  70                  75                  80

Ile Ala Arg Val His Gly Leu Arg Asn Val Gln Ala Glu Glu Met Val
                    85                  90                  95

Glu Phe Ser Ser Gly Leu Lys Gly Met Ser Leu Asn Leu Glu Pro Asp
                100                 105                 110

Asn Val Gly Val Val Val Phe Gly Asn Asp Lys Leu Ile Lys Glu Gly
                115                 120                 125

Asp Ile Val Lys Arg Thr Gly Ala Ile Val Asp Val Pro Val Gly Glu
            130                 135                 140

Glu Leu Leu Gly Arg Val Val Asp Ala Leu Gly Asn Ala Ile Asp Gly
145                 150                 155                 160

Lys Gly Pro Ile Gly Ser Lys Thr Arg Arg Arg Val Gly Leu Lys Ala
                    165                 170                 175

Pro Gly Ile Ile Pro Arg Ile Ser Val Arg Glu Pro Met Gln Thr Gly
                180                 185                 190

Ile Lys Ala Val Asp Ser Leu Val Pro Ile Gly Arg Gly Gln Arg Glu
                195                 200                 205

Leu Ile Ile Gly Asp Arg Gln Thr Gly Lys Thr Ser Ile Ala Ile Asp
            210                 215                 220

Thr Ile Ile Asn Gln Lys Arg Phe Asn Asp Gly Ser Asp Glu Lys Lys
225                 230                 235                 240

Lys Leu Tyr Cys Ile Tyr Val Ala Ile Gly Gln Lys Arg Ser Thr Val
                    245                 250                 255

Ala Gln Leu Val Lys Arg Leu Thr Asp Ala Asp Ala Met Lys Tyr Thr
                260                 265                 270

Ile Val Val Ser Ala Thr Ala Ser Asp Ala Ala Pro Leu Gln Tyr Leu
                275                 280                 285

Ala Pro Tyr Ser Gly Cys Ser Met Gly Glu Tyr Phe Arg Asp Asn Gly
            290                 295                 300

Lys His Ala Leu Ile Ile Tyr Asp Asp Leu Ser Lys Gln Ala Val Ala
305                 310                 315                 320

Tyr Arg Gln Met Ser Leu Leu Leu Arg Arg Pro Pro Gly Arg Glu Ala
                    325                 330                 335

Tyr Pro Gly Asp Val Phe Tyr Leu His Ser Arg Leu Leu Glu Arg Ala
                340                 345                 350

Ala Lys Met Asn Asp Ala Phe Gly Gly Gly Ser Leu Thr Ala Leu Pro
                355                 360                 365
```

```
Val Ile Glu Thr Gln Ala Gly Asp Val Ser Ala Tyr Ile Pro Thr Asn
            370                 375                 380

Val Ile Ser Ile Thr Asp Gly Gln Ile Phe Leu Glu Thr Glu Leu Phe
385                 390                 395                 400

Tyr Lys Gly Ile Arg Pro Ala Ile Asn Val Gly Leu Ser Val Ser Arg
                405                 410                 415

Val Gly Ser Ala Ala Gln Thr Arg Ala Met Lys Gln Val Ala Gly Thr
                420                 425                 430

Met Lys Leu Glu Leu Ala Gln Tyr Arg Glu Val Ala Ala Phe Ala Gln
            435                 440                 445

Phe Gly Ser Asp Leu Asp Ala Ala Thr Gln Gln Leu Leu Ser Arg Gly
            450                 455                 460

Val Arg Leu Thr Glu Leu Leu Lys Gln Gly Gln Tyr Ser Pro Met Ala
465                 470                 475                 480

Ile Glu Glu Gln Val Ala Val Ile Tyr Ala Gly Val Arg Gly Tyr Leu
                485                 490                 495

Asp Lys Leu Glu Pro Ser Lys Ile Thr Lys Phe Glu Asn Ala Phe Leu
            500                 505                 510

Ser His Val Val Ser Gln His Gln Ala Leu Leu Gly Thr Ile Arg Ala
            515                 520                 525

Asp Gly Lys Ile Ser Glu Gln Ser Asp Ala Lys Leu Lys Glu Ile Val
            530                 535                 540

Thr Asn Phe Leu Ala Gly Phe Glu Ala
545                 550

<210> SEQ ID NO 20
<211> LENGTH: 508
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa can be any naturally occurring amino acid

<400> SEQUENCE: 20

Met Leu Arg Arg Ala Leu Leu Cys Leu Pro Trp Xaa Ala Leu Val Arg
1               5                   10                  15

Ala Asp Ala Pro Glu Glu Glu Asp His Val Leu Val Leu Arg Lys Ser
            20                  25                  30

Asn Phe Ala Glu Ala Leu Ala Ala His Lys Tyr Pro Pro Val Glu Phe
        35                  40                  45

His Ala Pro Trp Cys Gly His Cys Lys Ala Leu Ala Pro Glu Tyr Ala
    50                  55                  60

Lys Ala Ala Gly Lys Leu Lys Ala Glu Gly Ser Glu Ile Arg Leu Ala
65                  70                  75                  80

Lys Val Asp Ala Thr Glu Glu Ser Asp Leu Ala Gln Gln Tyr Gly Val
                85                  90                  95

Arg Gly Tyr Pro Thr Ile Lys Phe Phe Arg Asn Gly Asp Thr Ala Ser
            100                 105                 110

Pro Lys Glu Tyr Thr Ala Gly Arg Glu Ala Asp Asp Ile Val Asn Trp
        115                 120                 125

Leu Lys Lys Arg Thr Gly Pro Ala Ala Thr Thr Leu Pro Asp Gly Ala
    130                 135                 140

Ala Ala Glu Ser Leu Val Glu Ser Ser Glu Val Ala Val Ile Gly Phe
145                 150                 155                 160
```

```
Phe Lys Asp Val Glu Ser Asp Ser Ala Lys Gln Phe Leu Gln Ala Ala
                165                 170                 175

Glu Ala Ile Asp Asp Ile Pro Phe Gly Ile Thr Ser Asn Ser Asp Val
            180                 185                 190

Phe Ser Lys Tyr Gln Leu Asp Lys Asp Gly Val Val Leu Phe Lys Lys
        195                 200                 205

Phe Asp Glu Gly Arg Asn Asn Phe Glu Gly Glu Val Thr Lys Glu Asn
    210                 215                 220

Leu Leu Asp Phe Ile Lys His Asn Gln Leu Pro Leu Val Ile Glu Phe
225                 230                 235                 240

Thr Glu Gln Thr Ala Pro Lys Ile Phe Gly Gly Glu Ile Lys Thr His
                245                 250                 255

Ile Leu Leu Phe Leu Pro Lys Ser Val Ser Asp Tyr Asp Gly Lys Leu
            260                 265                 270

Ser Asn Phe Lys Thr Ala Ala Glu Ser Phe Lys Gly Lys Ile Leu Phe
        275                 280                 285

Ile Phe Ile Asp Ser Asp His Thr Asp Asn Gln Arg Ile Leu Glu Phe
    290                 295                 300

Phe Gly Leu Lys Lys Glu Glu Cys Pro Ala Val Arg Leu Ile Thr Leu
305                 310                 315                 320

Glu Glu Glu Met Thr Lys Tyr Lys Pro Glu Ser Glu Glu Leu Thr Ala
                325                 330                 335

Glu Arg Ile Thr Glu Phe Cys His Arg Phe Leu Glu Gly Lys Ile Lys
            340                 345                 350

Pro His Leu Met Ser Gln Glu Leu Pro Glu Asp Trp Asp Lys Gln Pro
        355                 360                 365

Val Lys Val Leu Val Gly Lys Asn Phe Glu Asp Val Ala Phe Asp Glu
    370                 375                 380

Lys Lys Asn Val Phe Val Glu Phe Tyr Ala Pro Trp Cys Gly His Cys
385                 390                 395                 400

Lys Gln Leu Ala Pro Ile Trp Asp Lys Leu Gly Glu Thr Tyr Lys Asp
                405                 410                 415

His Glu Asn Ile Val Ile Ala Lys Met Asp Ser Thr Ala Asn Glu Val
            420                 425                 430

Glu Ala Val Lys Val His Gly Phe Pro Thr Leu Gly Phe Phe Pro Ala
        435                 440                 445

Ser Ala Asp Arg Thr Val Ile Asp Tyr Asn Gly Glu Arg Thr Leu Asp
    450                 455                 460

Gly Phe Lys Lys Phe Leu Glu Ser Gly Gly Gln Asp Gly Ala Gly Asp
465                 470                 475                 480

Val Asp Asp Leu Glu Asp Leu Glu Glu Ala Glu Glu Pro Asp Met Glu
                485                 490                 495

Glu Asp Asp Asp Gln Lys Ala Val Lys Asp Glu Leu
            500                 505

<210> SEQ ID NO 21
<211> LENGTH: 255
<212> TYPE: PRT
<213> ORGANISM: Homo sapiens

<400> SEQUENCE: 21

Met Ala Glu Leu Arg Val Leu Ala Val Lys Arg Val Ile Asp Tyr
1               5                   10                  15

Ala Val Lys Ile Arg Val Lys Pro Asp Arg Thr Gly Val Val Thr Asp
            20                  25                  30
```

```
Gly Val Lys His Ser Met Asn Pro Phe Cys Glu Ile Ala Val Glu Glu
            35                  40                  45

Ala Val Arg Leu Lys Glu Lys Lys Leu Val Lys Glu Val Ile Ala Val
 50                  55                  60

Ser Cys Gly Pro Ala Gln Cys Gln Glu Thr Ile Arg Thr Ala Leu Ala
 65                  70                  75                  80

Met Gly Ala Asp Arg Gly Ile His Val Glu Val Pro Pro Ala Glu Ala
                 85                  90                  95

Glu Arg Leu Gly Pro Leu Gln Val Ala Arg Val Leu Ala Lys Leu Ala
            100                 105                 110

Glu Lys Glu Lys Val Asp Leu Val Leu Leu Gly Lys Gln Ala Ile Tyr
        115                 120                 125

Asp Asp Cys Asn Gln Thr Gly Gln Met Thr Ala Gly Phe Leu Asp Trp
130                 135                 140

Pro Gln Gly Thr Phe Ala Ser Gln Val Met Leu Glu Gly Asp Lys Leu
145                 150                 155                 160

Lys Val Glu Arg Glu Ile Asp Gly Gly Leu Glu Thr Leu Arg Leu Lys
                165                 170                 175

Leu Pro Ala Val Val Thr Ala Asp Leu Arg Leu Asn Glu Pro Arg Tyr
            180                 185                 190

Ala Thr Leu Pro Asn Ile Met Lys Ala Lys Lys Lys Ile Glu Val
        195                 200                 205

Ile Lys Pro Gly Asp Leu Gly Val Asp Leu Thr Ser Lys Leu Ser Val
210                 215                 220

Ile Ser Val Glu Asp Pro Pro Gln Arg Thr Ala Gly Val Lys Val Glu
225                 230                 235                 240

Thr Thr Glu Asp Leu Val Ala Lys Leu Lys Glu Ile Gly Arg Ile
                245                 250                 255

<210> SEQ ID NO 22
<211> LENGTH: 503
<212> TYPE: PRT
<213> ORGANISM: Homo sapiens

<400> SEQUENCE: 22

Met Ser Ser Ile Leu Glu Glu Arg Ile Leu Gly Ala Asp Thr Ser Val
1               5                   10                  15

Asp Leu Glu Glu Thr Gly Arg Val Leu Ser Ile Gly Asp Gly Ile Ala
            20                  25                  30

Arg Val His Gly Leu Arg Asn Val Gln Ala Glu Glu Met Val Glu Phe
        35                  40                  45

Ser Ser Gly Leu Lys Gly Met Ser Leu Asn Leu Glu Pro Asp Asn Val
 50                  55                  60

Gly Val Val Val Phe Gly Asn Asp Lys Leu Ile Lys Glu Gly Asp Ile
 65                  70                  75                  80

Val Lys Arg Thr Gly Ala Ile Val Asp Val Pro Val Gly Glu Glu Leu
                85                  90                  95

Leu Gly Arg Val Val Asp Ala Leu Gly Asn Ala Ile Asp Gly Lys Gly
            100                 105                 110

Pro Ile Gly Ser Lys Thr Arg Arg Arg Val Gly Leu Lys Ala Pro Gly
        115                 120                 125

Ile Ile Pro Arg Ile Ser Val Arg Glu Pro Met Gln Thr Gly Ile Lys
130                 135                 140

Ala Val Asp Ser Leu Val Pro Ile Gly Arg Gly Gln Arg Glu Leu Ile
```

```
            145                 150                 155                 160
    Ile Gly Asp Arg Gln Thr Gly Lys Thr Ser Ile Ala Ile Asp Thr Ile
                    165                 170                 175

Ile Asn Gln Lys Arg Phe Asn Asp Gly Ser Asp Glu Lys Lys Lys Leu
                    180                 185                 190

Tyr Cys Ile Tyr Val Ala Ile Gly Gln Lys Arg Ser Thr Val Ala Gln
                    195                 200                 205

Leu Val Lys Arg Leu Thr Asp Ala Asp Ala Met Lys Tyr Thr Ile Val
    210                 215                 220

Val Ser Ala Thr Ala Ser Asp Ala Ala Pro Leu Gln Tyr Leu Ala Pro
    225                 230                 235                 240

Tyr Ser Gly Cys Ser Met Gly Glu Tyr Phe Arg Asp Asn Gly Lys His
                    245                 250                 255

Ala Leu Ile Ile Tyr Asp Asp Leu Ser Lys Gln Ala Val Ala Tyr Arg
                    260                 265                 270

Gln Met Ser Leu Leu Leu Arg Arg Pro Pro Gly Arg Glu Ala Tyr Pro
                    275                 280                 285

Gly Asp Val Phe Tyr Leu His Ser Arg Leu Leu Glu Arg Ala Ala Lys
    290                 295                 300

Met Asn Asp Ala Phe Gly Gly Gly Ser Leu Thr Ala Leu Pro Val Ile
    305                 310                 315                 320

Glu Thr Gln Ala Gly Asp Val Ser Ala Tyr Ile Pro Thr Asn Val Ile
                    325                 330                 335

Ser Ile Thr Asp Gly Gln Ile Phe Leu Glu Thr Glu Leu Phe Tyr Lys
                    340                 345                 350

Gly Ile Arg Pro Ala Ile Asn Val Gly Leu Ser Val Ser Arg Val Gly
                    355                 360                 365

Ser Ala Ala Gln Thr Arg Ala Met Lys Gln Val Ala Gly Thr Met Lys
                    370                 375                 380

Leu Glu Leu Ala Gln Tyr Arg Glu Val Ala Ala Phe Ala Gln Phe Gly
    385                 390                 395                 400

Ser Asp Leu Asp Ala Ala Thr Gln Gln Leu Leu Ser Arg Gly Val Arg
                    405                 410                 415

Leu Thr Glu Leu Leu Lys Gln Gly Gln Tyr Ser Pro Met Ala Ile Glu
                    420                 425                 430

Glu Gln Val Ala Val Ile Tyr Ala Gly Val Arg Gly Tyr Leu Asp Lys
                    435                 440                 445

Leu Glu Pro Ser Lys Ile Thr Lys Phe Glu Asn Ala Phe Leu Ser His
                    450                 455                 460

Val Val Ser Gln His Gln Ala Leu Leu Gly Thr Ile Arg Ala Asp Gly
    465                 470                 475                 480

Lys Ile Ser Glu Gln Ser Asp Ala Lys Leu Lys Glu Ile Val Thr Asn
                    485                 490                 495

Phe Leu Ala Gly Phe Glu Ala
                    500

<210> SEQ ID NO 23
<211> LENGTH: 339
<212> TYPE: PRT
<213> ORGANISM: Homo sapiens

<400> SEQUENCE: 23

Met Trp Gln Leu Trp Ala Ser Leu Cys Cys Leu Leu Val Leu Ala Asn
1               5                   10                  15
```

```
Ala Arg Ser Arg Pro Ser Phe His Pro Leu Ser Asp Glu Leu Val Asn
            20                  25                  30
Tyr Val Asn Lys Arg Asn Thr Thr Trp Gln Ala Gly His Asn Phe Tyr
        35                  40                  45
Asn Val Asp Met Ser Tyr Leu Lys Arg Leu Cys Gly Thr Phe Leu Gly
    50                  55                  60
Gly Pro Lys Pro Pro Gln Arg Val Met Phe Thr Glu Asp Leu Lys Leu
65                  70                  75                  80
Pro Ala Ser Phe Asp Ala Arg Glu Gln Trp Pro Gln Cys Pro Thr Ile
                85                  90                  95
Lys Glu Ile Arg Asp Gln Gly Ser Cys Gly Ser Cys Trp Ala Phe Gly
            100                 105                 110
Ala Val Glu Ala Ile Ser Asp Arg Ile Cys Ile His Thr Asn Ala His
        115                 120                 125
Val Ser Val Glu Val Ser Ala Glu Asp Leu Leu Thr Cys Cys Gly Ser
    130                 135                 140
Met Cys Gly Asp Gly Cys Asn Gly Gly Tyr Pro Ala Glu Ala Trp Asn
145                 150                 155                 160
Phe Trp Thr Arg Lys Gly Leu Val Ser Gly Gly Leu Tyr Glu Ser His
                165                 170                 175
Val Gly Cys Arg Pro Tyr Ser Ile Pro Pro Cys Glu His His Val Asn
            180                 185                 190
Gly Ser Arg Pro Pro Cys Thr Gly Glu Gly Asp Thr Pro Lys Cys Ser
        195                 200                 205
Lys Ile Cys Glu Pro Gly Tyr Ser Pro Thr Tyr Lys Gln Asp Lys His
    210                 215                 220
Tyr Gly Tyr Asn Ser Tyr Ser Val Ser Asn Ser Glu Lys Asp Ile Met
225                 230                 235                 240
Ala Glu Ile Tyr Lys Asn Gly Pro Val Glu Gly Ala Phe Ser Val Tyr
                245                 250                 255
Ser Asp Phe Leu Leu Tyr Lys Ser Gly Val Tyr Gln His Val Thr Gly
            260                 265                 270
Glu Met Met Gly Gly His Ala Ile Arg Ile Leu Gly Trp Gly Val Glu
        275                 280                 285
Asn Gly Thr Pro Tyr Trp Leu Val Ala Asn Ser Trp Asn Thr Asp Trp
    290                 295                 300
Gly Asp Asn Gly Phe Phe Lys Ile Leu Arg Gly Gln Asp His Cys Gly
305                 310                 315                 320
Ile Glu Ser Glu Val Val Ala Gly Ile Pro Arg Thr Asp Gln Tyr Trp
                325                 330                 335
Glu Lys Ile

<210> SEQ ID NO 24
<211> LENGTH: 10
<212> TYPE: PRT
<213> ORGANISM: Artificial sequence
<220> FEATURE:
<223> OTHER INFORMATION: Synthetic construct

<400> SEQUENCE: 24

Glu Gln Lys Leu Ile Ser Glu Glu Asp Leu
1               5                   10

<210> SEQ ID NO 25
<211> LENGTH: 9
<212> TYPE: PRT
```

-continued

```
<213> ORGANISM: Artificial Sequence
<220> FEATURE:
<223> OTHER INFORMATION: Synthetic construct

<400> SEQUENCE: 25

Tyr Pro Tyr Asp Val Pro Asp Tyr Ala
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic construct

<400> SEQUENCE: 26

His His His His His His
1               5

<210> SEQ ID NO 27
<211> LENGTH: 238
<212> TYPE: PRT
<213> ORGANISM: Aequorea victoria

<400> SEQUENCE: 27

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 28
<211> LENGTH: 194
<212> TYPE: PRT
```

<213> ORGANISM: Aliiyibrio fischeri

<400> SEQUENCE: 28

Met Phe Lys Gly Ile Val Glu Gly Ile Ile Glu Lys Ile Asp
1               5                   10                  15

Ile Tyr Thr Asp Leu Asp Lys Tyr Ala Ile Arg Phe Pro Glu Asn Met
                20                  25                  30

Leu Asn Gly Ile Lys Lys Glu Ser Ser Ile Met Phe Asn Gly Cys Phe
            35                  40                  45

Leu Thr Val Thr Ser Val Asn Ser Asn Ile Val Trp Phe Asp Ile Phe
50                  55                  60

Glu Lys Glu Ala Arg Lys Leu Asp Thr Phe Arg Glu Tyr Lys Val Gly
65                  70                  75                  80

Asp Arg Val Asn Leu Gly Thr Phe Pro Lys Phe Gly Ala Ala Ser Gly
                85                  90                  95

Gly His Ile Leu Ser Ala Arg Ile Ser Cys Val Ala Ser Ile Ile Glu
            100                 105                 110

Ile Ile Glu Asn Glu Asp Tyr Gln Gln Met Trp Ile Gln Ile Pro Glu
        115                 120                 125

Asn Phe Thr Glu Phe Leu Ile Asp Lys Asp Tyr Ile Ala Val Asp Gly
130                 135                 140

Ile Ser Leu Thr Ile Asp Thr Ile Lys Asn Asn Gln Phe Phe Ile Ser
145                 150                 155                 160

Leu Pro Leu Lys Ile Ala Gln Asn Thr Asn Met Lys Trp Arg Lys Lys
                165                 170                 175

Gly Asp Lys Val Asn Val Glu Leu Ser Asn Lys Ile Asn Ala Asn Gln
            180                 185                 190

Cys Trp

<210> SEQ ID NO 29
<211> LENGTH: 225
<212> TYPE: PRT
<213> ORGANISM: Montastraea cavernosa

<400> SEQUENCE: 29

Met Ser Val Ile Lys Ser Val Met Lys Ile Lys Leu Arg Met Asp Gly
1               5                   10                  15

Ile Val Asn Gly His Lys Phe Met Ile Thr Gly Glu Gly Glu Gly Lys
                20                  25                  30

Pro Phe Glu Gly Thr His Thr Ile Ile Leu Lys Val Lys Glu Gly Gly
            35                  40                  45

Pro Leu Pro Phe Ala Tyr Asp Ile Leu Thr Thr Ala Phe Gln Tyr Gly
50                  55                  60

Asn Arg Val Phe Thr Lys Tyr Pro Lys Asp Ile Pro Asp Tyr Phe Lys
65                  70                  75                  80

Gln Ser Phe Pro Glu Gly Tyr Ser Trp Glu Arg Ser Met Thr Phe Glu
                85                  90                  95

Asp Gln Gly Val Cys Thr Val Thr Ser Asp Ile Lys Leu Glu Gly Asp
            100                 105                 110

Cys Phe Phe Tyr Glu Ile Arg Phe Tyr Gly Val Asn Phe Pro Ser Ser
        115                 120                 125

Gly Pro Val Met Gln Lys Lys Thr Leu Lys Trp Glu Pro Ser Thr Glu
130                 135                 140

Asn Met Tyr Val Arg Asp Gly Val Leu Leu Gly Asp Val Ser Arg Thr
145                 150                 155                 160

-continued

Leu Leu Leu Glu Gly Asp Lys His His Arg Cys Asn Phe Arg Ser Thr
              165                 170                 175

Tyr Gly Ala Lys Lys Gly Val Val Leu Pro Glu Tyr His Phe Val Asp
            180                 185                 190

His Arg Ile Glu Ile Leu Ser His Asp Lys Asp Tyr Asn Thr Val Glu
        195                 200                 205

Val Tyr Glu Asn Ala Val Ala Arg Pro Ser Met Leu Pro Val Lys Ala
    210                 215                 220

Lys
225

<210> SEQ ID NO 30
<211> LENGTH: 230
<212> TYPE: PRT
<213> ORGANISM: Discosoma sp.

<400> SEQUENCE: 30

Met Ser Cys Ser Lys Asn Val Ile Lys Glu Phe Met Arg Phe Lys Val
1               5                   10                  15

Arg Met Glu Gly Thr Val Asn Gly His Glu Phe Glu Ile Lys Gly Glu
            20                  25                  30

Gly Glu Gly Arg Pro Tyr Glu Gly His Cys Ser Val Lys Leu Met Val
        35                  40                  45

Thr Lys Gly Gly Pro Leu Pro Phe Ala Phe Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Ser Gln Asp Ser Ser
            100                 105                 110

Leu Lys Asp Gly Cys Phe Ile Tyr Glu Val Lys Phe Ile Gly Val Asn
        115                 120                 125

Phe Pro Ser Asp Gly Pro Val Met Gln Arg Arg Thr Arg Gly Trp Glu
    130                 135                 140

Ala Ser Ser Glu Arg Leu Tyr Pro Arg Asp Gly Val Leu Lys Gly Asp
145                 150                 155                 160

Ile His Met Ala Leu Arg Leu Glu Gly Gly His Tyr Leu Val Glu
                165                 170                 175

Phe Lys Ser Ile Tyr Met Val Lys Lys Pro Ser Val Gln Leu Pro Gly
            180                 185                 190

Tyr Tyr Tyr Val Asp Ser Lys Leu Asp Met Thr Ser His Asn Glu Asp
        195                 200                 205

Tyr Thr Val Val Glu Gln Tyr Glu Lys Thr Gln Gly Arg His His Pro
    210                 215                 220

Phe Ile Lys Pro Leu Gln
225             230

<210> SEQ ID NO 31
<211> LENGTH: 550
<212> TYPE: PRT
<213> ORGANISM: Photinus pyralis

<400> SEQUENCE: 31

Met Glu Asp Ala Lys Asn Ile Lys Lys Gly Pro Ala Pro Phe Tyr Pro
1               5                   10                  15

```
Leu Glu Asp Gly Thr Ala Gly Glu Gln Leu His Lys Ala Met Lys Arg
         20                  25                  30

Tyr Ala Leu Val Pro Gly Thr Ile Ala Phe Thr Asp Ala His Ile Glu
         35                  40                  45

Val Asn Ile Thr Tyr Ala Glu Tyr Phe Glu Met Ser Val Arg Leu Ala
 50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
             100                 105                 110

Glu Leu Leu Asn Ser Met Asn Ile Ser Gln Pro Thr Val Val Phe Val
             115                 120                 125

Ser Lys Lys Gly Leu Gln Lys Ile Leu Asn Val Gln Lys Lys Leu Pro
130                 135                 140

Ile Ile Gln Lys Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                 165                 170                 175

Asn Glu Tyr Asp Phe Val Pro Glu Ser Phe Asp Arg Asp Lys Thr Ile
             180                 185                 190

Ala Leu Ile Met Asn Ser Ser Gly Ser Thr Gly Ser Pro Lys Gly Val
             195                 200                 205

Ala Leu Pro His Arg Thr Ala Cys Val Arg Phe Ser His Ala Arg Asp
             210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                 245                 250                 255

Ile Cys Gly Phe Arg Val Val Leu Met Tyr Arg Phe Glu Glu Glu Leu
             260                 265                 270

Phe Leu Arg Ser Leu Gln Asp Tyr Lys Ile Gln Ser Ala Leu Leu Val
             275                 280                 285

Pro Thr Leu Phe Ser Phe Phe Ala Lys Ser Thr Leu Ile Asp Lys Tyr
             290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                 325                 330                 335

Arg Gln Gly Tyr Gly Leu Thr Glu Thr Thr Ser Ala Ile Leu Ile Thr
             340                 345                 350

Pro Glu Gly Asp Asp Lys Pro Gly Ala Val Gly Lys Val Val Pro Phe
             355                 360                 365

Phe Glu Ala Lys Val Val Asp Leu Asp Thr Gly Lys Thr Leu Gly Val
             370                 375                 380

Asn Gln Arg Gly Glu Leu Cys Val Arg Gly Pro Met Ile Met Ser Gly
385                 390                 395                 400

Tyr Val Asn Asp Pro Glu Ala Thr Asn Ala Leu Ile Asp Lys Asp Gly
                 405                 410                 415

Trp Leu His Ser Gly Asp Ile Ala Tyr Trp Asp Glu Asp Glu His Phe
             420                 425                 430
```

```
Phe Ile Val Asp Arg Leu Lys Ser Leu Ile Lys Tyr Lys Gly Cys Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Gly Asp Asp Ala Gly Glu Leu
465                 470                 475                 480

Pro Ala Ala Val Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
530                 535                 540

Gly Gly Lys Ser Lys Leu
545                 550

<210> SEQ ID NO 32
<211> LENGTH: 311
<212> TYPE: PRT
<213> ORGANISM: Renilla reniformis

<400> SEQUENCE: 32

Met Thr Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
            35                  40                  45

Phe Leu His Gly Asn Ala Ala Ser Ser Tyr Leu Trp Arg His Val Val
        50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255
```

```
Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
        290                 295                 300

Arg Val Leu Lys Asn Glu Gln
305                 310

<210> SEQ ID NO 33
<211> LENGTH: 21
<212> TYPE: PRT
<213> ORGANISM: Artificial Sequence
<220> FEATURE:
<223> OTHER INFORMATION: Synthetic construct

<400> SEQUENCE: 33

Lys Phe Ala Lys Phe Ala Lys Lys Phe Ala Lys Phe Ala Lys Lys Phe
1               5                   10                  15

Ala Lys Phe Ala Lys
            20

<210> SEQ ID NO 34
<211> LENGTH: 30
<212> TYPE: PRT
<213> ORGANISM: Artificial Sequence
<220> FEATURE:
<223> OTHER INFORMATION: Synthetic construct

<400> SEQUENCE: 34

Gly Val Tyr His Phe Ala Pro Leu Thr Pro Thr Pro Gly Gly Gly Ser
1               5                   10                  15

Lys Phe Ala Lys Phe Ala Lys Lys Phe Ala Lys Phe Ala Lys
            20                  25                  30

<210> SEQ ID NO 35
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: 5
<223> OTHER INFORMATION: Xaa = DTPA

<400> SEQUENCE: 35

Gly Gly Gly Ser Xaa
1               5
```

DRUG CONJUGATES FOR DELIVERING COMPOUNDS TO SENESCENT CELLS

This application is Continuation of U.S. patent application Ser. No. 14/750,941, filed Jun. 25, 2015, which is a Divisional of U.S. application Ser. No. 14/557,316, filed Dec. 1, 2014, which is a Continuation of U.S. application Ser. No. 12/809,952, filed Feb. 21, 2012, which is a U.S. national stage entry under 35 USC 371(c) of PCT/US2008/13913, filed Dec. 19, 2008, which claims priority to U.S. Provisional Application No.: 61/015,416, filed Dec. 20, 2007, the contents of which are herein incorporated by reference in their entirety.

FIELD OF THE INVENTION

This invention relates to compositions and methods for the detection and treatment of cancer, age-related diseases, tobacco-related diseases, and other diseases and disorders related to or caused by cellular senescence.

BACKGROUND OF THE INVENTION

The definition of cellular senescence has undergone some revision since the phenomenon was described by Leonard Hayflick as cessation of replication of cultured human cells after a finite number of population doublings (Hayflick et al., *Exp. Cell Res.* 37:585-621, 1961). Senescent cells remain metabolically active but do not divide and resist apoptosis for long periods of time (Goldstein, *Science* 249:1129-1133, 1990). Cellular senescence is characterized by growth cycle arrest in the G1 phase, absence of S phase, and lifespan control by multiple dominant genes (Stanulis-Praeger, *Mech. Ageing Dev.* 38:1-48, 1987).

Cellular senescence differs from quiescence and terminal differentiation in several important aspects. Senescent cells have characteristic morphological changes such as enlargement, flattening, and increased granularity (Dimri et al., *Proc. Nat. Acad. Sci. USA* 92:9363-9367, 1995). Senescent cells do not divide even if stimulated by mitogens (Campisi, *Trends Cell Biol.* 11:S27-S31, 2001). Senescence involves activation of p53 and/or Rb and their regulators such as p16$^{INK4a}$, p21, and ARF. Except when p53 or Rb is inactivated, senescence is irreversible. Senescent cells express increased levels of plasminogen activator inhibitor (PAI) and exhibit staining for β-galactosidase activity at pH 6 (Sharpless et al., *J. Clin. Invest.* 113:160-168, 2004). Irreversible G1 arrest is mediated by inactivation of cyclin dependent kinase (CdK) complexes which phosphorylate Rb. P21 accumulates in aging cells and inhibits CdK4-CdK6. P16 inhibits CdK4-CdK6 and accumulates proportionally with β-galactosidase activity and cell volume (Stein et al., *Mol. Cell. Biol.* 19:2109-2117, 1999). P21 is expressed during initiation of senescence but need not persist; p16 expression helps maintain senescence once initiated.

Replicative senescence, the type of senescence originally observed by Hayflick, is related to the progressive shortening of telomeres with each cell division. Senescence is induced when certain chromosomal telomeres reach a critical length (Mathon and Lloyd, *Nat. Rev. Cancer* 3:203-213, 2001; Martins, U. M. *Exp Cell Res.* 256:291-299, 2000). Senescence can be abrogated by the expression of telomerase which lengthens telomeres; human fibroblasts undergo replication indefinitely when transfected to express telomerase. Most cancers express telomerase in order to maintain telomere length and replicate indefinitely. The minority of cancers that do not express telomerase have alternative lengthening of telomere (ALT) mechanisms.

Indirect evidence suggests some relationship between replicative senescence and aging. Cultured cells from old donors exhibit senescence after fewer population doublings than cells from young donors (Martin et al., *Lab. Invest.* 23:86-92, 1970; Schneider et al., *Proc. Nat. Acad. Sci. USA* 73:3584-3588, 1976). Cells from short-lived species senesce after fewer population doublings than cells from long-lived species (Rohme, D., *Proc. Nat. Acad. Sci. USA* 78:5009-3320, 1981). Cultured cells from donors with hereditary premature aging syndromes such as Werner's syndrome show senescence after fewer replications than cells from age-matched controls (Goldstein, *Genetics of Aging*, 171-224, 1978; Martin, *Genetic Effects on Aging*, 5-39, 1990). Whether replicative senescence actually contributes to aging or age-related symptoms in vivo is questionable on the basis of theoretical estimates of the number of cell divisions that occur in vivo and the absence of strong empirical evidence.

There are, however, other pathways to senescence than replication. Collectively, these are often referred to as stress-induced premature senescence (SIPS). Oxidative stress can shorten telomeres (von Zglinicki, *Trends Biochem. Sci.* 27:339-344, 2002) and hyperoxia has been shown to induce senescence. Gamma irradiation of human fibroblasts in early to mid G1 phase causes senescence in a p53-dependent manner (Di Leonardo et al., *Genes Dev.* 8:2540-2551, 1994). Ultraviolet radiation also induces cellular senescence. Other agents that can induce cellular senescence include hydrogen peroxide (Krtolica et al., *Proc. Nat. Acad. Sci. USA* 98:12072-12077, 2001), sodium butyrate, 5-azacytadine, and transfection with the Ras oncogene (Tominaga, *Mech. Ageing Dev.* 123(8):927-936, 2002). Chemotherapeutic agents including doxorubicin, cisplatin, and a host of others have been shown to induce senescence in cancer cells (Roninson, *Cancer Res.* 63:2705-2715, 2003). 5-bromodeoxyuridine treatment results in cellular senescence in both normal and malignant cells (Michishita et al., *J. Biochem.* 126:1052-1059, 1999). Generally speaking, agents that damage DNA can cause cellular senescence. The existence of cellular senescence in vivo has been demonstrated. In a study by Dimri et al., published in 1995, senescent fibroblasts were shown to exhibit staining for β-galactosidase activity at pH 6. These cells failed to incorporate tritiated thymidine and retained β-galactosidase activity after replating but did not divide. Quiescent fibroblasts did not show staining. Keratinocytes, umbilical vein endothelial cells, and mammary epithelial cells all showed increased staining with increased population doublings. Immortalized cells and terminally differentiated keratinocytes did not show staining. Staining was performed on skin biopsies to test whether senescence is observed in vivo. An age-dependent pattern in which an increased number of cells showed staining with increased donor age was observed in the dermis and epidermis (Dimri et al., *Proc. Nat. Acad. Sci. USA* 92:9363-9367, 1995). The existence of an increase in the number of senescent fibroblasts has been shown in the lungs of subjects with emphysema relative to subjects without emphysema (Müller et al., *Resp. Res.* 7:32-41, 2006).

Cellular senescence confers a number of functional changes on the cell that likely have clinical relevance. Senescent endothelial cells secrete elevated levels of plasminogen activator inhibitor 1 (PAI-1; Kletsas et al., *Ann. N.Y. Acad. Sci.* 908:11-25, 2000). Senescent fibroblasts over express collagenase and under express collagenase inhibitors (West et al., *Exp Cell Res* 184:138-147, 1989). Serial passages of human fibroblasts from a 25 year old donor showed increased elastase endopeptidase type activity (Homsy et al., *Journal of Investigative Dermatology* 91:472-477, 1988). Endothelial cells obtained from tissue overlying atherosclerotic plaques were observed to have a senescent morphology and express increased levels of PAI-1 and intracellular adhesion molecule 1 and decreased levels of nitric oxide (Davis et al., *British Heart Journal* 60:459-464, 1988; *Arterioscler. Thromb.* 11:1678-1689, 1991; Finn et al., *Circulation* 105:1541-1544, 1976; Comi et al., *Exp. Cell Res.* 219:304-308, 1995; Chang et al., *Proc. Nat. Acad. Sci. USA* 92:11190-11194, 1995). Indirect evidence that cellular senescence may play a role in cardiovascular disease also is provided by the observation that shorter leukocyte telomere length is associated with an increased risk of premature myocardial infarction (Brouilette et al., *Arteriosclerosis, Thrombosis, and Vascular Biology* 23:842-846, 2003).

Cancer cells are immortal, meaning that they can replicate indefinitely without exhibiting senescence. A preponderance of opinion in the scientific community says that the teleological purpose of senescence is to prevent cancer by limiting the number of cell divisions that can occur. This view is supported by experiments in mice showing that p53 knockout results in increased cancer incidence and severity. Indirect evidence that senescence suppresses cancer occurrence includes the observations that oncogenes immortalize or extend cellular lifespan and tumor suppressors Rb and p53, which are critical for senescence, suffer a loss of function mutation in cancer (Shay et al., *Biochem. Biophys. Acta.* 1071:1-7, 1991).

Senescent cells can also promote tumorigenesis. Senescent stromal cells express tumor promoting as well as tumor suppressing factors that exert a paracrine effect on neighboring epithelial cells; such effects include mitogenicity and antiapoptosis (Chang et al., *Proc. Nat. Acad. Sci. USA* 97(8):4291-4296, 2000). Senescent fibroblasts have been shown to stimulate premalignant and malignant epithelial cells but not normal epithelial cells to form tumors in mice; this occurred when as few as 10% of the fibroblasts were senescent (Krtolica et al., *Proc. Nat. Acad. Sci. USA* 98:12072-12077, 2001). Tumor promoting factors secreted by senescent cells are partly mediated by $p21^{waf1/cip1/sdi1}$ (Roninson, *Cancer Res.* 63:2705-2715, 2003). A threshold of senescent stromal cells appears to provide a milieu allowing adjacent premalignant epithelial cells to survive, migrate, and divide (Campisi, *Nat. Rev. Cancer* 3:339-349, 2003).

In summary, cellular senescence does occur in vivo and is a likely sequel to environmental insults. Its prevalence increases with age at least in some tissue compartments. Senescence confers functional changes on the cell which have been associated to some degree with various age-related diseases (Chang et al., *Proc. Nat. Acad. Sci. USA* 97(8):4291-4296, 2000). Senescent cells also contribute to tumor formation. There exists a need for agents that are capable of detecting senescent cells in vivo and for treating or preventing diseases and disorders related to or caused by cellular senescence.

SUMMARY OF THE INVENTION

This invention features compositions and methods for the detection and imaging of senescent cells in vitro or in vivo in order to predict the risk of diseases or disorders related to or caused by cellular senescence (e.g., cancer occurrence, cancer metastasis, cardiovascular disease, cerebrovascular disease, Alzheimer's disease, and emphysema). The invention also features compositions and methods for treating, preventing, or inhibiting the development or progression of diseases or disorders related to or caused by cellular senescence (e.g., by administering an agent that results in the death and removal of one or more, all, or substantially all senescent cells or cells expressing one or more senescence markers from an organism). The compositions and methods can be administered in order to prevent, ameliorate, inhibit the development of, or treat diseases or disorders related to or caused by cellular senescence (e.g., cancer, cardiovascular disease, cerebrovascular disease, Alzheimer's disease, emphysema, osteoarthritis, and other age-related diseases). The invention features peptides which bind with higher affinity to senescent cells than non-senescent cells.

In a first aspect, the invention features a peptide, polypeptide, antibody, or antibody fragment agent having an amino acid sequence set forth in any one of SEQ ID NOS:1-3 and 5-8 or a peptide, polypeptide, antibody, antibody fragment, or small molecule agent that is capable of specifically binding to an antigen having an amino acid sequence having at least 20 amino acids with at least 80% sequence identity to any one of the amino acid sequences set forth in SEQ ID NOS:11-23. In one embodiment, the antigen has an amino acid sequence having at least 20 amino acids of any one of the amino acid sequences set forth in SEQ ID NOS:11-23. In another embodiment, the antigen has any one of the amino acid sequences set forth in SEQ ID NOS:11-23.

In embodiments of the first aspect of the invention, the agent includes a detectable label, a therapeutic agent, a chelating agent, or a linker moiety. An agent of the first aspect of the invention can be indirectly or directly attached to the detectable label. The linker moiety can have the amino acid sequence GGGC, GGGS, or GG. A detectable label can be a radioactive agent, fluorescent agent, bioluminescent molecule, epitope tag, or heavy metal. Radioactive agents include iodine, astatine, and bromine labels that are attached to an amino acid of an agent of the first aspect of the invention. A radioactive agent can also be technetium-99m. Fluorescent agents include fluorescein isothiocyanate (FITC), allophycocyanin (APC), phycoerythrin (PE), rhodamine, tetramethyl rhodamine isothiocyanate (TRITC), fluorescent protein (GFP), enhanced GFP (eGFP), yellow fluorescent protein (YFP), cyan fluorescent protein (CFP), red fluorescent protein (RFP), and dsRed. A bioluminescent molecule can be luciferase. Epitope tags include c-myc, hemagglutinin, and histidine tags. A therapeutic agent can be a cytotoxic agent, such as an alkylating agent, an antibiotic, an antineoplastic agent, an antimetabolic agent, a ribosomal activity inhibitor, an antiproliferative agent, a tubulin inhibitor, a topoisomerase I or II inhibitor, a growth factor, an hormonal agonist or antagonists, an apoptotic agent, an immunomodulator, a radioactive agent, a phospholipase, or a cytotoxic peptide or lysin. A cytotoxic agent can also be ricin, doxorubicin, methotrexate, camptothecin, homocamptothecin, thiocolchicine, colchicine, combretastatin, combretastin A-4, podophyllotoxin, rhizoxin, rhizoxin-d, dolistatin, paclitaxel, CC1065, ansamitocin p3, maytansinoid, streptolysin O, stoichactis toxin, phallolysin, *staphylococcus* alpha toxin, holothurin A, digitonin, melittin, lysolecithin, cardiotoxin, cerebratulus A toxin, or any derivative thereof. A chelating agent joined to an agent of the first aspect of the invention can be an ininocarboxylic reactive group, a polyaminopolycarboxylic reactive group, diethylenetriaminepentaacetic acid (DTPA), or 1,4,7,10-tetraazacyclododecane-1,4,7,10-tetraacetic acid (DOTA). In any embodiment, the agent of the first aspect of the invention can further include a pharmaceutically acceptable carrier. An agent of the first aspect of the invention can specifically bind to a senescent cell, such as a senescent lung, breast, colon, prostate, gastric, hepatic, ovarian, esophageal, or bronchial epithelial or stromal cell, a senescent skin epithelial or stromal cell; a senescent glial cell; or a senescent vascular endothelial or stromal cell.

In a second aspect, the invention features a method of imaging a senescent cell-containing region in a mammal, such as a human, in vivo, by administering to the mammal an agent of the first aspect of the invention that is joined to a detectable label, allowing the agent to bind senescent cells and allowing unbound agent to be cleared from the body of said mammal, and obtaining an image of the senescent cell-containing region. Senescent cell-containing regions include the breast, prostate, gastrointestinal tract, liver, lungs, intracranial space, nasopharynx, oropharynx, larynx, esophagus, mediastinum, abdomen and pelvis, any region of the body containing peripheral vasculature, and the entire body. An image of the senescent cell-containing region can be obtained by scintigraphy.

In a third aspect, the invention features a method of predicting cancer risk in a mammal, such as a human, by administering to the mammal an agent of the first aspect of the invention that is joined to a detectable label and predicting an elevated cancer risk in the mammal by detecting binding of the agent to a senescent cell of the mammal. The method can be used to predict the risk of prostate cancer, colon cancer, lung cancer, squamous cell cancer of the head and neck, esophageal cancer, hepatocellular carcinoma, gastric cancer, pancreatic cancer, ovarian cancer, and breast cancer.

In a fourth aspect, the invention features a method of treating or preventing disease in a mammal, such as a human, by administering to the mammal an agent of the first aspect of the invention joined to a cytotoxic agent.

In a fifth aspect, the invention features a method of treating or preventing disease in a mammal, such as a human, by administering to the mammal a nucleic acid molecule encoding a cytotoxic agent and an agent of the first aspect of the invention. The nucleic acid molecule can be administered in a vector, such as an adenoviral vector. In one embodiment, the cytotoxic agent and agent of the first aspect of the invention are expressed as a single polypeptide chain.

In either the fourth or fifth aspects of the invention, diseases that can be treated or prevented include cancer, age-related diseases, tobacco-related diseases, and skin wrinkles. Cancers that can be treated or prevented include prostate cancer, colon cancer, lung cancer, squamous cell cancer of the head and neck, esophageal cancer, hepatocellular carcinoma, gastric cancer, pancreatic cancer, ovarian cancer, and breast cancer. Age-related or tobacco-related diseases include cardiovascular disease, cerebrovascular disease, peripheral vascular disease, Alzheimer's disease, osteoarthritis, cardiac diastolic dysfunction, benign prostatic hypertrophy, aortic aneurysm, and emphysema.

In aسixth aspect, the invention features a method for identifying a peptide or polypeptide capable of detecting senescent cells by (a) culturing cells to produce senescent cells, (b) exposing the senescent cells to a phage peptide library, (c) recovering the senescent cells and phage from said phage peptide library bound to said senescent cells, (d) eluting and amplifying bound phage to produce amplified phage, (e) repeating steps (a)-(d) one or more times, and (f) recovering a peptide or polypeptide expressed by the amplified phage that is capable of detecting senescent cells.

In a seventh aspect, the invention features a method for identifying an antibody or antibody fragment capable of specifically binding to a senescent cell-specific antigen by contacting an antibody or antibody fragment with a polypeptide having at least 20 amino acids having at least 80% amino acid sequence identity to any one of the amino acid sequences set forth in SEQ ID NOS:11-23, and identifying an antibody or antibody fragment that binds the polypeptide with a dissociation constant of less than $10^{-7}$ M.

In an eighth aspect, the invention features a method for identifying an antibody or antibody fragment capable of specifically binding to a senescent cell-specific antigen by administering a polypeptide having at least 20 amino acids having at least 80% amino acid sequence identity to any one of the amino acid sequences set forth in SEQ ID NOS:11-23 to a mammal, allowing the mammal to generate a humoral immune response to the polypeptide, and identifying an antibody or antibody fragment that binds the polypeptide with a dissociation constant of less than $10^{-7}$ M. Mammals suitable for the identification of antibodies that specifically bind senescent cell-specific antigens include mice, hamsters, rats, guinea pigs, chickens, goats, sheep, cows, horses, non-human primates, and humans.

In an ninth aspect, the invention features a method for identifying a small molecule capable of specifically binding to a senescent cell-specific antigen by contacting a small molecule with a polypeptide having at least 20 amino acids having at least 80% amino acid sequence identity to any one of the amino acid sequences set forth in SEQ ID NOS:11-23 and identifying a small molecule that binds the polypeptide with a dissociation constant of less than $10^{-7}$M.

In an tenth aspect, the invention features a method of making an antibody or antibody fragment by recombinantly expressing a nucleic acid sequence that encodes an amino acid sequence having one or more of SEQ ID NOs:1-3 and 5-8, wherein the antibody or antibody fragment specifically binds a senescent cell.

In an eleventh aspect, the invention features a method of cellular therapy performed by administering to a mammal, such as a human, in need thereof an agent of the invention prior to, concurrent with, or following administration of a cellular therapeutic.

In an twelfth aspect, the invention features a method of cellular therapy performed by contacting an agent of the invention to a donor cell, tissue, or organ prior to, concurrent with, or following administration of the cell, tissue, or organ to a mammal, such as a human. A donor cell, tissue, or organ can be an autologous, allogeneic, syngeneic, or xenogeneic cell, tissue, or organ. A donor cell can be a stem cell, such as a hematopoietic, umbilical cord blood, totipotent, multipotent, or pluripotent stem cell.

In a thirteenth aspect, the invention features a kit containing an agent of the invention and one or more of a detectable label, a therapeutic agent, a chelating agent, or a linker moiety.

The term "about" is used herein to mean a value that is ±10% of the recited value.

By "administration" or "administering" is meant a method of providing a dosage of an agent of the invention to a mammal (e.g., a human), where the route is, e.g., topical, oral, parenteral (e.g., intravenous, intraperitoneal, intrarterial, intradermal, intramuscular, or subcutaneous injection, inhalation, optical drops, or implant), nasal, vaginal, rectal, or sublingual application in admixture with a pharmaceutically acceptable carrier adapted for such use. The preferred method of administration can vary depending on various factors, e.g., the components of the pharmaceutical composition, site of the potential or actual disease (e.g., the location of lung, breast, colon, prostate, liver, brain, heart, etc.), and the severity of disease.

By "analog" is meant an agent that differs from, but is structurally, functionally, and/or chemically related to the reference agent. The analog may retain the essential properties, functions, or structures of the reference agent. Most preferably, the analog retains at least one biological function of the reference agent. Generally, differences are limited so that the structure or sequence of the reference agent and the analog are similar overall. For example, a peptide analog and its reference peptide may differ in amino acid sequence by one or more amino acid substitutions, additions, and/or deletions, or the presence of one or more non-naturally occurring amino acid residues, in any combination. An analog of a peptide or polypeptide of the invention may be naturally occurring, such as an allelic variant, or it may be a variant that is not known to occur naturally. Non-naturally occurring analogs of peptides may be made by direct synthesis, by modification, or by mutagenesis techniques.

By "chelating agent" is meant a molecule that forms multiple chemical bonds with a single metal atom. Prior to forming the bonds, the chelating agent has more than one pair of unshared electrons. The bonds are formed by sharing pairs of electrons with the metal atom. Chelating agents include, for example, an iminodicarboxylic group or a polyaminopolycarboxylic group. Chelating agents may be attached to an agent of the invention using the methods generally described in Liu et al., *Bioconjugate Chem.* 12(4): 653, 2001; Alter et al., U.S. Pat. No. 5,753,627; and PCT Publication No. WO 91/01144; each of which is hereby incorporated by reference). An agent of the invention may be complexed, through its attached chelating agent, to a detectable label, thereby resulting in an agent that is indirectly labeled. Similarly, cytotoxic or therapeutic agents, may also be attached via a chelating group to an agent of the invention.

By "coupled" is meant the characteristic of a first molecule being joined to a second molecule by a covalent bond or through noncovalent intermolecular attraction.

By "cytotoxic agent" is meant any naturally occurring, modified, or synthetic compound that is toxic to cells. Such agents are useful in the treatment of neoplasms, and in the treatment of other symptoms or diseases characterized by cell proliferation or a hyperactive cell population. Cytotoxic agents can also be used to target undesirable cells or tissues other than neoplastic cells or tissues, e.g., senescent cells. Cytotoxic agents include, but are not limited to, alkylating agents, antibiotics, antimetabolites, tubulin inhibitors, topoisomerase I and II inhibitors, hormonal agonists or antagonists, immunomodulators, or agents that cause cell lysis including naturally occurring or synthetic peptides. Cytotoxic agents may be cytotoxic when activated by light or infrared (Photofrin, IR dyes; *Nat. Biotechnol.* 19(4):327-331, 2001), may operate through other mechanistic pathways, or be supplementary potentiating agents.

By "detectable label" is meant any type of label which, when attached to an agent of the invention, renders the agent detectable. A detectable label may be toxic or non-toxic, and may have one or more of the following attributes, without restriction: fluorescence (Kiefer et al., WO 9740055), color, toxicity (e.g., radioactivity, e.g., a γ-emitting radionuclide, Auger-emitting radionuclide, β-emitting radionuclide, an α-emitting radionuclide, or a positron-emitting radionuclide), radiosensitivity, or photosensitivity. Although a detectable label may be directly attached, for example, to an amino acid residue of an agent of the invention, or indirectly attached, for example, by being complexed with a chelating group that is attached (e.g., linked via a covalent bond or indirectly linked) to an amino acid residue of an agent of the invention. A detectable label may also be indirectly attached to an agent of the invention by the ability of the label to be specifically bound by a second molecule. One example of this type of an indirectly attached label is a biotin label that can be specifically bound by a second molecule, streptavidin. The second molecule may also be linked to a moiety that allows neutron capture (e.g., a boron cage as described in, for example, Kahl et al., *Proc. Natl. Acad. Sci. USA* 87:7265-7269, 1990).

A detectable label may also be a metal ion from heavy elements or rare earth ions, such as $Gd^{3+}$, $Fe^{3+}$, $Mn^{3+}$, or $Cr^{2+}$ (see, e.g., Curter, *Invest. Radiol.* 33(10):752-761, 1998). Preferred radioactive detectable labels are radioactive iodine labels (e.g., $^{122}I$, $^{123}I$, $^{124}I$, $^{125}I$, or $^{131}I$) that are capable of being coupled to each D- or L-Tyr or D- or L-4-amino-Phe residues present in the agents of the invention. Preferred non-radioactive detectable labels are the many known dyes that are capable of being coupled to $NH_2$-terminal amino acid residues.

Preferred examples of detectable labels that may be toxic to cells include ricin, diphtheria toxin, and radioactive detectable labels (e.g., $^{122}I$, $^{123}I$, $^{124}I$, $^{125}I$, $^{131}I$, $^{177}Lu$, $^{64}Cu$, $^{67}Cu$, $^{153}Sm$, $^{166}Ho$, $^{186}Re$, $^{188}Re$, $^{211}At$, $^{212}Bi$, $^{225}Ac$, $^{67}Ga$, $^{68}Ga$, $^{75}Br$, $^{76}Br$, $^{77}Br$, $^{117m}Sn$, $^{47}Sc$, $^{109}Pd$, $^{89}Sr$, $^{159}Gd$, $^{149}Pm$, $^{142}Pr$, $^{111}Ag$, $^{165}Dy$, $^{213}Bi$, $^{111}In$, $^{114m}In$, $^{201}Ti$, $^{195m}Pt$, $^{193}Pt$, $^{86}Y$ and $^{90}Y$). These compounds, and others described herein may be directly or indirectly attached to an agent of the invention or its analogs. A toxic detectable label may also be a chemotherapeutic agent (e.g., camptothecins, homocamptothecins, 5-fluorouracil or adriamycin), or may be a radiosensitizing agent (e.g., paclitaxel, gemcitabine, fluoropyrimidine, metronitozil, or the deoxycytidine analog 2',2' difluoro-2'-deoxycytidine (dFdCyd) to which is directly or indirectly attached an agent or analog thereof of the present invention.

A detectable label, when coupled to an agent of the invention emits a signal that can be detected by a signal transducing machine. In some cases, the detectable label can emit a signal spontaneously, such as when the detectable label is a radionuclide. In other cases the detectable label emits a signal as a result of being stimulated by an external field such as when the detectable label is a relaxivity metal. Examples of signals include, without limitation, gamma rays, X-rays, visible light, infrared energy, and radio waves. Examples of signal transducing machines include, without limitation, gamma cameras including SPECT/CT devices, PET scanners, fluorimeters, and Magnetic Resonance Imaging (MRI) machines.

By "diagnostically effective amount" is meant a dose of detectably-labeled agent that, when administered internally to a mammal, is quantitatively sufficient to be detected by a signal transducing machine external to the mammal (e.g., a gamma camera used in gamma scintigraphy) but typically is quantitatively insufficient to produce a pharmacological effect.

By "imaging agent" is meant a compound that, when administered to a living subject, such as a mammal (e.g., a human), allows the visualization of internal structures (e.g., cells, tissues, and organs) and, in some cases can provide information as to the function of a cell, tissue, or organ in the subject.

By "linker moiety" is meant a sequence of amino acid residues, e.g., at least one, two, three, four, five, six, seven, eight, nine, ten, fifteen, twenty, thirty, forty, fifty, or more residues, that couples an agent of the invention (e.g., a peptide, polypeptide, protein, small molecule, antibody, or antibody fragment that target senescent cells) to, e.g., one or more of a detectable label, a therapeutic agent, and a chelating agent.

By "senescent cell" is meant a cell that is metabolically active but is permanently withdrawn from the cell cycle (see, e.g., Campisi, Cell 120:513-522, 2005). Senescent cells do not replicate and possess one or more of the following additional characteristics attributed to senescent cells: cell cycle arrest in the G1 phase; an enlarged, flattened morphology; increased granularity; staining for β-galactosidase activity at pH 6; senescence associated heterochromatic foci; and characteristic gene expression that is in part regulated by p16 and p21. Alternatively, a senescent cell is a cell that can be induced to become senescent (e.g., by stress) or that expresses cell-surface markers characteristic of senescent cells; these markers include senescent cell-specific antigens having the polypeptide sequences set forth in SEQ ID NOS:11-23. Senesecent cell-specific antigens are those peptides, polypeptides, or glycoproteins that are expressed on the cell surface of senescent cells, but are absent or only weakly expressed on the cell surface of non-senescent cells.

By "peptide" is meant a polymer that includes two or more amino acids joined to each other by a peptide bond or a modified peptide bond. "Peptide" refers to both short chain polymers, commonly referred to as peptides, oligopeptides, or oligomers, having, e.g., about 10-50 linked amino acid residues, and to longer polymers having up to about 100 amino acid residues in length. Peptides may contain amino acids other than the 20 gene-encoded amino acids, and linkages other than peptide bonds and may include cyclic or branched peptides. "Peptides" include amino acid sequences modified either by natural processes, or by chemical modification techniques that are well known in the art. Modifications may occur anywhere in a polypeptide, including the peptide backbone, the amino acid side-chains, and the amino or carboxyl termini.

The notations used herein for the peptide amino acid residues are those abbreviations commonly used in the art. The less common abbreviations Abu, Ava, β-Ala, hSer, Nle, Nva, Pal, Dab, and Dap stand for 2-amino-butyric acid, amino valeric acid, beta-aminopropionic acid, homoserine, norleucine, norvaline, (2,3, or 4) 3-pyridyl-Ala, 1,4-diaminobutyric acid, and 1,3-diaminopropionic acid, respectively. In all aspects of the invention, it is noted that when amino acids are not designated as either D- or L-amino acids, the amino acid is either an L-amino acid or could be either a D- or L-amino acid. Examples of peptides of the invention include those peptides having the sequence of, or a sequence substantially identical to, the sequences set forth in SEQ ID NOs:1-3 and 5-8 and related sequences. These peptide sequences can also be incorporated into a polypeptide, protein, antibody, or antibody fragment.

By "reducing agent" is meant a chemical compound used to reduce another chemical compound by donating electrons, thereby becoming oxidized.

By "specifically binds" is meant that an agent of the invention recognizes and binds to a target (e.g., a senescent cell), but does not substantially recognize and bind to a non-target (e.g., non-senescent cells), both in vivo and in a sample, e.g., an in vitro biological sample, that includes, e.g., senescent cells. A desirable agent of the invention specifically binds to senescent cells. Preferably, the agents of the invention bind senescent cells with at least 2, 5, 10, 20, 100, or 1000 fold greater affinity than they bind to non-senescent cells. Alternatively, agents of the invention specifically bind to senescent cells with a dissociation constant less than $10^{-6}$M, more preferably less than $10^{-7}$M, $10^{-8}$M, $10^{-9}$M, $10^{-10}$M, $10^{-11}$M, or $10^{-12}$M, and most preferably less than $10^{-13}$M, $10^{-14}$M, M or $10^{-15}$M.

By "substantial sequence identity" or "substantially identical" is meant that a nucleic acid or amino acid sequence exhibits at least 50%, preferably 60%, 70%, 75%, or 80%, more preferably 85%, 90% or 95%, and most preferably 99% identity to a reference amino acid sequence (e.g., one or more of the sequences set forth in SEQ ID NOs:1-3 and 5-8). For amino acid sequences, the length of comparison sequences will generally be at least 5 amino acids, preferably at least 10 contiguous amino acids, more preferably at least 15, 20, 25, 30, 40, 50, 60, 80, 90, 100, 150, 200, 250, 300, or 350 contiguous amino acids, and most preferably the full-length amino acid sequence. Sequence identity is typically measured using BLAST® (Basic Local Alignment Search Tool) or BLAST® 2 with the default parameters specified therein (see, Altschul et al., J. Mol. Biol. 215:403-410, 1990); and Tatiana et al., FEMS Microbiol. Lett. 174:247-250, 1999). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "therapeutic agent" is meant any compound that is used in the detection, diagnosis or treatment of disease. Such compounds may be naturally-occurring, modified, or synthetic. A therapeutic agent may be, for example, an agent that causes apoptosis or necrosis of a cell (e.g., a senescent cell) in an organism (e.g., a mammal, such as a human), thereby reducing the number of such cells in the organism. Therapeutic agents that reduce the number of senescent cells in an organism may be, e.g., alkylating agents, antibiotics, antimetabolites, hormonal agonists or antagonists, anti- or pro-apoptotic agents, immunomodulators, or supplementary potentiating agents.

By "treating, stabilizing, or preventing cancer" is meant causing a reduction in the size of a tumor or in the number of cancer cells, slowing or preventing an increase in the size of a tumor or in cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay, such as those described herein. Desirably, the decrease in the number of tumor or cancerous cells induced by administration of a compound of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or number of cancerous cells as determined using standard methods. Desirably, at least 20, 40, 60, 80, 90, or 95% of the treated subjects have a complete remission in which all evidence of the tumor or cancer disappears. Desirably, the tumor or cancer does not reappear after more than 5, 10, 15, or 20 years.

By "treating, stabilizing, or preventing age-related diseases" is meant causing a reduction in the number of symptoms, a decrease in severity of any, all, or substantially all of the symptoms, a complete resolution of any, all, or substantially all symptoms, or preventing the occurrence of any, all, or substantially all symptoms associated with one or more of the age-related diseases including, but not limited to, cardiovascular disease, cerebrovascular disease, peripheral vascular disease, Alzheimer's disease, osteoarthritis, cardiac diastolic dysfunction, benign prostatic hypertrophy, and cancers that increase in incidence and prevalence with increasing patient age such as cancer, e.g., breast cancer, prostate cancer, and colon cancer.

By "treating, stabilizing, or preventing tobacco-related diseases" is meant causing a reduction in the number of symptoms, a decrease in severity of any, all, or substantially all of the symptoms, a complete resolution of any, all, or substantially all symptoms, or preventing the occurrence of any, all, or substantially all symptoms associated with one or more of the diseases associated with the use of smoking tobacco as a risk factor, including, but are not limited to, cardiovascular disease, cerebrovascular disease, peripheral vascular disease, aortic aneurysms, emphysema, esophageal cancer, lung cancer, and squamous cell cancers of the head and neck. Tobacco-related diseases also include diseases that are associated with the use of chewing tobacco, such as squamous cell cancers of the mouth.

Other features and advantages of the invention will be apparent from the following description and from the claims.

DETAILED DESCRIPTION OF THE INVENTION

Figure 1:
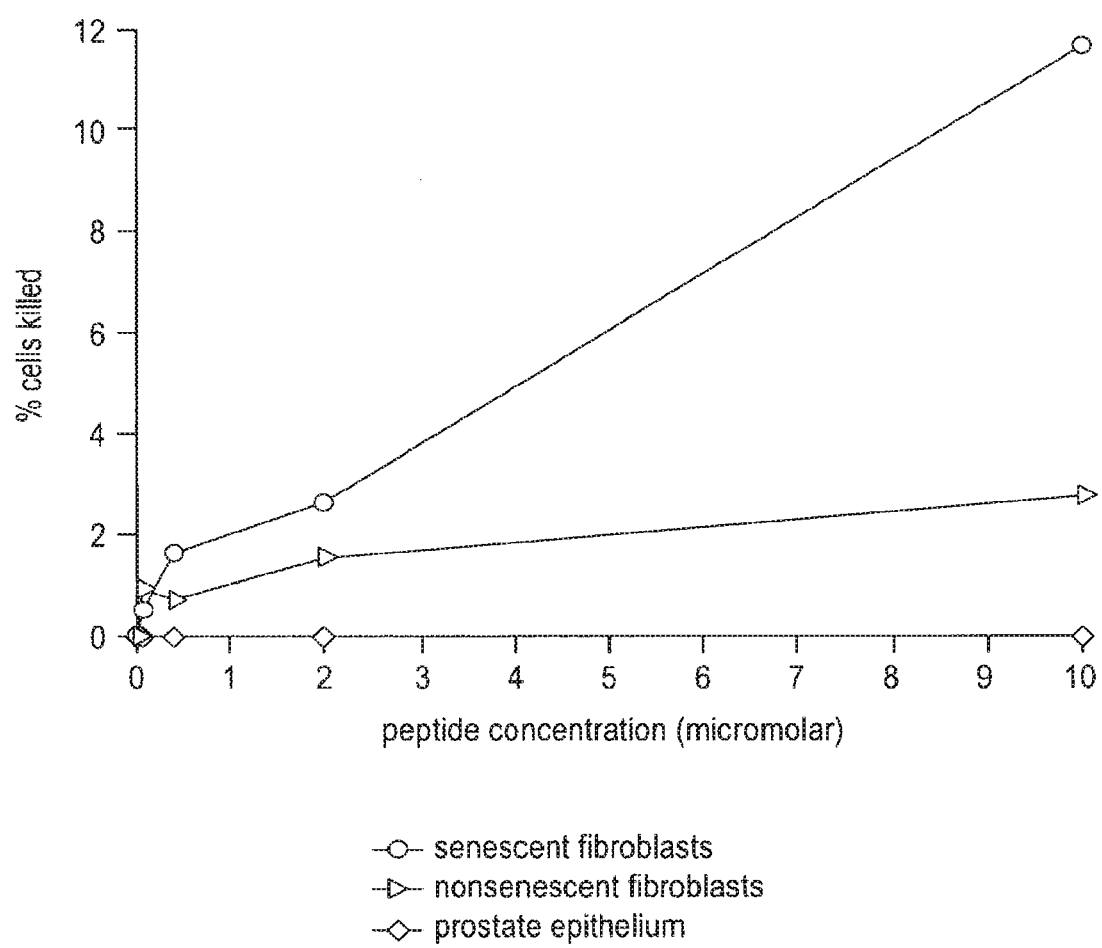
FIG. 1 is a graph showing the cytotoxicity of SenL (SEQ ID NO:4) when tested on senescent fibroblasts, non-senescent fibroblasts, and immortalized prostate epithelial cells. No cell death was observed in immortalized epithelium.

The invention features agents of the invention (e.g., peptides, polypeptides, proteins, small molecules, antibodies, or antibody fragments that target senescent cells) capable of specifically binding to senescent cells. Thus, agents of the invention can include, e.g., detectable labels, therapeutic agents, chelating agents, and cytotoxic agents, and can be used in the detection and treatment of diseases and conditions associated with cellular senescence.

In an embodiment, agents of the invention (e.g., peptides, polypeptides, proteins, small molecules, antibodies, or antibody fragments that target senescent cells) can be used to produce imaging agents by conjugation to a detectable label and used for medical imaging. Images obtained using an imaging agent of the invention specifically show tissues, organs, and structures in the body (e.g., a human body) that contain senescent cells by means of, e.g., a signal emitted from the location of the cells, tissues, organs, and structures upon specific binding of the imaging agent to the senescent cells. The signal so obtained indicates the presence of senescent cells and allows semi-quantitative estimation of the relative senescent cell content of tissues, organs, or structures. Structures, tissues, or organs that contain a threshold content of senescent cells are at an elevated risk for the subsequent development of diseases or disorders (e.g., cancer). Typically, a subject deemed at risk for the subsequent development of diseases or disorders (e.g., cancer) exhibit an increase of at least 0.5%, more preferably 1, 1.5, 2, 2.5, 5, or 10%, and more preferably at least 15% or more in the level of senescent cells relative to a patient that does not have the disease or disorder. Use of one or more of the imaging agents of the invention allows for the determination of a patient's risk for developing a disease or disorder, such as cancer or a neurodegenerative disease. Patients determined to have an elevated risk of developing cancer or other diseases and disorders related to or caused by cellular senescence by the use of the imaging agents of the invention can be aggressively monitored, and their cellular senescence related disease or disorder (e.g., a cancer) can thereby be detected earlier, facilitating early treatment. Surgical prophylactic treatment can also be administered if necessary.

One or more of the imaging agents of the invention can also be used to determine the senescent cell content in the brain, which may include, e.g., senescent glial cells and senescent cerebrovascular cells, in order to predict the patient's risk of developing, e.g., Alzheimer's disease or cerebrovascular disease. One or more of the imaging agents of the invention can also be used to predict the onset of vascular disease, including cardiovascular disease, by detecting the senescent cell content in one or more vascular structures in a patient. One or more of the imaging agents of the invention can also be used to predict the risk of developing emphysema by determining the senescent cell content in the lungs of a smoker.

One or more of the agents of the invention (e.g., peptides, polypeptides, proteins, small molecules, antibodies, or antibody fragments that target senescent cells) can also be used to prepare compositions for therapeutic administration (e.g., to treat, stabilize, inhibit the development or progression of, or prevent age-related diseases, tobacco-related diseases, cancer, neurodegenerative diseases, and other diseases and disorders related to or caused by cellular senescence) by coupling of the agents of the invention to, e.g., therapeutic and/or cytotoxic agents. Senescent cells have been observed in skin to make up only a fraction of the stromal cell compartment even in old donors (Dimri et al., *Proc. Nat. Acad. Sci. USA* 92:9363-9367, 1995) and up to 16% of stromal fibroblasts in patients with emphysema (Bergner, *Respiratory Res.* 7:32, 2006), but senescent cells can exert clinically significant paracrine effects even when they compose only 10% of the content of stromal cells (Krtolica et al., Proc. Nat. Acad. Sci. USA 98:12072-12077, 2001). Thus, eliminating senescent cells while leaving intact the majority of the cellular compartment from which the senescent cells originate can ablate the harmful paracrine effects of senescent cells. The secretion of elevated levels of collagenase and elastase and depressed levels of collagenase inhibitors by senescent stromal cells implicates them in diseases or conditions that feature breakdown or decrease in structural integrity of the extra cellular matrix, including emphysema, aortic aneurysms, vascular disease, osteoarthritis, and skin wrinkling. Elimination of some, all, or substantially all senescent stromal cells in a patient (e.g., in a tissue or organ of a patient) can attenuate the progression, decrease the symptoms, or prevent the occurrence of these diseases and conditions. Senescent stromal cells have the ability to stimulate tumorigenesis and, by weakening the extracellular matrix, facilitate metastasis. Thus, the elimination of some, all, or substantially all of the senescent stromal cells in a patient (e.g., in a tissue or organ of a patient) can decrease the risk of tumorigenesis and metastasis (e.g., by 10%, 20%, 30%, 40%, 50%, 60%, 70%, 80%, 90%, 95%, 99% or more).

The senescent cell targeting agents of the invention (e.g., peptides, polypeptides, proteins, small molecules, antibodies, or antibody fragments that target senescent cells) can be prepared by amino acid coupling using solid phase peptide synthesis (SPPS). As is known in the art, the amino acids to be used as substrates to form the agents of the invention are Fmoc-protected prior to incorporation into a peptide chain (see, e.g., Chanand White, FMOC Solid Phase Peptide Synthesis, A Practical Approach, Oxford University Press, New York, 2003); incorporated herein by reference in its entirety). The standard coupling techniques used to couple the amino acids in order to form the agents of the invention are known in the art (see, e.g., Chan and White, supra). For example, a polyamide-Rink resin can be prepared by loading a polyamide resin with Fmoc-Rink using chemical protocols well known in the art (see, e.g., Chan and White, supra). The first amino acid in the peptide sequence is coupled to the resin after removing Fmoc from the N-terminal amine of the resin using piperidine. Once the coupling is complete, the resin is washed and Fmoc is removed from the coupled amino acid using piperidine. The resin is washed again, and the next amino acid in the sequence is coupled to the previously coupled amino acid. This process is repeated using the necessary amino acids until the desired peptide is formed. Following the coupling of the final amino acid, the Fmoc group is removed using piperidine. The terminal amine can be left as a free amine, or it can be acetylated. The peptide can be cleaved from the resin using trifluoroacetic acid (TFA), triisopropylsilane, and water according to techniques known in the art (see, e.g., Chan and White, supra). The cleaved peptide is then separated from the residue by filtration. The TFA is typically evaporated to dryness followed by precipitation of the peptide with diethyl ether. Typically, the final peptide product is purified using HPLC. Mass spectrometry is used to verify that the desired peptide is obtained. The agents of the invention (e.g., peptides, polypeptides, proteins, small molecules, antibodies, or antibody fragments that target senescent cells) can be readily prepared by automated solid phase peptide synthesis using any one of a number of well-known, commercially available automated synthesizers, such as the Applied Biosystems ABI 433A peptide synthesizer.

The agents of the invention (e.g., peptides, polypeptides, proteins, small molecules, antibodies, or antibody fragments that target senescent cells) can be labeled for fluorescence detection by labeling the agent with a fluorophore, such as rhodamine or fluorescein, using techniques well known in the art (see, e.g., Lohse et al., Bioconj. Chem. 8:503-509, 1997). The senescent cell targeting agents of the invention (e.g., peptides, polypeptides, proteins, small molecules, antibodies, or antibody fragments that target senescent cells) can also be labeled with a radioactive metal or a relaxivity metal by coupling the agent to a metal chelating agent that chelates a radioactive metal or relaxivity metal. Examples of chelating agents include, but are not limited to, ininocarboxylic and polyaminopolycarboxylic reactive groups, diethylenetriaminepentaacetic acid (DTPA), and 1,4,7,10-tetraazacyclododecane-1,4,7,10-tetraacetic acid (DOTA). The chelating agent can be coupled via its amino acid side chain directly to the agents of the invention. Alternatively, an intervening amino acid sequence can be coupled using SPPS to both the agents of the invention and the chelating agent.

Senescent Cell-Specific Antigens

The inventors have discovered that senescent cells express senescent cell-specific antigens. These antigens can be specifically targeted and bound by the diagnostic or therapeutic (e.g., cytotoxic) agents of the invention, as discussed herein. The specific binding of the diagnostic or therapeutic agents of the invention only to senescent cells and not non-senescent cells reduces the incidence of inaccurate diagnoses (e.g., using diagnostic agents) or bystander cell injury (e.g., resulting from cytotoxic agents).

Senescent cell-specific antigens that can be targeted by agents of the invention include, e.g., mutant beta-actin (SEQ ID NO:11; GI: 28336) and beta-actin (ACTB) protein (SEQ ID NO:12; GI: 15277503), which were identified as cell-surface, senescent-specific antigens occurring in both replicatively senescent and stress-induced prematurely senescent cells, drug resistance-related protein LRP (SEQ ID NO:13; GI: 1097308) and major vault protein (MVP; SEQ ID NO:14; GI: 19913410), which were identified as senescence-specific surface proteins in the replicatively senescent cells only, and thyroid hormone binding protein precursor (SEQ ID NO:15; GI: 339647), unnamed protein product (SEQ ID NO:20; GI: 35655), prolyl 4-hydroxylase, beta subunit precursor (P4HB; SEQ ID NO:16; GI: 20070125), chain A, human protein disulfide isomerase (PDI; SEQ ID NO:17; GI: 159162689), electron-transfer-flavoprotein, beta polypeptide (ETFB; SEQ ID NO:18; GI: 4503609), unnamed protein product (SEQ ID NO:21; GI: 158257194), unnamed protein product (SEQ ID NO:22; GI: 158259937), ATP synthase, $H^+$ transporting, mitochondrial F1 complex, alpha subunit precursor (SEQ ID NO:19; GI: 4757810), and cathepsin B (CTSB; SEQ ID NO:23), which were identified on the cell surface of stress induced prematurely senescent cells.

Antibodies that specifically bind to the senescent cell-specific antigens described herein are listed in Table 1. These antibodies, and any other polypeptide, antibody, antibody fragment, or small molecule that specifically binds a senescent cell-specific antigen or fragment thereof, can be incorporated in a diagnostic or therapeutic agent of the invention, as discussed herein. In addition, the antibodies listed in Table 1 can be modified, e.g., by humanization, according to known methods, as is discussed below, for use in the diagnosis and treatment of disease in a mammal, e.g., a human. Alternatively, antibodies against the senescent cell-specific antigens described herein for use in the diagnosis and treatment of disease in a mammal, e.g., a human, can be produced according to methods known in the art, as is discussed below.

TABLE I

| Senescent Cell-Specific Antigen | SEQ ID NO: | Anti-Senescent Cell-Specific Antigen Antibodies |
|---|---|---|
| Mutant beta-actin | 11 | See, e.g., Leavitt et al., Mol Cell Biol. 7: 2467-2476 (1987); Lin et al., PNAS USA 82: 6995-6999(1985). |
| Beta-actin (ACTB) protein | 12 | Clone AC-15 (mouse anti-human beta-actin antibody); Clone mAbeam 8226 (mouse anti-human beta-actin antibody). |
| Drug resistance-related protein LRP | 13 | Clone 1032 (mouse anti-human LRP antibody); rabbit anti-human LRP antibody (see, e.g., Kitazono et al., J. Natl. Cancer Inst. 91: 1647-1653 (1999)). |
| Major vault protein (MVP) | 14 | Clone 1014 (mouse anti-human major vault protein antibody); clone 2Q431(mouse anti-human major vault protein antibody). |
| Thyroid hormone binding protein precursor | 15 | See, e.g., Cheng et al., J. Biol. Chem. 262: 11221-11227 (1987). |
| Prolyl 4-hydroxylase, beta subunit precursor (P4HB) | 16 | Clone P4HB (Abeam Cat. No. ab70415; mouse anti-human prolyl 4-hydroxylase, beta subunit precursor antibody). |
| Chain A, human protein disulfide isomerase (PDI) | 17 | Abeam Cat. No. ab48167 (rabbit anti-human PDI antibody); clone 1D3 (Santa Cruz Cat. No. sc-59640; mouse anti-human PDI antibody). |
| Electron-transfer-flavoprotein, beta polypeptide (ETFP) | 18 | Abeam Cat. No. ab73986 (rabbit anti-human ETFP antibody. |
| ATP synthase, H+ transporting, mitochondrial F1 complex, alpha subunit precursor | 19 | Clone 15H4 (Abeam Cat. No. ab14748; mouse anti-human ATP5A); see also, e.g., Vantourout et al., Mol. Immunol. 45: 485-492 (2008). |
| Unnamed protein product (GI: 35655) | 20 | See, e.g., Pihlajaniemi et al., EMBO J. 6: 643-649 (1987). |
| Unnamed protein product (GI: 158257194) | 21 | See, e.g., Altsehul et al., Nucleic Acids Res. 25: 3389-3402 (1997) |
| Unnamed protein product (GI: 158259937) | 22 | See e.g., Heidebrecht et al., Mol Cancer Res. 1: 271-9 (2003) |
| Cathepsin B (CTSB) | 23 | Clone ZZ12 (mouse anti-human cathepsin B antibody); clone S-12 (goat anti-human cathepsin B antibody). |

Small Molecules of the Invention

The invention also features small molecules that can be used diagnostically or therapeutically based on their ability to specifically bind senescent cells. For example, small molecules of the invention include those capable of specifically binding to one or more of the senescent cell-specific antigens described herein and those capable of mimicking the physical, chemical, biological, and/or targeting characteristics of SEQ ID NOs:1-3 and 5-8 and peptides that are substantially identical. Small molecules of the invention can be labeled or fused to diagnostic or therapeutic linkers, markers, cytotoxic agents, or other agents of the invention to aid in the diagnosis or treatment of diseases or disorders related to or caused by cellular senescence. Furthermore, small molecules of the invention can specifically bind a polypeptide that has at least 80% (80%, 90%, 95%, 99%, or 100%) amino acid sequence identity to any one of the amino acid sequences set forth in SEQ ID NOS:11-23, or a fragment thereof.

Methods of screening small molecules for binding to senescent cells

The invention also features methods for the high throughput screening (HTS) of candidate small molecule agents of the invention for their ability to bind senescent cells or senescent cell-specific antigens, including, but not limited to, the polypeptides set forth in SEQ ID NOS:11-23, or fragments thereof. Candidate small molecules will also be screened for their ability to specifically bind senescent cells. In general, candidate small molecules preferably bind target sequences with a dissociation constant less than $10^{-6}$ M for further consideration as an agent of the invention.

Senescent cells of any origin can be used in HTS binding assays and methods. In general, fluorescence and luminescence based assays (e.g., ELISA, colorimetric assays) are used to measure binding affinities of candidate small molecules contacted against single or multiple target senescent cells. Upon the identification of a candidate small molecule from a first screening process, further scrutiny of the binding affinity and ability of the candidate small molecule can be by means of a second, different HTS assay. This could be accomplished, for example, by contacting the candidate small molecule with alternate senescent cell populations to more precisely determine the binding affinity of the molecule. A discussion of HTS methodologies is found in, e.g., Verkman, "Drug discovery in academia," Am. J. Physiol. Cell Physiol. 286, C465-C474 (2004) and Dove, "Screening for content—the evolution of high throughput," Nat. Biotechnol. 21:859-864 (2003). Examples of HTS screening methods for the discovery of useful small molecule agents are found in, e.g., U.S. Pat. Nos. 7,279,286 and 7,276,346, which are incorporated by reference herein.

Candidate small molecules that have undergone HTS screening may be further modified to empirically improve senescent cell binding affinities according to the design considerations discussed below.

Small Molecule Design

Small molecules of the invention can also be generated according to the principles of rational design. Computer modeling technology allows visualization of the three-dimensional atomic structure of a selected molecule and the design of new compounds that will interact with senescent cells or senescent cell-specific antigens (e.g., the senescent cell-specific antigens discussed above (set forth in SEQ ID NOS:11-23), or fragments thereof). The three-dimensional construct typically depends on data from x-ray crystallographic analyses or NMR imaging of the selected molecule or epitope. A computer graphics system enables prediction of how a candidate small molecule compound will bind to the target senescent cell and allows experimental manipulation of the structures of the small molecule and target protein to perfect binding specificity. A prediction of what the molecule-protein interaction will be when small changes are made in one or both can be determined by using molecular mechanics software and computationally intensive computers. An example of a molecular modeling system described generally above includes the CHARMm and QUANTA programs (Polygen Corporation, Waltham, Mass.). CHARMm performs the energy minimization and molecular dynamics functions, while QUANTA performs the construction, graphic modeling and analysis of molecular structure. QUANTA allows interactive construction, modification, visualization, and analysis of the behavior of molecules that intact with each other. Another molecular modeling program that can be used to identify small molecules for use in the methods of the invention is DOCK (Kuntz Laboratory, UCSF).

Small Molecule Synthesis

Small molecules of the invention can be organic or inorganic compounds, and even nucleic acids. Specific binding to senescent cells can be achieved by including chemical groups having the correct spatial location and charge in the small molecule. In a preferred embodiment, compounds are designed with hydrogen bond donor and acceptor sites arranged to be complementary to the targeted molecule or epitope. An agent is formed with chemical side groups ordered to yield the correct spatial arrangement of hydrogen bond acceptors and donors when the agent is in a specific conformation induced and stabilized by binding to the target molecule or epitope. Additional binding forces such as ionic bonds and Van der Waals interactions can also be considered when synthesizing a small molecule of the invention. The likelihood of forming the desired conformation can be refined and/or optimized using molecular computational programs.

Organic compounds can be designed to be rigid, or to present hydrogen bonding groups on edge or plane, which can interact with complementary sites. Rebek, *Science* 235, 1478-1484 (1987) and Rebek et al., *J. Am. Chem. Soc.* 109, 2426-2431 (1987) have summarized these approaches and the mechanisms involved in binding of compounds to regions of proteins.

Synthetic methods can be used by one skilled in the art to make small molecules that interact with functional groups of proteins, glycoproteins, or epitopes present on the exterior or in the interior of senescent cells.

Preparation of Antibody Compositions of the Invention

The invention also provides antibody compositions that include one or more of the sequences set forth in SEQ ID NOS:1-3 and 5-8, and peptides substantially identical thereto, which can be included in, e.g., one or more of the complementarity determining regions (CDRs) of the antibody compositions. The invention further provides antibody compositions that specifically bind a senescent cell-specific antigen having at least 80% (e.g., 80%, 90%, 95%, 99%, or 100%) amino acid sequence identity to any one of the senescent cell-specific antigens set forth in SEQ ID NOS: 11-23, or a fragment thereof.

The antibodies of the invention may be recombinant (e.g., chimeric or humanized), synthetic, or naturally occurring. Antibodies or antibody fragments of the invention can be recombinantly produced, or identified and isolated from a mammal that has been induced to produce or that naturally-produces antibodies that specifically bind to senescent cell-specific antigens. For example, a polypeptide having at least 80% (e.g, 85%, 90%, 95%, 99%, or 100%) amino acid sequence identity to one of the senescent cell-specific antigens set forth in SEQ ID NOS:11-23 can be administered (e.g., by injection) to a mammal (e.g., a mouse, rat, hamster, guinea pig, sheep, goat, cow, horse, non-human primate, or human) to provoke a humoral immune response against the immunizing senescent cell-specific antigen. Blood, plasma, or ascites from the immunized mammal can be screened to identify or harvest antibodies that specifically bind the immunizing senenescent cell-specific antigen. If desired, the amino acid and/or nucleic acid sequences of the antibodies produced can be determined. Furthermore, all or a portion of the nucleic acid sequences of the antibodies can be incorporated into a vector (e.g., an expression vector or a viral vector) for expression of the antibody in a cell of a subject (e.g., a mammal, such as a human) following administration of the vector to the subject, or any other uses consistent with the methods described herein.

The invention features complete antibodies, diabodies, bi-specific antibodies, antibody fragments, Fab fragments, F(ab')2 molecules, single chain Fv (scFv) molecules, tandem scFv molecules, or antibody fusion proteins. Antibodies of the invention include, e.g., the IgG, IgA, IgM, IgD, and IgE isotypes. Antibodies of the invention contain one or more CDRs or binding peptides that bind to proteins, glycoproteins, or epitopes present on the exterior or in the interior of senescent cells.

Many of the antibodies, or fragments thereof, described herein can undergo non-critical amino-acid substitutions, additions or deletions in both the variable and constant regions without loss of binding specificity or effector functions, or intolerable reduction of binding affinity (i.e., below about $10^{-7}$ M). Usually, an antibody incorporating such alterations exhibits substantial sequence identity to a reference antibody from which it is derived. Occasionally, a mutated antibody can be selected having the same specificity and increased affinity compared with a reference antibody from which it was derived. Phage-display technology offers powerful techniques for selecting such antibodies. See, e.g., Dower et al. (WO 91/17271), McCafferty et al. (WO 92/01047), and Huse (WO 92/06204), each of which is incorporated by reference herein.

Antibody Fragments

In another embodiment of the invention, an agent of the invention is a fragment of an intact antibody described herein. Antibody fragments include separate variable heavy chains, variable light chains, Fab, Fab', F(ab')$_2$, Fabc, and Fv. Fragments can be produced by enzymatic or chemical separation of intact immunoglobulins. For example, a F(ab')$_2$ fragment can be obtained from an IgG molecule by proteolytic digestion with pepsin at pH 3.0-3.5 using standard methods such as those described in Harlow and Lane, Antibodies: A Laboratory Manual, Cold Spring Harbor Pubs., N.Y. (1988). Fab fragments may be obtained from F(ab')$_2$ fragments by limited reduction, or from whole antibody by digestion with papain in the presence of reducing agents. Fragments can also be produced by recombinant DNA techniques. Segments of nucleic acids encoding selected fragments are produced by digestion of full-length coding sequences with restriction enzymes, or by de novo synthesis. Often fragments are expressed in the form of phage-coat fusion proteins. This manner of expression is advantageous for affinity-sharpening of antibodies.

Humanized Antibodies

The invention also includes humanized antibodies in which one or more of the CDRs are derived from a non-human antibody sequence (e.g., those antibodies described in Table 1), and one or more, but preferably all, of the CDRs bind specifically to a protein, glycoprotein, or epitope present on the exterior or in the interior of a senescent cell (e.g., the senescent cell-specific antigens described above (SEQ ID NOS:11-23), or a fragment thereof).

A humanized antibody contains constant framework regions derived substantially from a human antibody (termed an acceptor antibody), as well as, in some instances, a majority of the variable region derived from a human antibody. One or more of the CDRs (all or a portion thereof, as well as discreet amino acids surrounding one or more of the CDRs) are provided from a non-human antibody, such as a mouse antibody. The constant region(s) of the antibody, may or may not be present. Humanized antibodies provide several advantages over non-humanized antibodies for therapeutic or diagnostic use in humans. These include:

1) The human immune system should not recognize the framework or constant region of the humanized antibody as foreign, and therefore the antibody response against such an injected antibody should be less than against a totally foreign mouse antibody or a partially foreign chimeric antibody;

2) Because the effector portion of the humanized antibody is human, it may interact better with other parts of the human immune system; and 3) Injected mouse antibodies have been reported to have a much shorter half-life in the human circulation than the half-life exhibited by normal human antibodies (see, e.g., Shaw et al., *J. Immunol.* 138:4534-4538 (1987)). Injected humanized antibodies have a half-life essentially equivalent to naturally occurring human antibodies, allowing smaller and less frequent doses.

The substitution of one or more, e.g., mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See, e.g., Kettleborough et al., *Protein Engineering* 4:773 (1991); Kolbinger et al., *Protein Engineering* 6:971 (1993).

Suitable human antibody sequences are identified by computer comparisons of the amino acid sequences of the mouse variable regions with the sequences of known human antibodies. The comparison is performed separately for heavy and light chains but the principles are similar for each.

Methods of preparing chimeric and humanized antibodies and antibody fragments are described in U.S. Pat. Nos. 4,816,567, 5,530,101, 5,622,701, 5,800,815, 5,874,540, 5,914,110, 5,928,904, 6,210,670, 6,677,436, and 7,067,313 and U.S. Patent Application Nos. 2002/0031508, 2004/0265311, and 2005/0226876. Preparation of antibody or fragments thereof is further described in U.S. Pat. Nos. 6,331,415, 6,818,216, and 7,067,313. Each of these patents is incorporated herein by reference.

Diagnostic Agents Coupled to Agents of the Invention

Agents of the invention (e.g., peptides, polypeptides, proteins, small molecules, antibodies, or antibody fragments that target senescent cells) can be joined or coupled to any molecule that can be used to label, detect, identify, screen, or diagnose senescent cells in a mammal (e.g., a human). Diagnostic and therapeutic (e.g., cytotoxic) agents of the invention that include a detectable label can be administered in a pharmaceutical compound to a subject (e.g., a cancer patient) or these compositions can be encoded by a vector (e.g., a viral vector) and expressed in a cell of the subject following administration.

An agent of the invention that incorporates a detectable label can be used, for example, to type, grade, and track the metastasis of a tumor in a subject having cancer. The diagnostic agent can also include a therapeutic agent (e.g., cytotoxic) of the invention. In this case, the diagnostic agent facilitates the detection or measurement, or binding to senescent cells, of the therapeutic agent after administration to a subject.

A diagnostic or therapeutic agent of the invention that includes a detectable label can be produced recombinantly in vitro. In one embodiment of the invention, the detectable label is capable of detection based on an intrinsic property, e.g., fluorescence and bioluminescence, or based on its ability to bind with another molecule capable of being detected (e.g., an epitope tag, such as c-myc, hemagglutinin, and histamine tags). Peptides, polypeptides, or proteins with diagnostic properties can be altered (e.g., by making amino acid substitutions, mutations, truncations, or additions) to facilitate incorporation into an agent of the invention. Desirable alterations include, for example, changes to the amino acid sequence that facilitate protein expression, longevity, cell secretion, and detectability.

The invention also features a nucleic acid molecule encoding a peptidic detectable label as a fusion protein with an agent of the invention; the nucleic acid molecule can be incorporated into a vector (e.g., an expression vector), such that, upon expression of the agent of the invention in a cell transfected or transduced with the vector, expression of the detectable label and agent of the invention are operably linked (e.g., fused, contiguously-joined, or tethered together).

Molecules that can be used as the detectable label as discussed herein include, but are not limited to, radioactive agents, fluorescent agents, bioluminescent molecules, epitope tags, and heavy metals, each of which is discussed in detail below.

Fluorescent agents include fluorochromes, such as fluorescein isothiocyanate (FITC), allophycocyanin (APC), phycoerythrin (PE), rhodamine, and tetramethyl rhodamine isothiocyanate (TRITC). Other fluorescent molecules include green fluorescent protein (GFP; SEQ ID NO: 27), enhanced GFP (eGFP), yellow fluorescent protein (SEQ ID NO: 28; YFP), cyan fluorescent protein (SEQ ID NO: 29; CFP), and red fluorescent protein (SEQ ID NO: 30; RFP or DsRed). Each of these fluorescent molecules can be used as detectable label in a diagnostic agent of the invention. Peptidic fluorescent molecules can be recombinantly expressed in a cell (e.g., a blood cell, such as a lymphocyte) following transfection or transduction of the cell with an expression vector that encodes the nucleotide sequence of the fluorescent molecule. Upon exposure of the fluorescent molecule to a stimulating frequency of light, the fluorescent molecule will emit light at a low, medium, or high intensity that can be observed by eye under a microscope or by an optical imaging device. Exemplary fluorescent molecules suitable for use as the detectable label in a diagnostic agent of the invention are described in, e.g., U.S. Pat. Nos. 7,417,131 and 7,413,874.

Bioluminescent molecules can also be used as a detectable label incorporated into a diagnostic agent of the invention. Bioluminescent molecules, such as luciferase (e.g., firefly (SEQ ID NO: 31), *Renilla* (SEQ ID NO: 32), and

*Omphalotus* luciferase) and aequorin, emit light as part of a chemical reaction with a substrate (e.g., luciferin and coelenterazine). In one embodiment of the invention, a vector encoding a luciferase gene provides for the in vivo, in vitro, or ex vivo detection of cells (e.g., blood cells, such as lymphocytes) that have been transduced or transfected with an agent of the invention. Exemplary bioluminescent molecules suitable for use as the detectable label in a diagnostic agent of the invention, and methods for their use are described in, e.g., U.S. Pat. Nos. 5,292,658, 5,670,356, 6,171,809, and 7,183,092.

Epitope tags are short amino acid sequences, e.g., 5-20 amino acid residues in length, that can be incorporated into an agent of the invention as a detectable label to allow for detection once expressed in a cell, secreted from the cell, or bound to a target cell (e.g., a senescent cell). An agent of the invention that incorporates an epitope tag as a diagnostic agent can be detected by virtue of its interaction with an antibody, antibody fragment, or other binding molecule specific for the epitope tag. Nucleotide sequences encoding the epitope tag are produced either by cloning appropriate portions of natural genes or by synthesizing a polynucleotide that encodes the epitope tag. An antibody, antibody fragment, or other binding molecule that binds an epitope tag can directly incorporate its own detectable label (e.g., a fluorochrome, radiolabel, heavy metal, or enzyme such as horseradish peroxidase) or serve as a target for a secondary antibody, antibody fragment, or other binding molecule that incorporates such a label. Exemplary epitope tags that can be used as a detectable label include c-myc (SEQ ID NO: 24), hemagglutinin (HA; SEQ ID NO: 25), and histidine tag ($His_6$; SEQ ID NO: 26). Furthermore, fluorescent (e.g., GFP) and bioluminescent molecules, discussed above, can also serve as epitope tags, as antibodies, antibody fragments, and other binding molecules are commercially available for the detection of these moieties.

Agents of the invention (e.g., peptides, polypeptides, proteins, small molecules, antibodies, or antibody fragments that target senescent cells) can also be coupled to a chelating agent to form diagnostic agents of the invention. Diagnostic agents can be prepared by various methods depending upon the chelator chosen. A portion of an agent of the invention (e.g., a portion of a peptide, polypeptide, protein, small molecule, antibody, or antibody fragment) can be isolated from a natural source, recombinantly produced, or synthesized. The portion of an agent of the invention is most conveniently prepared by techniques generally established in the art of peptide synthesis, such as the solid-phase approach. Solid-phase synthesis involves the stepwise addition of amino acid residues to a growing peptide chain that is linked to an insoluble support or matrix, such as polystyrene. The C-terminus residue of the peptide is first anchored to a commercially available support with its amino group protected with an N-protecting agent such as a t-butyloxycarbonyl group (tBoc) or a fluorenylmethoxycarbonyl (FMOC) group. The amino-protecting group is removed with suitable deprotecting agents such as TFA in the case of tBOC or piperidine for FMOC and the next amino acid residue (in N-protected form) is added with a coupling agent such as dicyclocarbodiimide (DCC). Upon formation of a peptide bond, the reagents are washed from the support. After addition of the final residue, the agent is cleaved from the support with a suitable reagent, such as trifluoroacetic acid (TFA) or hydrogen fluoride (HF).

Agents of the invention (e.g., peptides, polypeptides, proteins, small molecules, antibodies, or antibody fragments that target senescent cells) and chelator components can be coupled to form a conjugate by reacting the free amino group of the threonine residue of a peptide portion of an agent of the invention with an appropriate functional group of the chelator, such as a carboxyl group or activated ester. For example, a conjugate may incorporate the chelator ethylenediaminetetraacetic acid (EDTA), common in the art of coordination chemistry, when functionalized with a carboxyl substituent on the ethylene chain. Synthesis of EDTA derivatives of this type are reported in Arya et al., *Bioconjugate Chemistry,* 2:323, 1991), wherein the four coordinating carboxyl groups are each blocked with a t-butyl group while the carboxyl substituent on the ethylene chain is free to react with the amino group of a peptide portion of the agent of the invention, thereby forming a conjugate.

A conjugate may incorporate a metal chelator component that is peptidic, i.e., compatible with solid-phase peptide synthesis. In this case, the chelator may be coupled to the agent of the invention (e.g., peptides, polypeptides, proteins, small molecules, antibodies, or antibody fragments that target senescent cells) in the same manner as EDTA described above or more conveniently the chelator and agent of the invention are synthesized in toto starting from the C-terminal residue of the agent and ending with the N-terminal residue of the chelator.

Conjugates may further incorporate a linking group component that serves to couple the agent of the invention (e.g., peptides, polypeptides, proteins, small molecules, antibodies, or antibody fragments that target senescent cells) to the chelator while not adversely affecting either the targeting function of the agent or the metal binding function of the chelator. Suitable linking groups include amino acid chains and alkyl chains functionalized with reactive groups for coupling to both the agent and the chelator. An amino acid chain is the preferred linking group when the chelator is peptidic so that the conjugate can be synthesized in toto by solid-phase techniques.

An alkyl chain linking group may be incorporated in the conjugate by reacting the amino group of the threonine residue of a peptide portion of an agent of the invention (e.g., peptides, polypeptides, proteins, small molecules, antibodies, or antibody fragments that target senescent cells) with a first functional group on the alkyl chain, such as a carboxyl group or an activated ester. Subsequently the chelator is attached to the alkyl chain to complete the formation of the conjugate by reacting a second functional group on the alkyl chain with an appropriate group on the chelator. The second functional group on the alkyl chain is selected from substituents that are reactive with a functional group on the chelator while not being reactive with the threonine residue of the agent. For example, when the chelator incorporates a functional group such as a carboxyl group or an activated ester, the second functional group of the alkyl chain linking group can be an amino group. It will be appreciated that formation of the conjugate may require protection and deprotection of the functional groups present in order to avoid formation of undesired products. Protection and deprotection are accomplished using protecting groups, reagents, and protocols common in the art of organic synthesis. Particularly, protection and deprotection techniques employed in solid phase peptide synthesis described above may be used.

An alternative chemical linking group to an alkyl chain is polyethylene glycol (PEG), which is functionalized in the same manner as the alkyl chain described above for incorporation in the conjugates. It will be appreciated that linking groups may alternatively be coupled first to the chelator and then to the agent of the invention (e.g., peptides, polypeptides, proteins, small molecules, antibodies, or antibody fragments that target senescent cells).

In accordance with one aspect of the invention, agent-chelator conjugates of the invention incorporate a diagnostically useful metal capable of forming a complex. Suitable metals include, e.g., radionuclides, such as technetium and rhenium in their various forms (e.g., $^{99m}TcO^{3+}$, $^{99m}TcO_2^+$, $ReO^{3+}$, and $ReO_2^+$). Incorporation of the metal within the conjugate can be achieved by various methods common in the art of coordination chemistry. When the metal is technetium-99 m, the following general procedure may be used to form a technetium complex. An agent-chelator conjugate solution is formed initially by dissolving the conjugate in aqueous alcohol such as ethanol. The solution is then degassed to remove oxygen then thiol-protecting groups are removed with a suitable reagent, for example, with sodium hydroxide, and then neutralized with an organic acid, such as acetic acid (pH 6.0-6.5). In the labeling step, a stoichiometric excess of sodium pertechnetate, obtained from a molybdenum generator, is added to a solution of the conjugate with an amount of a reducing agent such as stannous chloride sufficient to reduce technetium and heated. The labeled conjugate may be separated from contaminants $^{99m}TcO_4^-$ and colloidal $^{99m}TcO_2$ chromatographically, for example, with a C-18 Sep Pak cartridge.

In an alternative method, labeling of the agent of the invention can be accomplished by a transchelation reaction. The technetium source is a solution of technetium complexed with labile ligands facilitating ligand exchange with the selected chelator. Suitable ligands for transchelation include tartarate, citrate, and heptagluconate. In this instance the preferred reducing reagent is sodium dithionite. It will be appreciated that the conjugate may be labeled using the techniques described above, or alternatively the chelator itself may be labeled and subsequently coupled to the agent of the invention to form the conjugate; a process referred to as the "prelabeled ligand" method.

Another approach for labeling agents of the invention (e.g., peptides, polypeptides, proteins, small molecules, antibodies, or antibody fragments that target senescent cells) involves immobilizing the agent-chelator conjugate on a solid-phase support through a linkage that is cleaved upon metal chelation. This is achieved when the chelator is coupled to a functional group of the support by one of the complexing atoms. Preferably, a complexing sulfur atom is coupled to the support which is functionalized with a sulfur protecting group such as maleimide.

When labeled with a diagnostically useful metal, agent-chelator conjugates of the invention can be used to detect tissue at risk of developing cancer (e.g., lung cancer, breast cancer, colon cancer, and prostate cancer), age-related diseases (e.g., cardiovascular disease, cerebrovascular disease, or Alzheimer's disease), tobacco-related diseases (e.g., emphysema, aortic aneurysms, esophageal cancer, or squamous cell cancer of the head and neck), or other diseases and disorders relating to or caused by cellular senescence by procedures established in the art of diagnostic imaging. An agent labeled with a radionuclide metal, such as technetium-99 m, may be administered to a mammal (e.g., a human) by intravenous injection in a pharmaceutically acceptable solution such as isotonic saline, or by other methods described herein. The amount of a labeled agent of the invention (e.g., peptides, polypeptides, proteins, small molecules, antibodies, or antibody fragments that target senescent cells) appropriate for administration is dependent upon the distribution profile of the chosen conjugate in the sense that a rapidly cleared agent may be administered at higher doses than one that clears less rapidly. Unit doses acceptable for imaging tissues that contain senescent cells are in the range of, e.g., 5-40 mCi for a 70 kg individual. In vivo distribution and localization can be tracked by standard techniques described herein at an appropriate time subsequent to administration; typically between 30 minutes and 180 minutes depending upon the rate of accumulation at the target site with respect to the rate of clearance at non-target tissue.

Therapeutic or Cytotoxic Agents Coupled to Agents of the Invention

Any of the agents of the invention (e.g., peptides, polypeptides, proteins, small molecules, antibodies, or antibody fragments that target senescent cells) can be coupled to any known cytotoxic or therapeutic moiety. Examples include, e.g., antineoplastic agents such as: Acivicin; Aclarubicin; Acodazole Hydrochloride; Acronine; Adozelesin; Adriamycin; Aldesleukin; Altretamine; Ambomycin; A. metantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Camptothecin; Caracemide; Carbetimer; Carboplatin; Carmustine; Carubicin Hydrochloride; Carzelesin; Cedefingol; Chlorambucil; Cirolemycin; Cisplatin; Cladribine; Combretestatin A-4; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Dexormaplatin; Dezaguanine; Dezaguanine Mesylate; Diaziquone; Docetaxel; Dolasatins; Doxorubicin; Doxorubicin Hydrochloride; Droloxifene; Droloxifene Citrate; Dromostanolone Propionate; Duazomycin; Edatrexate; Eflornithine Hydrochloride; Ellipticine; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 1131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Homocamptothecin; Hydroxyurea; Idarubicin Hydrochloride; Ifosfamide; Ilmofosine; Interferon Alfa-2a; Interferon Alfa-2b; Interferon Alfa-nl; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; PeploycinSulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Rhizoxin; Rhizoxin D; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2' Deoxyformycin; 9-aminocamptothecin; raltitrexed; N-propargyl-5,8-dideazafolic acid; 2chloro-2'-arabino-fluoro-2'-deoxyadenosine; 2-chloro-2'-deoxyadenosine; anisomycin; trichostatin A; hPRL-G129R; CEP-751; linomide; sulfur mustard; nitrogen mustard (mechlor ethamine); cyclophosphamide; melphalan; chlorambucil; ifosfamide; busulfan; N-methyl-Nnitrosourea (MNU); N,N'-Bis(2-chloroethyl)-N-nitrosourea (BCNU); N-(2-chloroethyl)-N' cyclohexyl-N-nitrosourea (CCNU); N-(2-chloroethyl)-N'-(trans-4-methylcyclohexyl-N-nitrosourea (MeCCNU); N-(2-chloroethyl)-N'-(diethyl) ethylphosphonate-N-nitrosourea (fotemustine); streptozotocin; diacarbazine (DTIC); mitozolomide; temozolomide; thiotepa; mitomycin C; AZQ; adozelesin; Cisplatin; Carboplatin; Ormaplatin; Oxaliplatin; C1-973; DWA 2114R; JM216; JM335; Bis (platinum); tomudex; azacitidine; cytarabine; gemcitabine; 6-Mercaptopurine; 6-Thioguanine; Hypoxanthine; teniposide 9-amino camptothecin; Topotecan; CPT-11; Doxorubicin; Daunomycin; Epirubicin; darubicin; mitoxantrone; losoxantrone; Dactinomycin (Actinomycin D); amsacrine; pyrazoloacridine; all-trans retinol; 14-hydroxy-retro-retinol; all-trans retinoic acid; N-(4-Hydroxyphenyl) retinamide; 13-cis retinoic acid; 3-Methyl TTNEB; 9-cis retinoic acid; fludarabine (2-F-ara-AMP); or 2-chlorodeoxyadenosine (2-Cda).

Other therapeutic compounds include, but are not limited to, 20-pi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; argininedeaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bleomycin A2; bleomycin B2; bropirimine; budotitane; buthionine sulfoximine; calcipotriol; calphostin C; camptothecin derivatives (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; 2'deoxycoformycin (DCF); deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; hereguin; hexamethylene bisacetamide; homoharringtonine (HHT); hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; rnerbarone; meterelin; methioninase; metoclopramide; MIF inhibitor; ifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; roglitimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

One or more of the agents of the invention (e.g., peptides, polypeptides, proteins, small molecules, antibodies, or antibody fragments that target senescent cells) can also be coupled to a lytic peptide. Such lytic peptides induce cell death and include, but are not limited to, streptolysin O; stoichactis toxin; phallolysin; *staphylococcus* alpha toxin; holothurin A; digitonin; melittin; lysolecithin; cardiotoxin; and cerebratulus A toxin (Kern et al., *J. Biol. Chem.* 253 (16):5752-5757, 1978). Agents of the invention can also be coupled to a synthetic peptide that shares some sequence homology or chemical characteristics with any of the naturally occurring peptide lysins; such characteristics include, but are not limited to, linearity, positive charge, amphipathicity, and formation of alpha-helical structures in a hydrophobic environment (Leuschner et al., *Biology of Reproduction* 73:860-865, 2005). Agents of the invention can also be coupled to an agent that induces complement-mediated cell lysis such as, for example, the immunoglobulin $F_c$ subunit. Agents of the invention can also coupled to any member of the phospholipase family of enzymes (including phospholipase A, phospholipase B, phospholipase C, or phospholipase D) or to a catalytically-active subunit thereof.

Agents of the invention (e.g., peptides, polypeptides, proteins, small molecules, or antibody fragments that target senescent cells) can also be coupled to a radioactive agent, including, but not limited to: Fibrinogen $^{125}$I; Fludeoxyglucose $^{18}$F; Fluorodopa $^{18}$F; Insulin $^{125}$I; Insulin $^{131}$I; lobenguane $^{123}$I; Iodipamide Sodium $^{131}$I; Iodoantipyrine $^{131}$I; Iodocholesterol $^{131}$I; lodohippurate Sodium $^{123}$I; Iodohippurate Sodium $^{125}$I; Iodohippurate Sodium $^{131}$I; Iodopyracet $^{125}$I; Iodopyracet $^{131}$I; lofetamine Hydrochloride $^{123}$I; lomethin $^{125}$I; Iomethin $^{131}$I; Iothalamate Sodium $^{125}$I; Iothalamate Sodium $^{131}$I; tyrosine $^{131}$I; Liothyronine $^{125}$I; Liothyronine $^{131}$I; Merisoprol Acetate $^{197}$Hg; Merisoprol Acetate $^{203}$Hg; Merisoprol $^{197}$Hg; Selenomethionine $^{75}$Se; Technetium $^{99m}$Tc Antimony Trisulfide Colloid; Technetium $^{99m}$Tc Bicisate; Technetium $^{99m}$Tc Disofenin; Technetium $^{99m}$Tc Etidronate; Technetium $^{99m}$Tc Exametazime; Technetium $^{99m}$Tc Furifosmin; Technetium $^{99m}$Tc Gluceptate; Technetium $^{99m}$Tc Lidofenin; Technetium $^{99m}$Tc Mebrofenin; Technetium $^{99m}$Tc Medronate; Technetium $^{99m}$Tc Medronate Disodium; Technetium $^{99m}$Tc Mertiatide; Technetium $^{99m}$Tc Oxidronate; Technetium $^{99m}$Tc Pentetate; Technetium $^{99m}$Tc Pentetate Calcium Trisodium; Technetium $^{99m}$Tc Sestamibi; Technetium $^{99m}$Tc Siboroxime; Technetium $^{99m}$Tc; Succimer; Technetium $^{99m}$Tc Sulfur Colloid; Technetium $^{99m}$Tc Teboroxime; Technetium $^{99m}$Tc Tetrofosmin; Technetium $^{99m}$Tc Tiatide; Thyroxine $^{125}$I; Thyroxine $^{131}$I; Tolpovidone $^{131}$I; Triolein $^{125}$I; or Triolein $^{131}$I.

Therapeutic or cytotoxic agents may further include, for example, anti-cancer Supplementary Potentiating Agents, including, but not limited to: Tricyclic anti-depressant drugs (e.g., imipramine, desipramine, amitryptyline, clomipramine, trimipramine, doxepin, nortriptyline, protriptyline, amoxapine, and maprotiline); non-tricyclic anti-depressant drugs (e.g., sertraline, trazodone, and citalopram); $Ca^{2+}$ antagonists (e.g., verapamil, nifedipine, nitrendipine, and caroverine); Calmodulin inhibitors (e.g., prenylamine, trifluoroperazine, and clomipramine); Amphotericin B; Triparanol analogs (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL.

The agents of the invention (e.g., peptides, polypeptides, proteins, small molecules, antibodies, or antibody fragments that target senescent cells) can also be administered with cytokines, such as granulocyte colony stimulating factor, or anticancer agents used in anti-cancer cocktails including, e.g., those shown with their MTDs in parentheses: gemcitabine (1000 mg/m$^2$); methotrexate (15 gm/m$^2$ i.v.+leuco. <500 mg/m$^2$ i.v. w/o leuco); 5-FU (500 mg/m$^2$/day×5 days); FUDR (100 mg/kg×5 in mice, 0.6 mg/kg/day in human i.a.); FdUMP; Hydroxyurea (35 mg/kg/d in man); Docetaxel (60-100 mg/m$^2$); discodermolide; epothilones; vincristine (1.4 mg/m$^2$); vinblastine (escalating: 3.3-11.1 mg/m$^2$, or rarely to 18.5 mg/m$^2$); vinorelbine (30 mg/m$^2$/wk); metapac; irinotecan (50-150 mg/m$^2$,1×/wk depending on patient response); SN-38 (~100 times more potent than Irinotecan); 10-OH campto; topotecan (1.5 mg/m$^2$/day in humans, 1×iv LD1Omice=75 mg/m$^2$); etoposide (100 mg/m$^2$ in man); adriamycin; flavopiridol; Cis-Pt (100 mg/m$^2$ in man); carbo-Pt (360 mg/m$^2$ in man); bleomycin (20 mg/m2); mitomycin C (20 mg/m$^2$); mithramycin (30 sug/kg); capecitabine (2.5 g/m$^2$ orally); cytarabine (100 mg/m$^2$/day); 2-Cl-2'deoxyadenosine; Fludarabine-P04 (25 mg/m$^2$/day, ×5 days); mitoxantrone (12-14 mg/m$^2$); mitozolomide (>400 mg/m$^2$); Pentostatin; or Tomudex.

Any of the agents of the invention (e.g., peptides, polypeptides, proteins, small molecules, antibodies, or antibody fragments that target senescent cells) can be coupled to an antimetabolic agent. Antimetabolic agents include, but are not limited to, the following compounds and their derivatives: azathioprine, cladribine, cytarabine, dacarbazine, fludarabine phosphate, fluorouracil, gencitabine chlorhydrate, mercaptopurine, methotrexate, mitobronitol, mitotane, proguanil chlorohydrate, pyrimethamine, raltitrexed, trimetrexate glucuronate, urethane, vinblastine sulfate, vincristine sulfate, etc. In other embodiments, the agents of the invention can be coupled to a folic acid-type antimetabolite, a class of agents that includes, for example, methotrexate, proguanil chlorhydrate, pyrimethanime, trimethoprirne, or trimetrexate glucuronate, or derivatives of these compounds.

In another embodiment, any of the agents of the invention (e.g., peptides, polypeptides, proteins, small molecules, antibodies, or antibody fragments that target senescent cells) can be coupled to a member of the anthracycline family of neoplastic agents, including but not limited to aclarubicine chlorhydrate, daunorubicine chlorhydrate, doxorubicine chlorhydrate, epirubicine chlorhydrate, idarubicine chlorhydrate, pirarubicine, or zorubicine chlorhydrate; a camptothecin, or its derivatives or related compounds, such as 10, 11 methylenedioxycamptothecin; or a member of the maytansinoid family of compounds, which includes a variety of structurally-related compounds, e.g., ansamitocin P3, maytansine, 2'-N-demethylmaytanbutine, and maytanbicyclinol.

Any of the agents of the invention (e.g., peptides, polypeptides, proteins, small molecules, antibodies, or antibody fragments that target senescent cells) can be modified or labeled to facilitate diagnostic or therapeutic uses. Detectable labels such as a radioactive, fluorescent, heavy metal, or other agents may be bound to any of the agents of the invention. Single, dual, or multiple labeling of an agent may be advantageous. For example, dual labeling with radioactive iodination of one or more residues combined with the additional coupling of, for example, $^{90}$Y via a chelating group to amine-containing side or reactive groups, would allow combination labeling. This may be useful for specialized diagnostic needs such as identification of widely dispersed small neoplastic cell masses.

Agents of the invention (e.g., peptides, polypeptides, proteins, small molecules, antibodies, or antibody fragments that target senescent cells), or analogs thereof, can also be modified, for example, by halogenation of the tyrosine residues of the peptide component. Halogens include fluorine, chlorine, bromine, iodine, and astatine. Such halogenated agents may be detectably labeled, e.g., if the halogen is a radioisotope, such as, for example, $^{18}$F, $^{75}$Br, $^{77}$Br, $^{122}$I, $^{123}$I, $^{124}$I, $^{125}$I, $^{129}$I, $^{131}$I, or $^{211}$At. Halogenated agents of the invention contain a halogen covalently bound to at least one amino acid, and preferably to D-Tyr residues in each agent molecule. Other suitable detectable modifications include binding of other compounds (e.g., a fluorochrome such as fluorescein) to a lysine residue of the agent of the invention, or analog, particularly an agent or analog having a linker including lysines.

Radioisotopes for radiolabeling any of the agents of the invention (e.g., peptides, polypeptides, proteins, small molecules, antibodies, or antibody fragments that target senescent cells) include any radioisotope that can be covalently bound to a residue of the peptide component of the agent of the invention or analog thereof. The radioisotopes can be selected from radioisotopes that emit either beta or gamma radiation, or alternatively, any of the agents of the invention can be modified to contain chelating groups that, for example, can be covalently bonded to lysine residue(s) of the analog. The chelating groups can then be modified to contain any of a variety of radioisotopes, such as gallium, indium, technetium, ytterbium, rhenium, or thallium (e.g., $^{125}$I, $^{67}$Ga, $^{111}$In, $^{99m}$Tc, $^{169}$Yb, $^{186}$Re).

When one or more of the agents of the invention (e.g., peptides, polypeptides, proteins, small molecules, antibodies, or antibody fragments that target senescent cells) is modified by attachment of a radioisotope, preferable radioisotopes are those having a radioactive half-life corresponding to, or longer than, the biological half-life of the agent used. More preferably, the radioisotope is a radioisotope of a halogen atom (e.g. a radioisotope of fluorine, chlorine, bromine, iodine, and astatine), even more preferably $^{75}$Br, $^{77}$Br, $^{76}$Br, $^{122}$I, $^{123}$I, $^{124}$I, $^{125}$I, $^{129}$I, $^{131}$I, or $^{211}$At.

Agents of the invention (e.g., peptides, polypeptides, proteins, small molecules, antibodies, or antibody fragments that target senescent cells) coupled to radioactive metals are useful in radiographic imaging or radiotherapy. Preferred radioisotopes also include $^{99m}$Tc, $^{51}$Cr, $^{67}$Ga, $^{68}$Ga, $^{111}$In, $^{168}$Yb, $^{140}$La, $^{90}$Y, $^{88}$Y, $^{153}$Sm, $^{156}$Ho, $^{165}$Dy, $^{64}$Cu, $^{97}$Ru, $^{103}$Ru, $^{186}$Re, $^{188}$Re, $^{203}$Pb, $^{211}$Bi, $^{212}$Bi, $^{213}$Bi, and $^{214}$Bi. The choice of metal can be determined based on the desired therapeutic or diagnostic application.

The agents of the invention (e.g., peptides, polypeptides, proteins, small molecules, antibodies, or antibody fragments that target senescent cells), when coupled to a metal component, are useful as diagnostic and/or therapeutic agents. A detectable label may be a metal ion from heavy elements or rare earth ions, such as $Gd^{3+}$, $Fe^{3+}$, $Mn^{3+}$, or $Cr^{2+}$. Conjugates that include paramagnetic or superparamagnetic metals are useful as diagnostic agents in MRI imaging applications. Paramagnetic metals that can be coupled to the agents of the invention include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). Preferably, the polymer has a relaxtivity of at least 10, 12, 15, or 20 $mM^{-1}$ $sec^{-1}$ $Z^{-1}$, wherein Z is the concentration of paramagnetic metal.

Chelating groups may be used to indirectly couple detectable labels or other molecules to an agents of the invention (e.g., a peptide, polypeptide, protein, small molecule, antibody, or antibody fragment). Chelating groups can link agents of the invention with radiolabels, such as a bifunctional stable chelator, or can be linked to one or more terminal or internal amino acid reactive groups. Conjugates can be linked via an isothiocyanate β-Ala or appropriate non α-amino acid linker which prevents Edman degradation. Examples of chelators known in the art include, for example, the ininocarboxylic and polyaminopolycarboxylic reactive groups, ininocarboxylic and polyaminopolycarboxylic reactive groups, diethylenetriaminepentaacetic acid (DTPA), and 1,4,7,10-tetraazacyclododecane-1,4,7,10-tetraacetic acid (DOTA).

An agent of the invention (e.g., peptides, polypeptides, proteins, small molecules, antibodies, or antibody fragments that target senescent cells) can also be coupled directly to a cytotoxic or therapeutic agent using known chemical methods, or the two moieties can be coupled via an indirect linkage, such as through a chelating group. For example, the agent can be attached to a chelating group that is attached to the cytotoxic or therapeutic agent. Chelating groups include, but are not limited to, ininocarboxylic and polyaminopolycarboxylic reactive groups, diethylenetriaminepentaacetic acid (DTPA), and 1,4,7,10-tetraazacyclododecane-1,4,7,10-tetraacetic acid (DOTA). For general methods, see, e.g., Liu et al., *Bioconjugate Chem.* 12(4):653, 2001; Cheng et al., WO 89/12631; Kieffer et al., WO 93/12112; Albert et al., U.S. Pat. No. 5,753,627; and WO 91/01144 (each of which are hereby incorporated by reference).

When coupled to a therapeutic or cytotoxic agent, specific targeting by the agents of the invention (e.g., peptides, polypeptides, proteins, small molecules, antibodies, or antibody fragments that target senescent cells) allows selective destruction of senescent cells. For example, the agents of the invention can be used to target and destroy senescent cells of the lung, breast, prostate, and colon in order to prevent, stabilize, inhibit the progression of, or treat cancers originating in these organs. Also, for example, the agents of the invention can be used to target and destroy senescent cells of the vasculature, brain, liver, kidney, heart, lung, prostate, colon, nasopharynx, oropharynx, larynx, bronchus, and skin in order to prevent, stabilize, inhibit the progression of, or treat age-related diseases or tobacco-related diseases or conditions relating to these organs. Any of the agents of the invention (e.g., peptides, polypeptides, proteins, small molecules, antibodies, or antibody fragments that target senescent cells) can be administered to a mammalian subject, such as a human, directly or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, for example, in *Remington's Pharmaceutical Sciences*, (18$^{th}$ edition), ed. A. Gennaro, 1990, Mack Publishing Company, Easton, Pa.

Agents of the Invention for Use in Cellular Therapy Applications

One or more agents of the invention (e.g., peptides, polypeptides, proteins, small molecules, antibodies, or antibody fragments that target senescent cells) can be used to improve the efficacy of a cellular therapy provided to a patient (e.g., a mammal, such as a human) in need thereof by depleting (i.e., killing) one or more, all, or substantially all (e.g., 1%, 2%, 3%, 4%, 5%, 6%, 7%, 8%, 9%, 10%, 20%, 30%, 40%, 50%, 60%, 70%, 80%, 90%, 95%, 99% or more) senescent cells in the transferred donor cells, tissue, or organ prior to, concurrent with, or following administration of the cellular therapy. Alternatively, a patient (e.g., a mammal, such as a human) may be treated with one or more agents of the invention prior to, concurrent with, or following administration of the cellular therapy. Cellular therapies include, without limitation, the autologous, allogeneic, syngeneic, or xenogeneic transplantation or engraftment of cells (e.g., blood, pancreatic islet cells, and stem cells (e.g., hematopoietic stem cells (HSC), umbilical cord blood stem cells (see, e.g., US Patent Application Publication 2002/0164794), pluripotent stem cells (e.g., hox11-expressing pluripotent stem cells described in US Patent Application Publication 2005/0158288), multipotent stem cells, and totipotent stem cells), tissues (e.g., skin and adipose tissue), or organs (e.g., kidney, liver, heart, and lung) to a patient (e.g., a mammal, such as a human) in need thereof. Cellular therapies (e.g., cell (e.g., stem cells), tissue, or organ transplantation or engraftment) are currently being developed for a wide range of therapeutic indications for degenerative and pathologic diseases, such as osteoarthritis (see, e.g., U.S. Patent Application Publication No. 2007/0264238), ischemia and cardiac tissue damage, such as that caused by myocardial infarction (see, e.g., Dzau et al., U.S. Patent Application Publication No. 2007/0259425), type I and type II diabetes (see, e.g., Uchida et al., U.S. Patent Application Publication No. 2007/0212732), renal dysfunction and multi-organ failure (see, e.g., Westenfelder, U.S. Patent Application Publication No. 2007/0178071), and neurodegenerative diseases (see, e.g., Kim et al., U.S. Patent Application Publication No. 2007/0054399). The preceding U.S. patent application Publications are hereby incorporated by reference in their entirety.

Administration and Dosages

Pharmaceutical formulations of a therapeutically effective amount of an agent of the invention (e.g., peptides, polypeptides, proteins, small molecules, antibodies, or antibody fragments that target senescent cells), or pharmaceutically acceptable salt-thereof, can be administered orally, parenterally (e.g., intramuscular, intraperitoneal, intravenous, or subcutaneous injection, inhalation, intradermally, optical drops, or implant), nasally, vaginally, rectally, sublingually, or topically. The pharmaceutical formulation can include the agent of the invention in admixture with a pharmaceutically acceptable carrier adapted for the route of administration.

Methods well known in the art for making pharmaceutical formulations can be found, for example, in *Remington's Pharmaceutical Sciences* (18$^{th}$ edition), ed. A. Gennaro, 1990, Mack Publishing Company, Easton, Pa. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphthalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the agents of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

Compositions for rectal or vaginal administration are preferably suppositories which may contain, in addition to active substances, excipients such as coca butter or a suppository wax. Compositions for nasal or sublingual administration are also prepared with standard excipients known in the art. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops or spray, or as a gel.

The amount of active ingredient in the compositions of the invention can be varied. One skilled in the art will appreciate that the exact individual dosages may be adjusted somewhat depending upon a variety of factors, including the agent being administered, the time of administration, the route of administration, the nature of the formulation, the rate of excretion, the nature of the subject's conditions, and the age, weight, health, and gender of the patient. In addition, the severity of the condition targeted by an agent of the invention will also have an impact on the dosage level. Generally, dosage levels of an agent of the invention of between 0.1 µg/kg to 100 mg/kg of body weight are administered daily as a single dose or divided into multiple doses. Preferably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage can be determined by the attending physician in consideration of the above-identified factors.

An agent of the invention (e.g., a peptide, polypeptide, protein, small molecule, antibody, or antibody fragment that targets senescent cells) can be administered in a sustained release composition, such as those described in, for example, U.S. Pat. Nos. 5,672,659, 5,595,760. The use of immediate or sustained release compositions depends on the type of condition being treated. If the condition consists of an acute or over-acute disorder, a treatment with an immediate release form will be preferred over a prolonged release composition. Alternatively, for preventative or long-term treatments, a sustained released composition will generally be preferred.

An agent of the invention (e.g., a peptide, polypeptide, protein, small molecule, antibody, or antibody fragment that targets senescent cells) can be prepared in any suitable manner. The agent may be isolated from naturally-occurring sources, recombinantly produced, or produced synthetically, identified from a library of small molecules, or produced by a combination of these methods. The synthesis of short peptides is well known in the art. See e.g., Stewart et al., Solid Phase Peptide Synthesis (Pierce Chemical Co., 2d ed., 1984). A peptide portion of any of the agents of the invention can be synthesized according to standard peptide synthesis methods known in the art.

The present invention is illustrated by the following examples, which are in no way intended to be limiting of the invention.

EXAMPLES

Example 1

Discovery of Agents that Bind Senescent Cells

Phage Selection Technique

Normal skin cell line CCD-1070Sk was obtained from American Type Culture Collection (Bethesda, Md.). The cells were grown in Eagle's Minimal Essential medium with Earle's BSS, 2 mM L-glutamine, 1.0 mM Sodium pyruvate, 0.1 mM nonessential amino acids and 1.5 g/L sodium bicarbonate supplemented with 10% fetal bovine serum.

Cells were sub-cultured every 4-5 days till they became senescent. Cell senescence was confirmed by senescence-associated beta-galactosidase staining.

An M13 phage peptide library, Ph.D.-12, was obtained from New England BioLabs (Beverly, Mass.), which displays random 12-mer peptides.

For the selection step for round 1, an aliquot (10 µL) of the Ph.D.-12 complete phage library was incubated with $5\times10^5$ cells of senescent fibroblasts in 1 mL PBS/0.5% BSA for ~3.5 hours at room temperature with slow shaking on Lab-Quake. At the end of the incubation, the cells were pelleted in a microcentrifuge at 1500 RPM for 2 minutes and the supernatant removed. Cells were washed with PBS/1.0% BSA/0.5% Tween (wash buffer) for a total of 4 washes using fresh tubes between washes. Phage that bound to the target cells were eluted with 200 µL of 0.2 M glycine (pH 2.2) for 8 minutes then neutralized with 30 µL of 1 M Tris-HCl (pH 9.0). The number of phage bound was determined and the remaining eluate was amplified.

From the amplified eluate from Round 1, an aliquot ($2\times10^{11}$ phage) was used for subtraction panning against normal skin fibroblasts. The phage were incubated with $2\times10^6$ cells of normal skin fibroblast (CC D 1070 sk) at room temperature for 60 minutes at room temperature with slow shaking in PBS with 0.5% BSA. At the end of incubation, the cells were pelleted in a microcentrifuge at 1500 RPM for 2 minutes and the supernatant recovered. The supernatant was used to resuspend another $2\times10^6$ subtraction cells. This subtraction step was repeated 3 times for each round.

After the final subtraction step in each round, the recovered phage supernatant was used to suspend $5\times10^5$ selection cells. The bound phage were recovered and amplified as described above. The process was repeated for a total of 5 rounds of selection. After the fifth round of selection, phage were titered and 20 well-separated plaques were picked, amplified, and sequenced.

Results:

Three consensus sequences were obtained from the phage display selection procedure. These correspond to the SEQ ID NOS:1-3. SEQ ID NO:1 represented 9/20 clones, SEQ ID NO:2 represented 6/20 clones, and SEQ ID NO:3 represented 2/20 clones.

Example 2

Human Study to Test the Prognostic Use of a Senescent Cell Binding Agent Labeled with a Radioisotope; Using a Senescent Cell Detecting Radiotracer to Predict Cancer Risk This study is designed to show that noninvasive, in vivo imaging of senescent cell content can be used to predict cancer risk in smokers. Six-hundred subjects will be enrolled. Eighty percent of these subjects will be smokers;

twenty percent will be nonsmokers. Subjects less than 18 years of age, subjects with a history of cancer, and pregnant subjects will be excluded. The anticipated mean age of study subjects is 55 years. Each study subject will undergo scintigraphic imaging using a radio-labeled peptide of the invention (SEQ ID NO:1) as the radiopharmaceutical. The radiopharmaceutical will be prepared by reacting peptide-gly-gly-gly-ser-DTPA with 111-In chloride. Each study subject will receive an intravenously administered dose of 5 mCi of 111-In labeled peptide. Anterior and posterior whole body planar images of the subjects will be obtained at 24 and 48 hours following administration of the radio-labeled peptide. SPECT imaging of the chest will also be obtained at 24 and 48 hours following administration of the radio-labeled peptide. Scintigraphic images will be acquired on a SPECT/CT camera using a medium energy collimator. Two radiologists will read the SPECT/CT study of each subject. Regions of interest will be drawn around each lung and the mediastinum. The activity within each region will be determined for each subject. Subjects will be followed for two years and monitored for the incidence of lung cancer. Kaplan-Meier curves will be drawn for the study population based upon cancer free survival. An optimal threshold of activity within the regions of interest will be determined such as to divide subjects that develop cancer from subjects who don't; a Kaplan-Meier curve will be drawn for the set of subjects with activity levels above the threshold and a Kaplan-Meier curve will be drawn for subjects with activity levels below the threshold level. We expect to observe development of lung cancer in approximately twenty subjects. Activity in pulmonary regions of interest will be significantly higher in smokers than nonsmokers. Smokers who develop lung cancer will have significantly higher activity in pulmonary regions of interest than smokers who do not develop lung cancer. Cancer-free survival curves will be significantly different for subjects with a pulmonary region of interest activity level above the threshold value than for subjects with activities below the threshold value.

Example 3

Using Senescent Cell Binding Agents Coupled to Cytotoxic Agents to Eliminate Senescent Cells: Effect on Subsequent Development of Cancer The purpose of this study is to show that elimination of some senescent cells from an organism using the agents of the invention (e.g., peptides, polypeptides, proteins, small molecules, antibodies, or antibody fragments that target senescent cells) will reduce the risk of subsequently developing cancer. For example, a senescent cell binding peptide. (SEQ ID NO:1) will be conjugated to a cytotoxic peptide having the sequence KFAKFAKKFAKFAKKFAKFAK (SEQ ID NO:4; Leuschner and Hansel, Biology of Reproduction 73:860-865) via an amino acid linker sequence (e.g., a linker sequence selected from GGGC (SEQ ID NO:9), GGGS (SEQ ID NO:10), and GG) at the C terminus of the senescent cell binding peptide. Study subjects will consist of 60 BALB/c mice, mean age 6 mo which includes 30 experimental animals and 30 controls. Experimental animals will receive an intravenously administered dose of 0.2 mg/Kg of body weight of senescent cell binding peptide conjugate once every three months for one year. Control animals will receive an equal dose of a 37 amino acid control peptide. Kaplan-Meier curves representing tumor free survival will be constructed for each group of mice. Approximately 30% of control mice will develop tumors by the end of the study period. The study is expected to show significantly longer tumor free survival in the experimental group compared to the control group.

Example 4

Reduction of Senescent Cell Content in Diabetic Mice by Treatment with a Senescent Cell Cytotoxic Agent Diabetes is induced in female CD-1 mice, 5-7 weeks old and 25-35 g in body weight, by intraperitoneal injection of 200 mg/Kg body weight of streptozotocin dissolved in sodium citrate saline buffer (pH 4.5). Tail vein blood glucose will be measured 5 days after injection to ensure induction of diabetes. Diabetic mice will be maintained at constant temperature (23° C.) with 12 hour light and 12 hour dark cycles for 16 weeks following confirmation of diabetes. Seven diabetic mice will receive a weekly tail vein injection of a senescent cell cytotoxic agent (SenL; SEQ ID NO:6; GVYHFAPLTPTPGGGSKFAKFAKKFAKFAK; 300 µg/dose), comprising a senescent cell binding sequence linked to a lytic peptide sequence during the 16 weeks. Seven control animals will receive an equivalent volume TV injection of normal saline. At the end of 16 weeks, all animals will be sacrificed. Tissue cross sections will be prepared from aorta, lung, liver, and heart from snap frozen tissue. Tissue samples will be stained for SA-β-gal activity using the method of Campisi et al. Percentage of SA-β-gal positive cells will be determined for each tissue sample from each animal by counting 1000 cells in each of four random microscopic fields for each tissue sample. A two-tailed I-test will be used to evaluate the loss of senescent cells in the tissues of diabetic mice treated with senescent cell cytotoxic agent relative to the loss of senescent cells in the tissues of diabetic control mice.

Example 5

Enhancement of Stem Cell Treatments by Pre-Treatment with Senescent Cell Binding Agents Coupled to Cytotoxic Agents: Effects on Subsequent Stem Cell Engraftment The following experiment can be used to show that exogenously administered stem cells engraft at higher rates into damaged tissue if the treated organism undergoes pre-treatment with a senescent cell cytotoxic agent of the invention (e.g., a peptide agent) to reduce the content of senescent cells in the damaged tissue compartment. Removal of senescent cells increases the engraftment of stem cells into damaged tissue.

Balb-C mice will undergo left anterior descending (LAD) artery ligation for 60 minutes to induce myocardial infarction. The mice will be pre-anesthetized in an isoflurane inhalation chamber and receive an i.p. injection of sodium pentobarbital (25 mg/kg). The animals will be intubated and ventilated for the duration of the procedure. The LAD artery will be identified following left lateral thoracotomy and pericardectomy. Ligation will be performed on the proximal 2 mm portion of the LAD using a 9-0 ethilon stitch. Mice will be maintained at 23° C. with 12 hour light and 12 hour dark cycles for 6 days. Seven surviving mice will be used as experimental animals and seven will be used as control animals. Experimental mice will receive tail vein injections of a senescent cell cytotoxic agent conjugated to a lytic peptide sequence (SEQ ID NO:8; GVYHFAPLTPTPGGK-FAKFAKKFAKFAK; 300 µg/dose) every second day for six days.

Murine hematopoietic stem cells (HSC) will be obtained from StemCell Technologies Inc. Cells will be transfected to express enhanced green fluorescent protein (EGFP). Plasmid pEF-1 a-EGFP, containing an EGFP gene under the control of human EF1, a promoter, and a neomycin-resistance cassette, will be constructed as follows: (1) the promoter region of pEGFP-N3 (Clontech, Palo Alto, Calif.) will be removed by cutting out the AseI-NheI DNA fragment and joining the blunt-ended termini, and (2) human EF1, a promoter from pEF-BOS (a fragment of HindIII and EcoRI DNA) will be inserted into the HindII-EcoRI site of the plasmid. Murine HSC will be transfected with pEF-1 a-EGFP by electroporation and selected in the presence of G418. A single clone that brightly expresses EGFP will be chosen and used for the experiments. The clone will be adapted to feeder-free conditions and maintained on gelatin-coated dishes in Dulbecco's Modified Eagle's Media supplemented with 15% fetal calf serum, 2 mM sodium pyruvate, 2 mM L-glutamine, lx nonessential amino acids, 1,000 units of 0.1 mM 2-mercaptoethanol per mL, along with 100 units of streptomycin and 100 µg of penicillin per mL. Cells will be collected after trypsinization with EDTA and placed in aliquots of the medium described above for mouse tail vein injection 1 hour later.

HSC ($10^6$) will be injected via tail vein into each experimental and control mouse. Ten days later, each animal will be sacrificed. Hearts will be excised and fixed in 2% paraformaldehyde in phosphate-buffered solution (PBS) for 2 hours and cryoprotected in 30% sucrose overnight. Tissue will be embedded in optimum cutting temperature medium and sectioned at 5 µm on a cryostat. Serial sections will be stained with hematoxylin and eosin (H&E). Tissue will be examined with a fluorescent microscope. Percentage of GFP positive cells will be determined for each cardiac tissue sample from each animal by counting 1000 cells in each of four random microscopic fields for each tissue sample. A two-tailed t-test will be used to evaluate the hypothesis that exogenously administered HSC engraft at a higher rate into mice treated with senescent cell cytotoxic agent relative to untreated controls. Special attention will be paid to cardiac tissue in the LAD territory (anterior wall) of each heart.

Example 6

Figure 2:
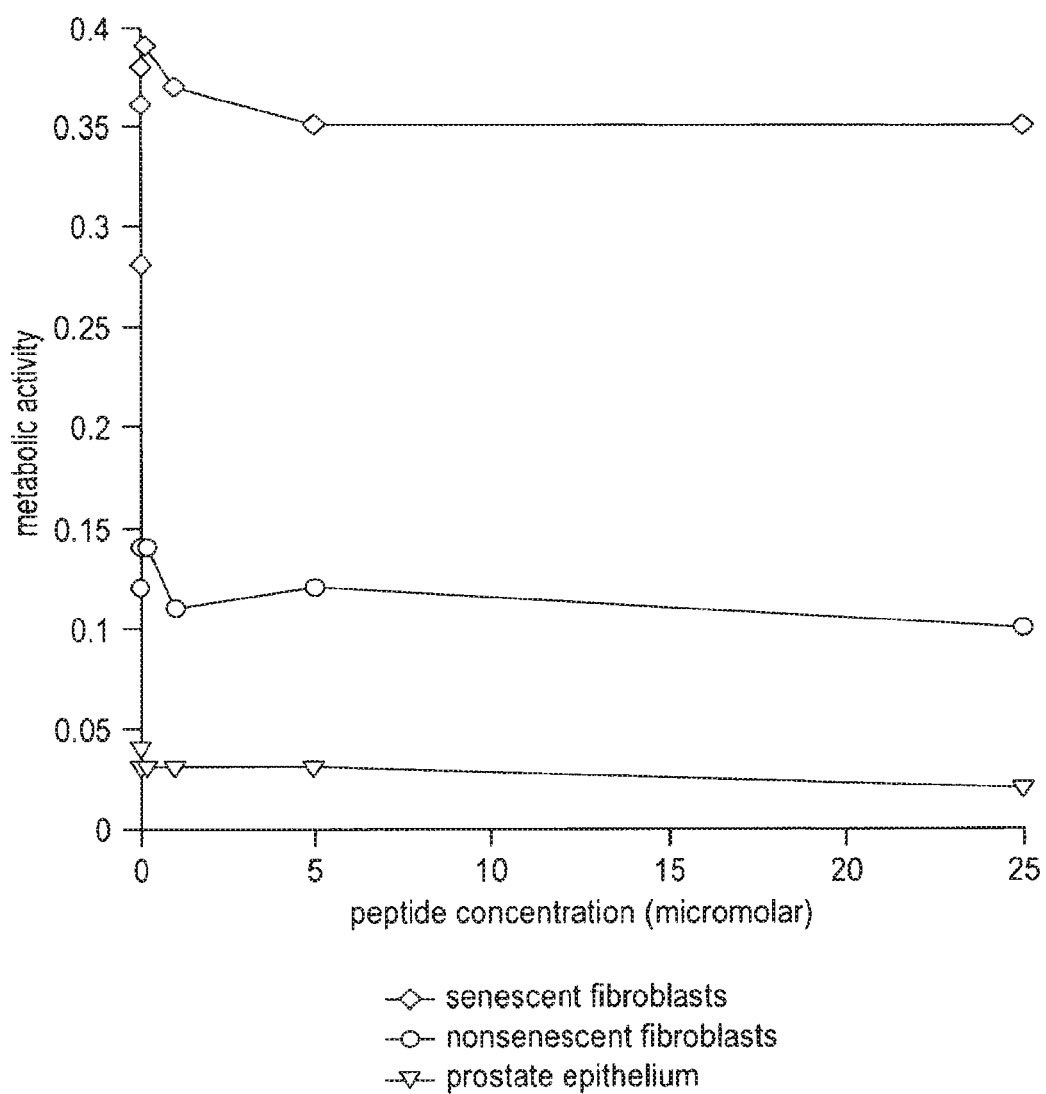
FIG. 2 is a graph showing the results of a WST assay used to measure cell proliferation following treatment with SenL on senescent fibroblasts, non-senescent fibroblasts, and immortalized prostate epithelial cells. The WST-1 assay depends on mitochondrial dehydrogenase levels, and senescent cells have higher mitochondrial mass than their non-senescent counterparts (Martin-Ruiz et al., *J. Biol. Chem.* 279(17):17826-33, 2004). Consequently, baseline values for senescent cells are higher than for the other cell types. Treatment with SenL showed no significant effect on metabolic activity for any of the three cell types and therefore did not affect cell proliferation rates.

In Vitro Validation of the Use of Senescent Cell Binding Agents as Agents to Deliver Molecular Cargo to the Cytoplasm of Senescent Cells Cytotoxicity of Senescent Cell Binding Peptide Conjugated to a Lytic Peptide Sequence Cytotoxic peptide SenL (i.e., SEQ ID NO:6) was synthesized by conjugating a senescent cell binding agent (SEQ ID NO:1) to a lytic peptide sequence (KFAKFAKKFAKFAK; SEQ ID NO:4) via a 4 residue linker (GGGS; SEQ ID NO:10) and tested for differential cytotoxic activity in senescent fibroblasts, prostate epithelial cells, and non-senescent fibroblasts. Senescent fibroblasts exhibited dose-dependent cell death at a significantly higher rate than either non-senescent fibroblasts or prostate epithelial cells (FIG. 1). The effect of SenL on cell proliferation was also assessed using the Cell Proliferation Assay WST-1 (Roche, Mannheim, Germany). As shown in FIG. 2, no change in cell proliferation was seen in any of the three cell types in response to treatment with SenL. The proliferation assay uses WST-1 as a reagent; the reaction is catalyzed by mitochondrial dehydrogenases. Senescent cells have higher mitochondrial mass than their non-senescent counterparts (Lee et al., J. Biomed. Sci. 9:517-26, 2002); consequently, baseline WST assay values are higher for senescent cells. The occurrence of cell death in response to treatment with SenL and absence of change in proliferation rate indicate that SenL causes cell death in non-proliferating cells, e.g. senescent cells.

It is worth noting that each cultured cell population contains a mixture of senescent and non-senescent cells at all population doublings, but that the relative proportion of senescent cells within the population increases stochastically with each population doubling (Martin-Ruiz et al., J. Biol. Chem. 279(17):17826-33, 2004). Thus, the "senescent cells" used in this cell killing experiment are predicted to contain a subpopulation of non-senescent cells. Likewise, a fraction of the "non-senescent cells" used in this experiment are predicted to be senescent. Therefore, the observed difference in cell killing between the two populations is reduced by the impure composition of each population with regard to senescence. This explains why some cytotoxicity is observed in the "non-senescent" fibroblast population. It also explains why the prostate epithelial cells (RWPE-1), which are not predicted to have any senescent cells due to immortalization through HPV-18 transduction, show no cell death at all.

In Vitro Cytotoxicity: Conjugation to Ricin-A

Figure 3:
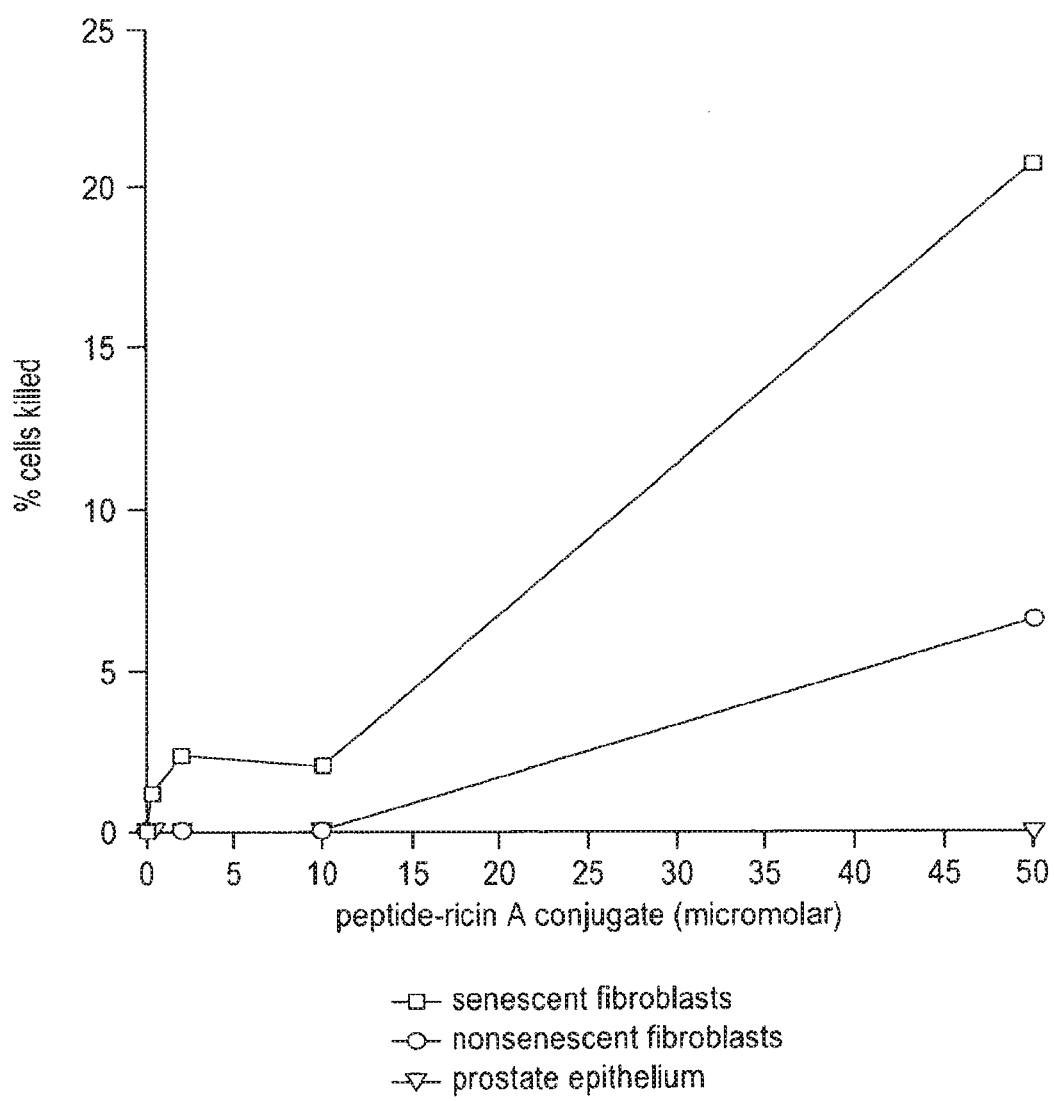
FIG. 3 is a graph showing the cytotoxicity of SenC (SEQ ID NO:5) conjugated to ricin A subunit as tested in senescent fibroblasts, non-senescent fibroblasts, and immortalized prostate epithelial cells. Significantly more senescent cells were killed than non-senescent cells, and no effect was observed on immortalized epithelium.

A senescent cell binding agent (i.e., SEQ ID NO:1) was conjugated to the ricin A subunit via a 4 peptide linker (GGGC; SEQ ID NO:9) to produce SenR (SEQ ID NO:7). Senescent fibroblasts, non-senescent fibroblasts, and prostate epithelial cells were then incubated with the peptide-ricin A conjugate (SenR). Increased cell death was observed in the case of senescent cells treated with SenR than in the other cell types (FIG. 3). For example, an approximately 3 fold increase in cell death was measured in senescent fibroblast when compared to non-senescent fibroblast when treated with 50 µM of SenR.

Binding of Peptide to Senescent Cells Versus Non-Senescent Cells

Figure 4A:
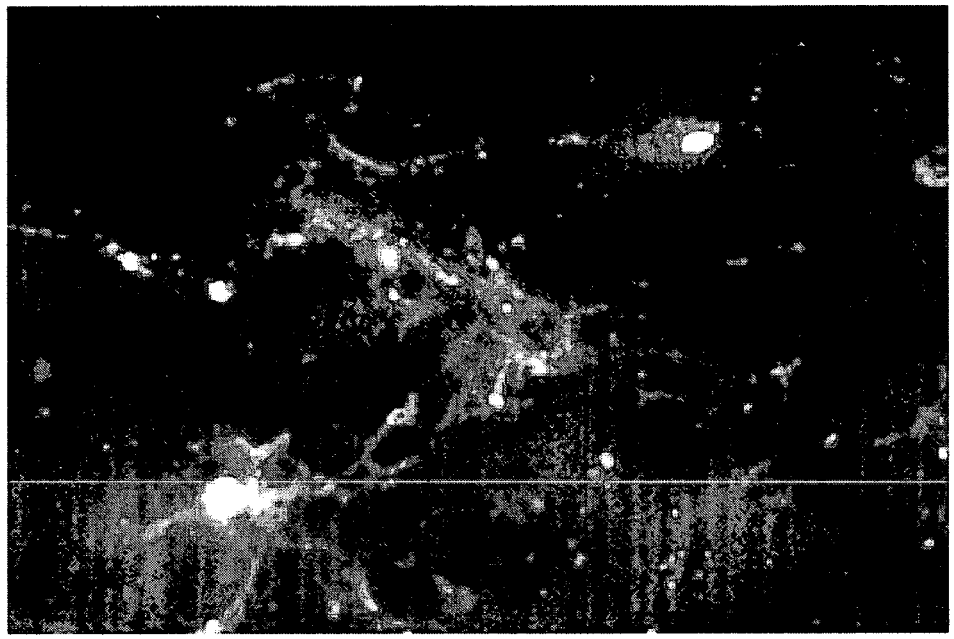
FIGS. 4A and 4B are fluorescent micrographs showing the specific binding of a peptide agent of the invention. Senescent cell binding peptide SenC (SEQ ID NO:5) was conjugated to fluorescein and contacted with senescent fibroblasts (FIG. 4A) and non-senescent fibroblasts (FIG. 4B). Both images were acquired using 1/60 second exposure time. Senescent cells show perinuclear and cytoplasmic staining, indicating significant internalization. Only faint surface staining is visible on the non-senescent cells.
Figure 4B:

In the absence of unlabeled peptide, radio-labeled SenC bound to prostate epithelium, normal fibroblasts, and senescent cells at an average of 0.06%, 0.08%, and 0.32% of added dose, respectively, demonstrating that SenC binds to senescent cells at a higher rate than to the other cell types (P=0.001). In the presence of 20 µM unlabeled SenC, labeled SenC bound to prostate epithelium, normal fibroblasts, and senescent cells at an average of 0.06%, 0.09%, and 0.25% of added dose, respectively. There was no significant difference between binding rates in the presence or absence of unlabeled SenC in the case of prostate epithelium and normal fibroblasts (P=0.5 and 0.4 respectively), indicating that the binding to these cell types is nonspecific. Labeled SenC did bind at significantly different rates to senescent cells in the absence vs. presence of unlabeled SenC (P=0.04), indicative of specific binding (see FIG. 4).

Example 7

Isolation and Identification of Senescent Cell-Specific Antigens

Fibroblasts (CCD-1070Sk) were cultured as outlined above and divided into three groups: replicatively senescent, stress induced prematurely senescent, and non-senescent. Cell surface proteins of each group of cells were conjugated to biotin using the Pierce Cell Surface Protein Isolation Kit (Thermo Scientific, product number 89881) following the instructions of the manufacturer. Membrane proteins were captured using neutravidin following membrane dissolution and sent for 2D gel electrophoresis. Spots from each gel were analyzed to look for differences in protein expression among the three groups of fibroblasts. Protein spots occurring in the gels corresponding to senescent (replicative or stress-induced) cells but not in gels corresponding to non-senescent fibroblasts were identified as senescence-specific antigens and identified using MALDI-TOF mass spectrometry.

Mutant beta-actin (SEQ ID NO:11; GI: 28336) and ACTB protein (SEQ ID NO:12; GI: 15277503) were identified as cell-surface, senescence specific antigens occurring in both replicatively senescent and stress-induced prematurely senescent cells. Drug resistance-related protein LRP (SEQ ID NO:13; GI: 1097308) and major vault protein (SEQ ID NO:14; GI: 19913410) were identified as senescence-specific surface proteins in the replicatively senescent cells only. Senescence specific antigens that were identified in stress induced prematurely senescent cells included thyroid hormone binding protein precursor (SEQ ID NO:15; GI: 339647); unnamed protein product (SEQ ID NO:20; GI: 35655); prolyl 4-hydroxylase, beta subunit precursor (SEQ ID NO:16; GI: 20070125); chain A, human protein disulfide isomerase (SEQ ID NO:17; GI: 159162689); electron-transfer-flavoprotein, beta polypeptide (SEQ ID NO:18; GI: 4503609); unnamed protein product (SEQ ID NO:21; GI: 158257194); unnamed protein product (SEQ ID NO:22; GI: 158259937); ATP synthase, $H^+$ transporting, mitochondrial F1 complex, alpha subunit precursor (SEQ ID NO:19; GI: 4757810), and cathepsin B (SEQ ID NO:23).

Methods
Induction of Replicative Senescence

CCD-1070Sk (fibroblasts) was cultured as described herein. Cells were cultured until they underwent 68 population doublings at which time they displayed typical senescent morphology and underwent minimal further cell growth in response to mitogens.

Isolation of Cell Surface Proteins

Cell surface proteins were extracted from three groups of cells (replicatively senescent fibroblasts, stress-induced prematurely senescent fibroblasts, and non-senescent fibroblasts). Each group of cells contained $10^9$ cells. Cell surface proteins were isolated using the Pierce Cell Surface Protein Isolation Kit (Thermo Scientific, product number 89881), following the instructions of the manufacturer. Protein isolates were analyzed using spectrophotometry which showed absorbances at 280 nm of 1.25, 1.375, and 1.347 for replicatively senescent cells, stress induced prematurely senescent cells, and non-senescent cells respectively. Total volume of each protein isolate was 500 µL.

Identification of Cell Surface Proteins

Cell surface protein isolates were sent for analysis by the proteomics core at the University of Massachusetts Medical School (Worcester, Mass.). The analysis was carried out by performing a buffer exchange for each protein isolate sample followed by 2D gel electrophoresis. Each gel was compared to find protein spots that occurred in the gels corresponding to the senescent (replicative or stress-induced) cells but not in the gels corresponding to the non-senescent cells. Protein spots that occurred in the senescent cell samples but not in the non-senescent samples were digested and sent for mass spectrometry analysis for identification.

Example 8

Immunostaining for Cathepsin B Expression on the Surface of Senescent Cells

Figure 5A:
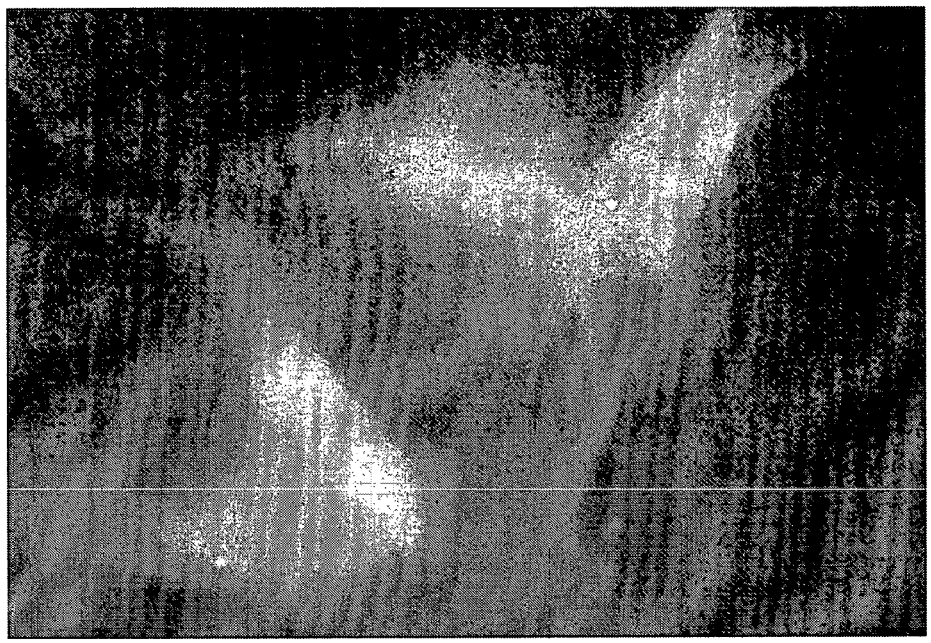
FIGS. 5A and 5B are immunofluorescent micrographs showing the cell surface expression of cathepsin B on senescent cells (FIG. 5A) and lack of expression on non-senescent cells (FIG. 5B).
Figure 5B:
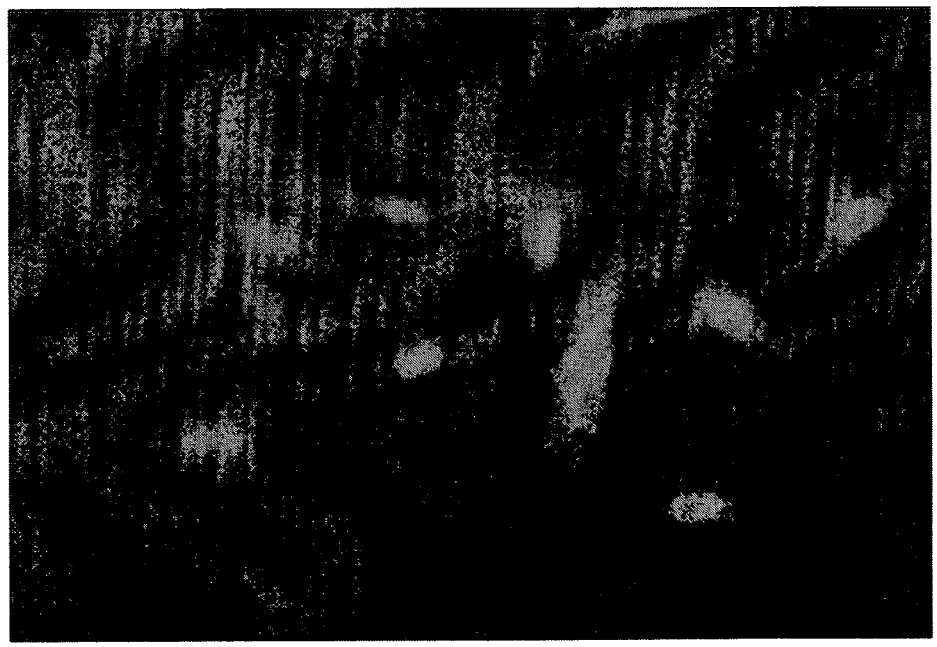

Senescent fibroblasts and non-senescent fibroblasts were grown on cover slips and immunostained for cell surface expression of cathepsin B. Images appear in FIGS. 5A and 5B, which show surface staining for cathepsin B on the senescent cells but not on their non-senescent counterparts.

Fibroblasts (CCD1070Sk) were grown in culture as detailed herein. Replicatively senescent cells were acquired by growing cells for 50 population doublings followed by plating on cover slips. Non-senescent cells were acquired by plating mid passage fibroblasts on cover slips. Cells on cover slips were allowed to attach overnight. Cells were fixed with methanol and washed. Rabbit polyclonal antibody to cathepsin B was diluted 1:100 in PBS with 0.2% BSA. Cells were incubated with primary antibody to cathepsin B for one hour at room temperature followed by washing three times with cold PBS. Secondary antibody (goat anti rabbit IgG conjugated to FITC) was diluted 1:100 in PBS with 0.2% BSA and used to incubate cells for 30 minutes at room temperature. Cells were washed three times with cold PBS.

Example 9

Materials and Methods

Cell Culture

All cells were obtained from American Type Culture Collection (Manassas, Va.). Each cell culture was grown at 37° C. in 5% $CO_2$. CCD-1070Sk (fibroblasts) were grown in minimum essential medium (Eagle) with 2 mM L-glutamine and Earle's BSS adjusted to contain 1.5 g/L sodium bicarbonate, 0.1 mM non-essential amino acids, and 1.0 mM sodium pyruvate, and supplemented with 10% fetal bovine serum. RWPE-1 (non-cancerous prostate epithelial cells) were grown in keratinocyte-serum free medium supplemented with 5 ng/mL human recombinant EGF and 0.05 mg/mL bovine pituitary extract.

Chemical induction of cellular senescence

CCD-1070Sk (fibroblasts) was cultured as described above to 70% confluence. Cells were then treated with 200 µM hydrogen peroxide (i.e., $H_2O_2$) for 2 hours. Media was then replaced with fresh media and cells were allowed to grow for 3 days. Cells were then harvested by trypsinization, split 1:3, and again grown to 70% confluence. Cells were then retreated with 200 µM hydrogen peroxide. Lower passage number fibroblasts frequently required two treatments with hydrogen peroxide, but higher passage fibroblasts occasionally required only a single treatment.

Peptide Synthesis

Peptides were synthesized using standard FMOC protected chemistry. For in vitro cell cytotoxicity studies, peptide was synthesized with a C-terminal, cell lytic sequence according to the following: GVYHFAPLTPT-PGGGS(KFAKFAK)$_2$ (SEQ: ID NO:6; SenL). The peptide sequence GVYHFAPLTPTPGGGC (SEQ ID NO:5; SenC) was synthesized for subsequent conjugation to ricin-A subunit and for radio-labeling with 99m-technetium.

Conjugation of FITC to Peptide

FITC was conjugated to the N terminus of SenC according to the following: (1) A senescent cell binding peptide (SenC; SEQ ID NO:5) was prepared at a concentration of 5 mM in 125 µL of 0.5 M $NaHCO_3$ buffer, pH 9.5, and (2) FITC was added to the peptide solution at a 1:5 molar ratio (peptide:FITC) and diluted to a final volume of 200 µL. The solution was incubated in the dark for 2 hours. Peptide-FITC conjugate was purified on a P4 column using PBS, pH 7.2 as an eluent.

Cell Internalization

Premature senescence of fibroblasts (CCD-1070Sk) was induced as outlined above. Non-senescent fibroblasts were grown in culture as detailed above. Cells were harvested and added to collagen-coated coverslips and grown in MEM plus 10% FBS overnight. Media was removed, and cells were washed once with PBS. Minimal essential media without FBS was added to the cells. A senescent cell binding peptide (SenC; SEQ ID NO:5) conjugated to FITC was added to cells on coverslips at a concentration of 5 µM and incubated for 3 hours. Cells were than washed five times with PBS followed by fixation with 1:1 methanol/acetone for 10 minutes at −20° C. Coverslips were air dried and mounted in fluorescent mounting media with DAPI and visualized with an Olympus BX51 fluorescent microscope and DP70 digital camera with excitation and emission wavelengths of 490 and 520 nm.

Cytotoxicity of Senescent Cell Binding Peptide Conjugated to a Lytic Peptide Sequence CCD-1070Sk and RWPE-1 were grown in culture as detailed above. Premature senescence of fibroblasts was chemically induced as described above. Cells were trypsinated and suspended in culture media containing 10% FBS. Cells were centrifuged at 1,000 rpm for 5 minutes. Supernatant was removed and cells were resuspended in 1 mL media without FBS. Cell suspensions were diluted to 20,000 cells/75 µL. Twenty-five microliters of appropriately-diluted agent solution (SenL; SEQ ID NO:6) was added to cell samples to give various concentrations of 0, 0.1, 0.5, 1.0, 2.5, 5.0 or 10 µM. Each sample was prepared in triplicate. Cell suspensions were transferred to a 96 well plate and incubated in the presence of various concentrations of SenL for 2 hours at 37° C. Six samples of each cell type contained no agent. The assay plate was removed from the incubator, and 2 µL of lysis solution (Tris 25 mM, pH 7.5, 0.5% triton X-100) was added to three samples of each cell type without agent to generate a positive control maximum LDH release. LDH release was measured in each sample by adding 100 µL of CytoTox-ONE Reagent (Roche Applied Science) to each well and mixing on a plate shaker for 30 seconds. Samples were incubated at 22° C. for 10 minutes. The reaction was terminated by adding 50 µL of Stop Solution (per 100 µL of CytoTox-ONE™ Reagent added) to each well. Fluorescence was measured in each well using an excitation wavelength of 530 nm and an emission wavelength of 620 nm (Cytofluor 4000). The CytoTox-ONE assay was shown to yield a quantity of fluorescent product that is linearly proportional to the number of cells killed (correlation coefficient=0.99). The percentage of cells killed was calculated using the following formula:

$$\% \text{ cytotoxicity} = \frac{100\% \times (P - C)}{(M - C)}$$

where P=LDH release in wells of peptide incubated cells; C=LDH release in wells of cells not incubated with peptide; and M=LDH release in wells incubated in lysis solution. The formula is based upon the assumptions that, in a linear relationship between CytoTox-ONE product development and number of cells killed, C is the y-intercept, and M is due to 100% cell killing.

Effect of SenL on Cell Proliferation

Cell proliferation was assayed using the Cell Proliferation Reagent WST-1 (Roche, Mannheim, Germany) by following the manufacturer's instructions.

In Vitro Cytotoxicity: Conjugation to Ricin-A

Peptide SenC (GVYHFAPLTPTPGGGC; SEQ ID NO:5) was conjugated to ricin A subunit (Sigma-Aldrich) to form SenR. Ricin A was obtained from manufacturer in solution. A buffer exchange was performed with 0.1 M PBS/20% glycerol. Ricin A was conjugated with NHS-PEO$_4$-maleimide cross linker (Pierce, Rockford, Ill.) at a 1:10 molar ratio for 30 minutes at room temperature. Derivatized ricin A was purified on a P4 column using 0.1 M PBS/20% glycerol as an elution buffer. Derivatized ricin A was combined with P12S at a 1:1 molar ratio and reacted for 2 hours at room temperature.

CCD-1070Sk and RWPE-1 were grown in culture as detailed above. Senescence was chemically-induced as described above. Cells were trypsinized and suspended in culture media containing 10% FBS. Cells were centrifuged at 1,000 rpm for 5 minutes. Supernatant was removed and cells were resuspended in 1 mL media without FBS. Cell suspensions were diluted to 20,000 cells/75 µL. Twenty-five microliters of appropriately-diluted peptide-ricin A conjugate was added to each cell sample to give various concentrations. Each sample was prepared in triplicate. Cell suspensions were transferred to a 96 well plate and incubated in the presence of peptide-ricin A conjugate for 2 hours at 37° C. Percentage of cells killed (FIG. 3) was determined as outlined above.

Radio-Labeling of Peptide Senescent Cell binding peptide

A senescent cell binding agent (SEQ ID NO:1) was conjugated at its C terminus to the linker sequence GGGC (SEQ ID NO:9) by synthesizing both as a single construct (i.e., SenC; SEQ ID NO:5). The purpose of attaching GGGC was that it can be used to chelate reduced 99m-Tc for radio-labeling. A 2 µL aliquot of conjugated senescent cell binding agent (3 M) was mixed with 40 µL of 0.25 M ammonium acetate, 15 µL of tartrate buffer pH 8.7, 4 µL of stannous chloride in 100 mM of sodium tartrate, and 30 µL of 99m-Tc pertechnetate. The mixture was heated for 25 minutes at 95° C. Quality control was performed with Sep-Pak and was always above 90% purity. A small aliquot was also injected on a Waters 600 HPLC to check the radiological profile. Fractions were collected and read on a gamma counter (Perkin-Elmer Wallac Wizard 1470).

Cell Binding Assay

Binding of radio-labeled SenC (SEQ ID NO:5) to senescent and non-senescent cells was tested by competition with unlabeled SenC. Peptide solutions were prepared to contain 0 or 20 µM of unlabeled SenC, 15 nM radio-labeled SenC, and 0.2% BSA. Chemically-induced senescent fibroblasts, their non-senescent counterparts, and prostate epithelial cells were prepared as above, harvested, and centrifuged. The cell pellets were resuspended in fresh media without FBS, and cells were counted. Peptide solution containing 0 or 20 µM unlabeled SenC and constant concentrations of SenC and $10^5$ senescent cells were combined in a final volume of 200 µL of PBS in Eppendorf tubes and incubated for 4 hours. Cells were pelleted by centrifuging at 2500 rpm for 2 minutes and washed twice with PBS and 0.2% BSA. Pellets were suspended in 5 µL PBS and transferred to 12×75 mm tubes for counting radioactivity using a gamma counter (Perkin-Elmer Wallac Wizard 1470).

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

The invention claimed is:

1. A method for specifically delivering a compound to a senescent cell, the method comprising:
   obtaining a conjugate, wherein the conjugate includes the compound conjugated to a senescent cell binding peptide that contains a senescent cell binding sequence; and
   contacting the cell with the conjugate; thereby specifically delivering the compound to the senescent cell;
   wherein the senescent cell binding peptide configures the conjugate to bind preferentially to senescent cells characterized as expressing senescence associated beta-galactosidase, in comparison with cells not expressing senescence associated beta-galactosidase; and
   wherein the senescent cell binding sequence is selected from SEQ. ID NOS: 1, 2, and 3.

2. The method of claim 1, wherein the compound is a cytotoxic or lytic agent.

3. The method of claim 2, which is a method for specifically killing a senescent cell.

4. The method of claim 2, wherein the cytotoxic or lytic agent is a peptide.

5. The method of claim 4, wherein the cytotoxic or lytic peptide contains SEQ. ID NO: 4 or the ricin A subunit.

6. The method of claim 4, wherein the conjugate is a fusion protein that includes the senescent cell binding peptide conjugated to the cytotoxic peptide by way of a linker peptide selected from SEQ. ID NO:9 and SEQ. ID NO:10.

7. The method of claim 1, wherein the compound is a cytotoxic or therapeutic moiety that is not a peptide.

8. The method of claim 7, wherein the cytotoxic or therapeutic moiety is a fluorochrome.

9. The method of claim 1, wherein the cell is contacted with the conjugate in vitro.

10. A method of preparing a conjugate that is configured to specifically deliver a compound to a senescent cell in accordance with claim 1, the method comprising:
obtaining a senescent cell binding peptide that contains the senescent cell binding sequence;
obtaining the compound; and
conjugating the senescent cell binding peptide to the compound to form a conjugate;
whereby the senescent cell binding peptide configures the conjugate to bind preferentially to senescent cells characterized as expressing senescence associated beta-galactosidase, in comparison with cells not expressing senescence associated beta-galactosidase.

11. The method of claim 10, wherein the compound is a cytotoxic or lytic agent.

12. A conjugate that is configured to specifically deliver a compound to a senescent cell in accordance with claim 1, wherein the conjugate comprises:
a senescent cell binding peptide that contains said senescent cell binding sequence; and
said compound;
wherein the compound is conjugated to the senescent cell binding peptide in such a manner that the conjugate resulting therefrom binds specifically to senescent cells characterized as expressing senescence associated beta-galactosidase, in comparison with cells not expressing senescence associated beta-galactosidase.

13. The conjugate of claim 12, wherein the compound is a cytotoxic or lytic agent.

14. A method for identifying a senescent cell binding polypeptide having a binding specificity that is effective for specifically delivering a compound to a senescent cell, the method comprising: obtaining a library of polypeptides for testing as potential senescent cell binding agents; obtaining a population of senescent cells that are characterized as being non-cancer cells that express both p16 and senescence associated beta-galactosidase; contacting the senescent cells with polypeptides from the library; contacting non-senescent cells with polypeptides from the library; and identifying one or more polypeptides from the library that have bound to the senescent cells but not the non-senescent cells as senescent cell binding agents having a binding specificity that is effective for specifically delivering a compound to a senescent cell.

15. The method of claim 14, comprising:
contacting non-senescent cells with polypeptides from the library; and
recovering polypeptides that have not bound to the non-senescent cells in the preceding step, thereby producing a subtraction library;
contacting senescent cells with polypeptides from the subtraction library; and
recovering polypeptides that have bound to the senescent cells in the preceding step;
thereby producing a library of polypeptides that are identified as senescent cell binding agents having a binding specificity that is effective for specifically delivering a compound to a senescent cell.

16. The method of claim 14, further comprising sequencing one or more of the polypeptides identified as being senescent cell binding agents, thereby obtaining a senescent cell binding sequence for each of the sequenced polypeptides.

17. The method of claim 16, further comprising determining a consensus sequence from a plurality of the senescent cell binding sequences.

18. The method of claim 14, further comprising conjugating a compound to be delivered to a senescent cell to at least one of said identified polypeptides.

* * * * *